US008563615B2

(12) United States Patent  
Tsai et al.

(10) Patent No.: US 8,563,615 B2  
(45) Date of Patent: Oct. 22, 2013

(54) USE OF CI-994 AND DINALINE FOR THE TREATMENT OF MEMORY/COGNITION AND ANXIETY DISORDERS

(75) Inventors: Li-Huei Tsai, Cambridge, MA (US); Ji-Song Guan, Beijing (CN); Stephen J. Haggarty, Dorchester, MA (US); Edward Holson, Newton Highlands, MA (US); Florence Wagner, Ashland, MA (US); Johannes Graeff, Waban, MA (US)

(73) Assignees: Massachusetts Institute of Technology, Cambridge, MA (US); The Broad Institute, Inc., Cambridge, MA (US); Massachusetts General Hospital, Boston, MA (US)

( * ) Notice: Subject to any disclaimer, the term of this patent is extended or adjusted under 35 U.S.C. 154(b) by 59 days.

(21) Appl. No.: 12/917,402

(22) Filed: Nov. 1, 2010

(65) Prior Publication Data

US 2011/0224303 A1  Sep. 15, 2011

Related U.S. Application Data

(60) Provisional application No. 61/256,927, filed on Oct. 30, 2009, provisional application No. 61/265,468, filed on Dec. 1, 2009.

(51) Int. Cl.
| | | |
|---|---|---|
| *A01N 37/18* | (2006.01) | |
| *A01N 33/18* | (2006.01) | |
| *A01N 33/24* | (2006.01) | |
| *A61K 31/165* | (2006.01) | |
| *A61K 31/12* | (2006.01) | |
| *C07C 233/00* | (2006.01) | |
| *C07C 235/00* | (2006.01) | |
| *C07C 237/00* | (2006.01) | |

(52) U.S. Cl.
USPC ............ 514/617; 514/676; 514/688; 564/161

(58) Field of Classification Search
USPC ........................ 514/617, 676, 688; 564/161
See application file for complete search history.

(56) References Cited

U.S. PATENT DOCUMENTS

| 7,183,298 | B2 | 2/2007 | Watkins et al. |
|---|---|---|---|
| 8,088,951 | B2 | 1/2012 | Tsai et al. |
| 8,263,547 | B2 | 9/2012 | Tsai et al. |
| 2003/0235588 | A1 | 12/2003 | Richon et al. |
| 2004/0077591 | A1 | 4/2004 | Dangond |
| 2004/0087657 | A1 | 5/2004 | Richon et al. |
| 2004/0122101 | A1 | 6/2004 | Miller et al. |
| 2005/0037992 | A1 | 2/2005 | Lyons et al. |
| 2005/0227929 | A1 | 10/2005 | Masferrer |
| 2005/0288227 | A1 | 12/2005 | Marks et al. |
| 2006/0008517 | A1 | 1/2006 | Lynch et al. |
| 2006/0018921 | A1 | 1/2006 | Levenson et al. |
| 2006/0258694 | A1 | 11/2006 | Bressi et al. |
| 2007/0015183 | A1 | 1/2007 | Krainc |
| 2007/0078825 | A1 | 4/2007 | Barlow et al. |
| 2007/0129331 | A1 | 6/2007 | Gately et al. |
| 2007/0197438 | A1 | 8/2007 | Reiser et al. |
| 2007/0232528 | A1 | 10/2007 | Franke |
| 2008/0300205 | A1 | 12/2008 | Tsai et al. |
| 2010/0015130 | A1 | 1/2010 | Tsai et al. |
| 2010/0075926 | A1 | 3/2010 | Tsai et al. |
| 2011/0008468 | A1 | 1/2011 | Haggarty et al. |
| 2011/0009475 | A1 | 1/2011 | Tsai et al. |
| 2012/0039909 | A1 | 2/2012 | Tsai et al. |
| 2012/0101147 | A1 | 4/2012 | Tsai et al. |
| 2012/0322879 | A1 | 12/2012 | Tsai et al. |
| 2013/0004517 | A1 | 1/2013 | Tsai et al. |
| 2013/0096129 | A1 | 4/2013 | Tsai et al. |

FOREIGN PATENT DOCUMENTS

| EP | 1 591 109 A1 | 11/2005 |
|---|---|---|
| WO | WO-01/38322 A1 | 5/2001 |
| WO | WO-03/024448 A2 | 3/2003 |
| WO | WO-2004/035525 A1 | 4/2004 |
| WO | WO-2005/030704 A1 | 4/2005 |
| WO | WO-2005/092899 A1 | 10/2005 |
| WO | WO-2006-052916 A2 | 5/2006 |
| WO | WO-2007-049262 A1 | 5/2007 |
| WO | WO-2007/055942 A2 | 5/2007 |
| WO | WO-2007/100657 A2 | 9/2007 |
| WO | WO-2007/118137 A1 | 10/2007 |
| WO | WO-2007/127137 A2 | 11/2007 |
| WO | WO-2007/136605 A2 | 11/2007 |
| WO | WO 2008/008472 A2 | 1/2008 |
| WO | WO-2008/109994 A1 | 9/2008 |
| WO | WO-2010-065117 A1 | 6/2010 |

OTHER PUBLICATIONS

Lattal et al. "Systemic or Intrahippocampla Delivery of Histone Deacetylase Inhibitors Facilitates Fear Extinction" Behavioral Neuroscience, 2007, vol. 121, No. 5, pp. 1125-1131.*
Boutillier et al., Constitutive repression of E2F1 transcriptional activity through HDAC proteins is essential for neuronal survival. Ann N Y Acad Sci. Nov. 2002;973:438-42.
Boutillier et al., Selective E2F-dependent gene transcription is controlled by histone deacetylase activity during neuronal apoptosis. J Neurochem. Feb. 2003;84(4):814-28.
Bredy et al., The histone deacetylase inhibitor valproic acid enhances acquisition, extinction, and reconsolidation of conditioned fear. Learn Mem. Jan. 3, 2008;15(1):39-45. Print Jan. 2008.
Cerna et al., Histone deacetylation as a target for radiosensitization. Curr Top Dev Biol. 2006;73:173-204. Review.

(Continued)

*Primary Examiner* — Kendra D Carter
(74) *Attorney, Agent, or Firm* — Wolf, Greenfield & Sacks, P.C.

(57) ABSTRACT

The invention relates to methods and compositions for promoting cognitive function and/or treating cognitive function disorders and impairments. In particular the methods are accomplished by administering to a subject CI-994 or dinaline or a pharmaceutically acceptable salt, ester, prodrug or metabolite thereof.

10 Claims, 66 Drawing Sheets

(56) References Cited

OTHER PUBLICATIONS

Citrome, Schizophrenia and valproate. Psychopharmacol Bull. 2003;37 Suppl 2:74-88. Review.
Cruz et al., A Jekyll and Hyde kinase: roles for Cdk5 in brain development and disease. Curr Opin Neurobiol. Jun. 2004;14(3):390-4. Review.
Cruz et al., Aberrant Cdk5 activation by p25 triggers pathological events leading to neurodegeneration and neurofibrillary tangles. Neuron. Oct. 30, 2003;40(3):471-83.
Fischer et al., Recovery of learning and memory is associated with chromatin remodelling. Nature. May 10, 2007;447(7141):178-82. Epub Apr. 29, 2007.
Fischer et al., Opposing roles of transient and prolonged expression of p25 in synaptic plasticity and hippocampus-dependent memory. Neuron. Dec. 8, 2005;48(5):825-38.
Frankland et al., The involvement of the anterior cingulate cortex in remote contextual fear memory. Science. May 7, 2004;304(5672):881-3.
Gould et al., Emerging experimental therapeutics for bipolar disorder: insights from the molecular and cellular actions of current mood stabilizers. Mol Psychiatry. Aug. 2004;9(8):734-55.
Gould et al., Signaling networks in the pathophysiology and treatment of mood disorders. J Psychosom Res. Aug. 2002;53(2):687-97. Review.
Guan et al., HDAC2 negatively regulates memory formation and synaptic plasticity. Nature. May 7, 2009;459(7243):55-60.
Hockly et al., Suberoylanilide hydroxamic acid, a histone deacetylase inhibitor, ameliorates motor deficits in a mouse model of Huntington's disease. Proc Natl Acad Sci U S A. Feb. 18, 2003;100(4):2041-6. Epub Feb. 7, 2003.
Horn et al., Neuronal-based synaptic compensation: a computational study in Alzheimer's disease. Neural Comput. Aug. 15, 1996;8(6):1227-43.
Hu et al., Identification of novel isoform-selective inhibitors within class I histone deacetylases. J Pharmacol Exp Ther. Nov. 2003;307(2):720-8. Epub Sep. 15, 2003.
Johannessen et al., Valproate: past, present, and future. CNS Drug Rev. 2003 Summer;9(2):199-216.
Kim et al., Deregulation of HDAC1 by p25/Cdk5 in neurotoxicity. Neuron. Dec. 10, 2008;60(5):803-17.
Kim et al., Inhibition of histone deacetylation enhances the neurotoxicity induced by the C-terminal fragments of amyloid precursor protein. J Neurosci Res. Jan. 1, 2004;75(1):117-24.
Kim et al., SIRT1 deacetylase protects against neurodegeneration in models for Alzheimer's disease and amyotrophic lateral sclerosis. EMBO J. Jul. 11, 2007;26(13):3169-79. Epub Jun. 21, 2007.
Langley et al., Remodeling chromatin and stress resistance in the central nervous system: histone deacetylase inhibitors as novel and broadly effective neuroprotective agents. Curr Drug Targets CNS Neurol Disord. Feb. 2005;4(1):41-50. Review.
Lattal et al., Systemic or intrahippocampal delivery of histone deacetylase inhibitors facilitates fear extinction. Behav Neurosci. Oct. 2007;121(5):1125-31.
Leng et al., Synergistic neuroprotective effects of lithium and valproic acid or other histone deacetylase inhibitors in neurons: roles of glycogen synthase kinase-3 inhibition. J Neurosci. Mar. 5, 2008;28(10):2576-88.
Levenson et al., Regulation of histone acetylation during memory formation in the hippocampus. J Biol Chem. Sep. 24, 2004;279(39):40545-59. Epub Jul. 23, 2004.
Manji et al., The underlying neurobiology of bipolar disorder. World Psychiatry. Oct. 2003;2(3):136-46.
Mao et al., Disrupted in schizophrenia 1 regulates neuronal progenitor proliferation via modulation of GSK3beta/beta-catenin signalin. Cell. Mar. 20, 2009;136(6):1017-31.
McCampbell et al., Histone deacetylase inhibitors reduce polyglutamine toxicity. Proc Natl Acad Sci U S A. Dec. 18, 2001;98(26):15179-84. Epub Dec. 11, 2001.

Monfils et al., Extinction-reconsolidation boundaries: key to persistent attenuation of fear memories. Science. May 15, 2009;324(5929):951-5. Epub Apr. 2, 2009.
Morrison et al., Neuroprotection by histone deacetylase-related protein. Mol Cell Biol. May 2006;26(9):3550-64.
Neugebauer et al., Inhibitors of Nad+ dependent histone deacetylases (sirtuins). Curr Pharm Des. 2008;14(6):562-73. Review.
Ng et al., Histone deacetylases: silencers for hire. Trends Biochem Sci. Mar. 2000;25(3):121-6. Review.
Richards et al., Gemcitabine plus CI-994 offers no advantage over gemcitabine alone in the treatment of patients with advanced pancreatic cancer: results of a phase II randomized, double-blind, placebo-controlled, multicenter study. Ann Oncol. Jul. 2006;17(7):1096-102. Epub Apr. 26, 2006.
Salminen et al., Neuronal apoptosis induced by histone deacetylase inhibitors. Brain Res Mol Brain Res. Oct. 30, 1998;61(1-2):203-6.
Sancar et al., Molecular mechanisms of mammalian DNA repair and the DNA damage checkpoints. Annu Rev Biochem. 2004;73:39-85. Review.
Schiller et al., Preventing the return of fear in humans using reconsolidation update mechanisms. Nature. Jan. 7, 2010;463(7277):49-53. Epub Dec. 9, 2009.
Schnurr et al., Cognitive behavioral therapy for posttraumatic stress disorder in women: a randomized controlled trial. JAMA. Feb. 28, 2007;297(8):820-30.
Steffan et al., Histone deacetylase inhibitors arrest polyglutamine-dependent neurodegeneration in Drosophila. Nature. Oct. 18, 2001;413(6857):739-43.
Sweatt, Behavioural neuroscience: Down memory lane. Nature. May 10, 2007;447(7141):151-2.
Tsankova et al., Sustained hippocampal chromatin regulation in a mouse model of depression and antidepressant action. Nature Neuroscience 9: Apr. 2006 (519-525).
Van Praag et al., Neural consequences of environmental enrichment. Nat Rev Neurosci. Dec. 2000;1(3):191-8. Review.
Wada et al., Alpha-keto amides as inhibitors of histone deacetylase. Bioorg Med Chem Lett. Oct. 6, 2003;13(19):3331-5.
Wade et al., Histone acetylation: chromatin in action. Trends Biochem Sci. Apr. 1997;22(4):128-32. Review.
Zarate et al., Molecular mechanisms of bipolar disorder. Drug Disc Today: Disease Mech. 2005;2(4):435-45.
Alkire, Hypothesis: Supression of memory protein formation underlies anesthetic-induced amnesia. Anesthesiology. 2008;109:768-70.
Cardin et al., Memory suppressor genes: enhancing the relationship between synaptic plasticity and memory storage. J Neurosci Res. 1999;58:10-23.
Colangelo, The recovered memory controversy: a representative case study. J Child Sex Abus. Jan.-Feb. 2009;18(1):103-21.
Geraerts et al., Forgetting unwanted memories: directed forgetting and thought suppression methods. Acta Psychol (Amst). Mar. 2008;127(3):614-22. Epub Feb. 14, 2008.
Levy et al., Individual differences in the suppression of unwanted memories: the executive deficit hypothesis. Acta Psychologica. 2008;127:623-35.
Prendergast et al., Treatment with histone deacetylase inhibitors SAHA and MS-275 ameliorates the core symptoms of asocialty and cognitive impairment in an animal model of autism. 38th Annual meeting of the society-for-neuroscience. Nov. 15-19, 2008.
Sleiman et al., Putting the 'Hat' back on survival signalling: the promises and challenges of HDAC inhibition in the treatment of neurological conditions. Expert Opin Investig Drugs. May 2009;18(5):573-84.
Graff et al., an epigenetic blockade of cognitive functions in the neurodegenerating brain. Nature. Feb. 29, 2012;483(7388):222-6.
Kang et al., Neuroprotective effects of naturally occurring biflavonoids. Bioorg Med Chem Lett. Aug. 1, 2005;15(15):3588-91.
Methot et al., Exploration of the internal cavity of histone deacetylase (HDAC) with selective HDAC1/HDAC2 inhibitors (SHI-1:2). Bioorg Med Chem Lett. Feb. 1, 2008;18(3):973-8. Epub Jan. 7, 2008.
Verbraecken et al., Body surface area in normal-weight, overweight, and obese adults. A comparison study. Metabolism. Apr. 2006;55(4):515-24.

\* cited by examiner

FIG. 1

Characterization of CI-994 and dinaline as HDAC inhibitors

Isoform potency and selectivity of known and novel memory enhancers

| | | Class I HDACs | | | | Class IIa HDACs | | | | Class IIb HDACs | | Class IV HDACs |
|---|---|---|---|---|---|---|---|---|---|---|---|---|
| Compound | HDAC1 | HDAC2 | HDAC3 | HDAC8 | HDAC4 | HDAC5 | HDAC7 | HDAC9 | HDAC6 | HDAC10 | HDAC11 |
| memory enhancers | | | | | | | | | | | | |
| buturate | 8.3 | 7.04 | 4.82 | 10.4 | 5,726 | 6,403 | 4,380 | 5,619 | 5,881 | | |
| Valproate | 35.4 | 59.2 | 218 | 97.1 | >10,000 | >10,000 | >10,000 | >10,000 | >10,000 | | |
| SAHA | 0.002 | 0.003 | 0.006 | 0.700 | >30 | >15 | >30 | >30 | 0.004 | | |
| CI-994 | 0.299 | 0.432 | 1.33 | >30 | >30 | >30 | >30 | >30 | >30 | | |
| Dinaline | 0.681 | 0.931 | 1.39 | >30 | >30 | >30 | >30 | >30 | >30 | | >30 |

*In vitro* HDAC $IC_{50}$ (µM); with isoform-specific substrates
(10 min pre-incubation)

FIG. 1A  Characterization of CI-994 and dinaline as time dependent HDAC inhibitors Isoform potency and selectivity of known and novel memory enhancers

| Compound | Class I HDACs | | | | Class IIa HDACs | | | | Class IIb HDACs | | Class IV HDACs |
|---|---|---|---|---|---|---|---|---|---|---|---|
| | HDAC1 | HDAC2 | HDAC3 | HDAC8 | HDAC4 | HDAC5 | HDAC7 | HDAC9 | HDAC6 | HDAC10 | HDAC11 |
| buturate | 8.3 | 7.04 | 4.82 | 10.4 | 5,726 | 6,403 | 4,380 | 5,619 | 5,881 | | |
| Valproate | 35.4 | 59.2 | 218 | 97.1 | >10,000 | >10,000 | >10,000 | >10,000 | >10,000 | | |
| SAHA | 0.002 | 0.003 | 0.006 | 0.700 | >30 | >15 | >30 | >30 | 0.004 | | |
| CI-994 | 0.040 | 0.050 | 0.050 | >30 | >30 | >30 | >30 | >30 | >30 | | |
| Dinaline | 0.149 | 0.078 | 0.104 | >30 | >30 | >30 | >30 | >30 | >30 | | >30 |

*In vitro* HDAC $IC_{50}$ (µM); with isoform-specific substrates
(1–3 h pre-incubation)

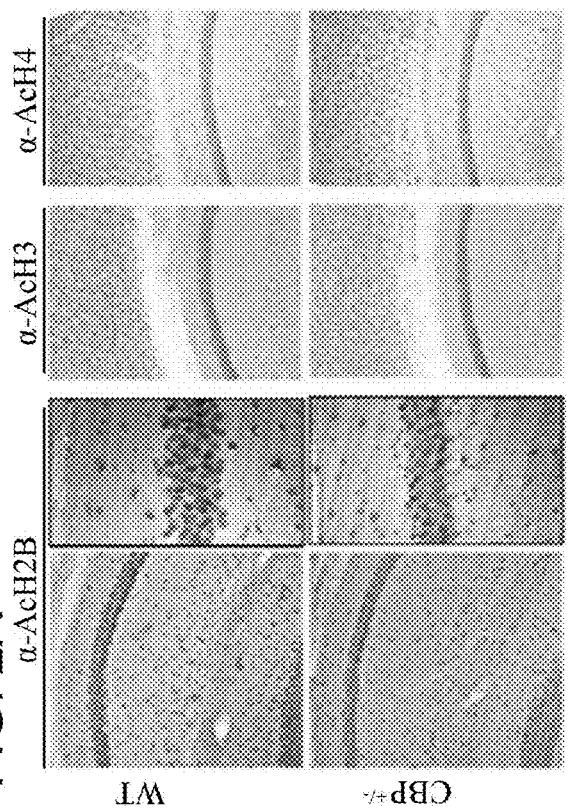
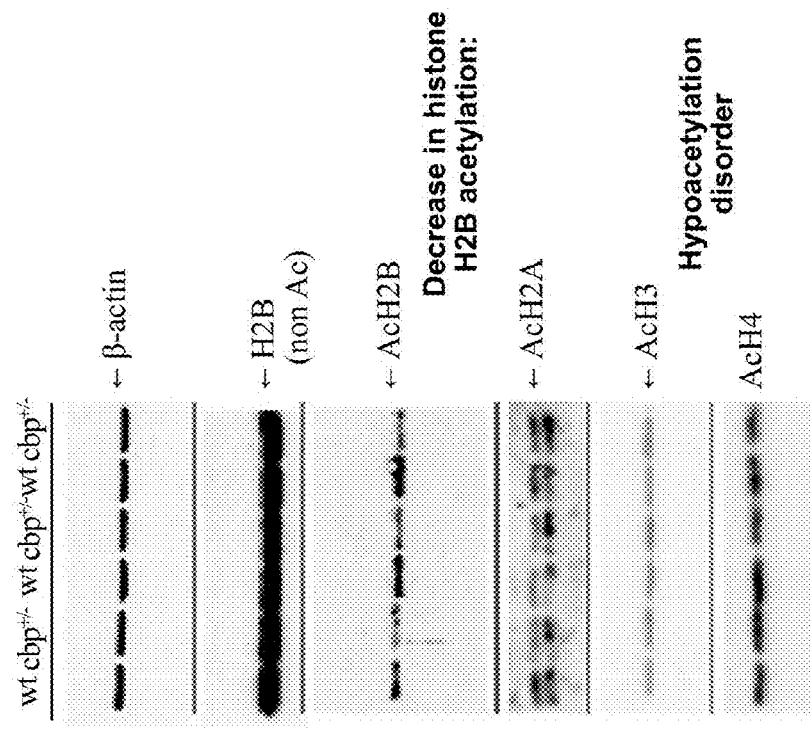
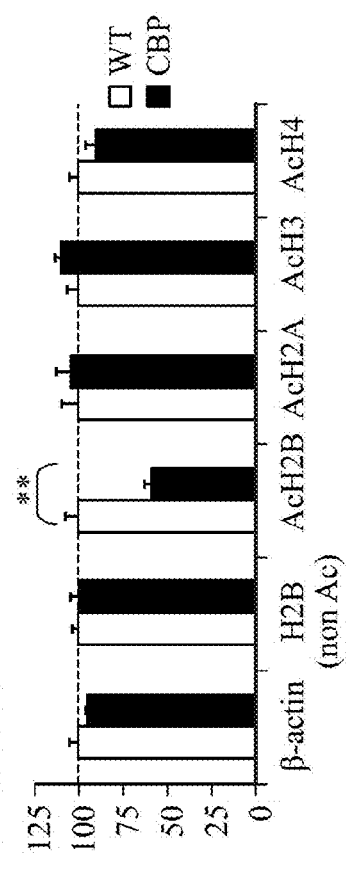
FIG. 2A In vivo HDACi biomarkers: Acetylation marks in Rubinstein Taybi CBP+/- mice
FIG. 2B
FIG. 2C
From Alarcon et al. Neuron. 2004 Jun 24;42(6):947-59

FIG. 4 Within the Class I HDACs, HDAC2 negatively regulates memory formation and synaptic plasticity.

Treatment of neuronal cells with CI-994 enhances H4 and H2B histone acetylation *in vitro*.

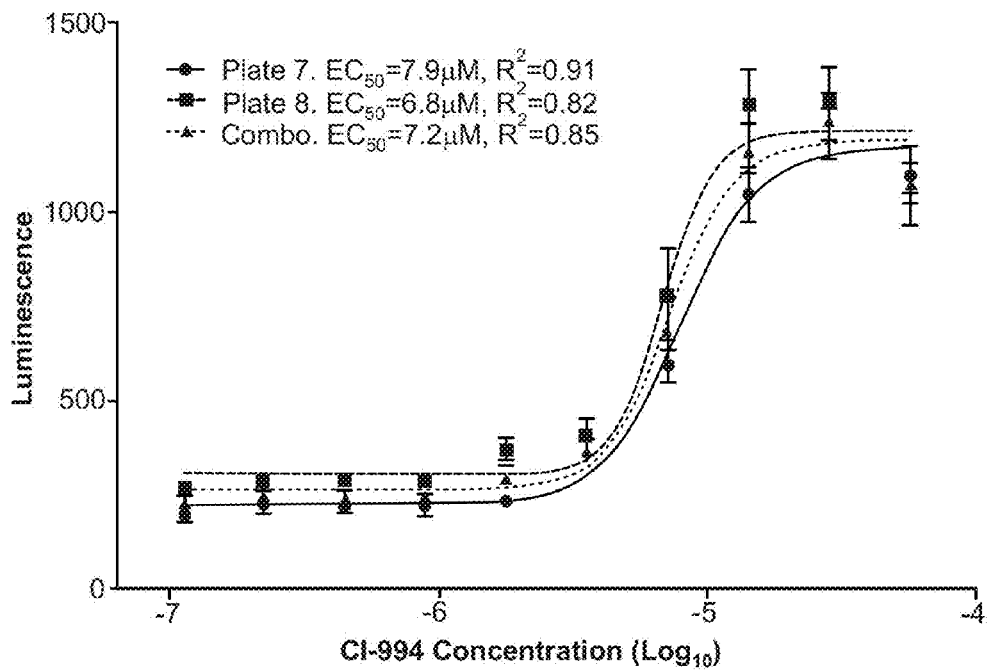
FIG. 14A Dose response of CI-994 in TCF/LEF reporter gene in human neural progenitor cells.
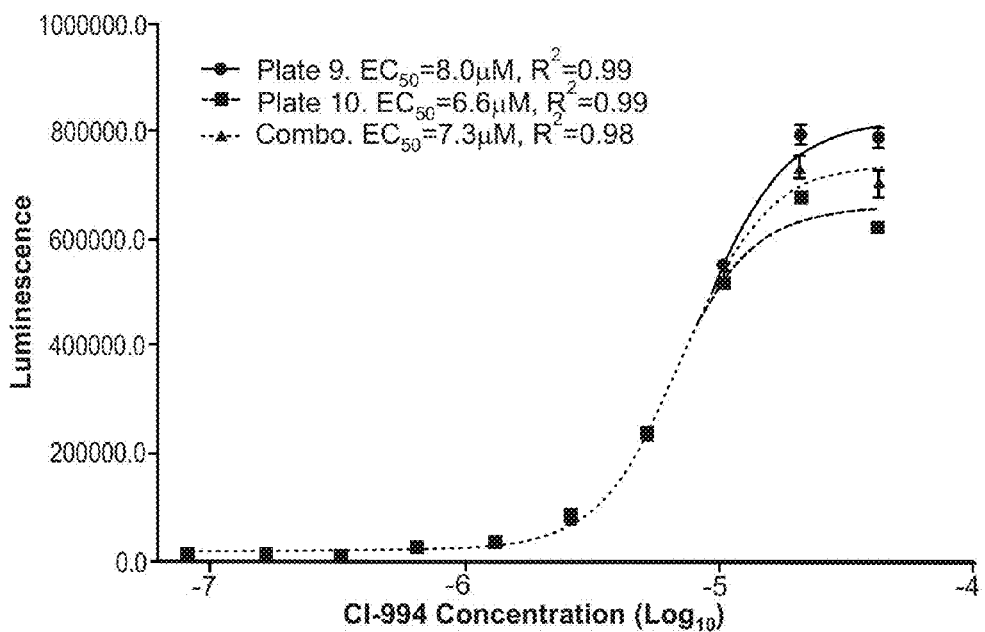
FIG. 14B

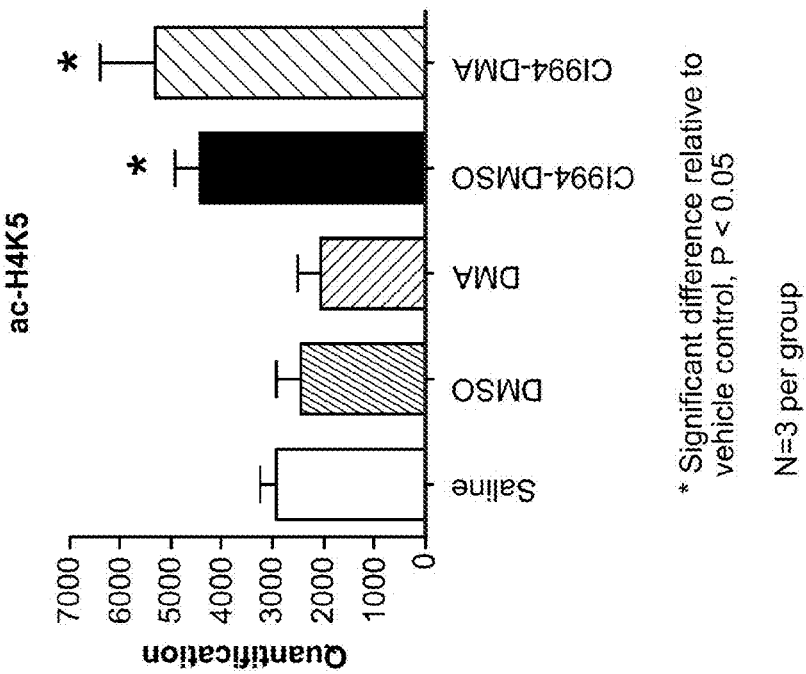
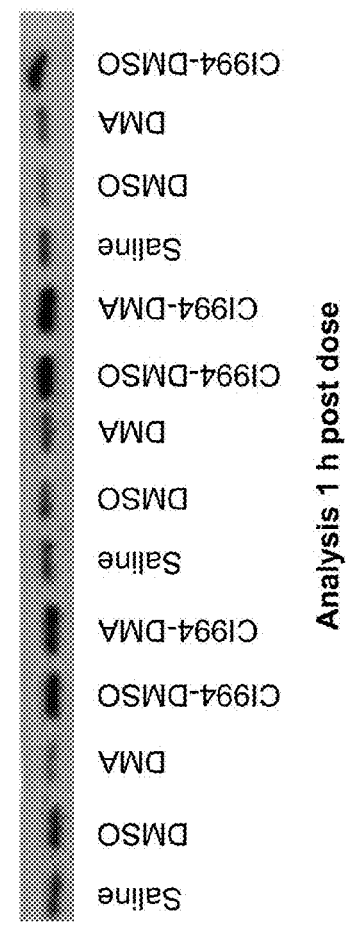
FIG. 19A
FIG. 19B

Acute treatment with CI-994 enhances histone acetylation in whole brain. 30 mg/kg, i.p, single dose.

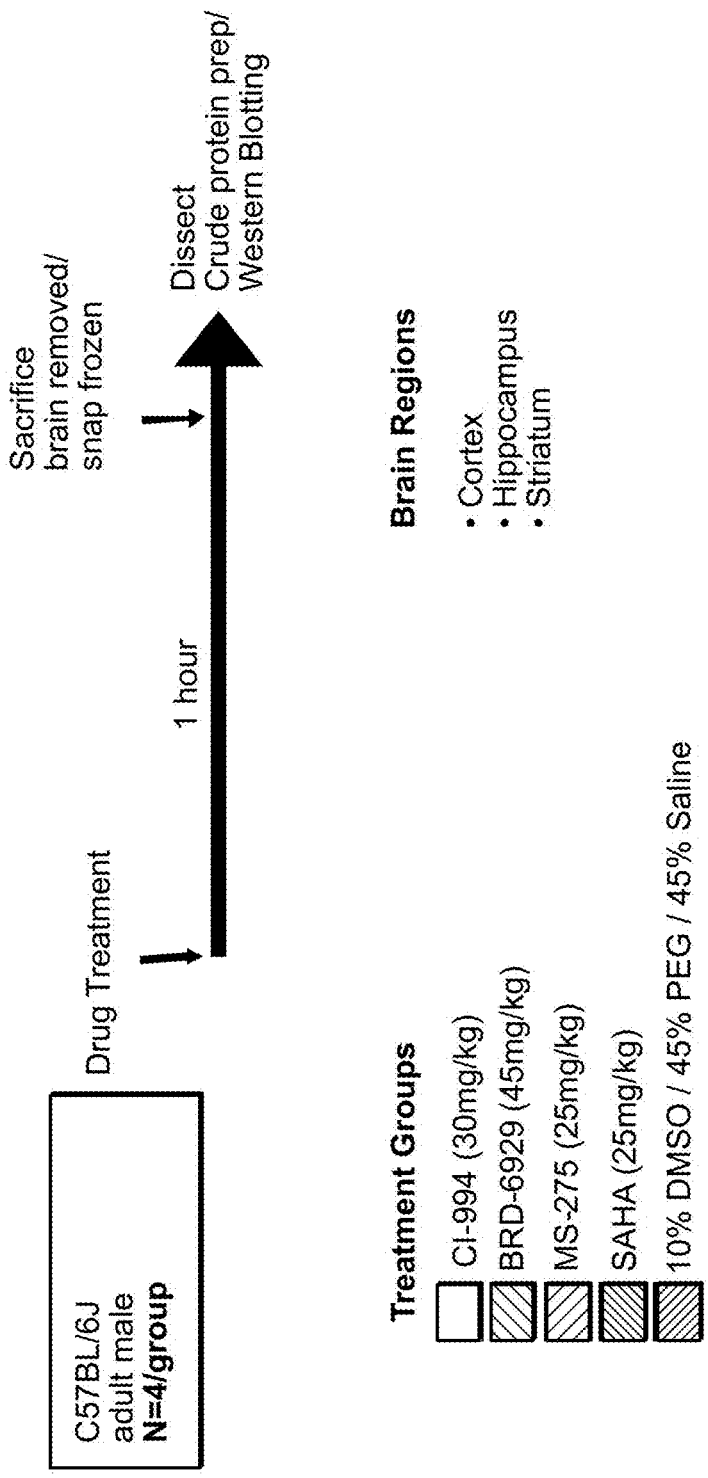

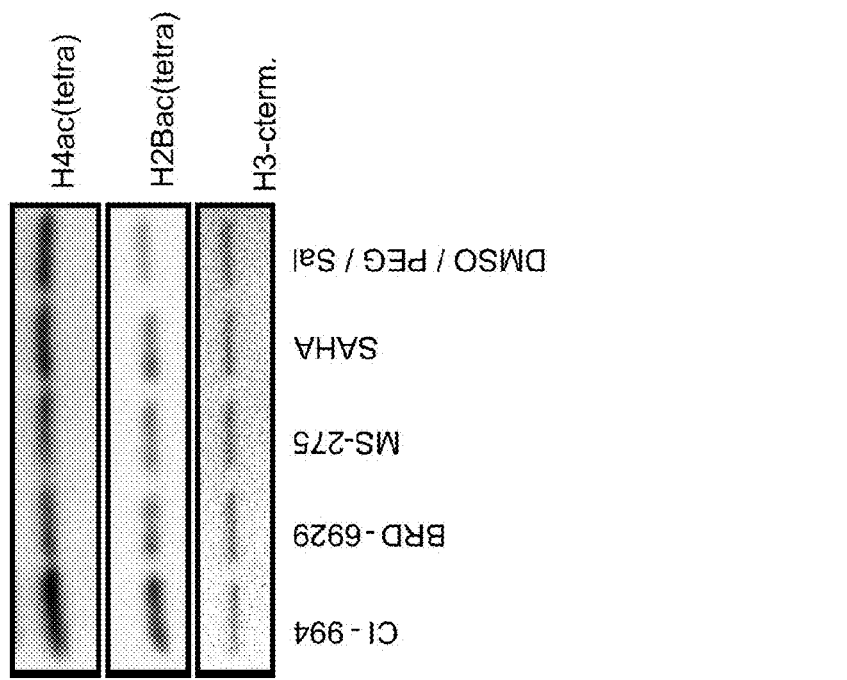
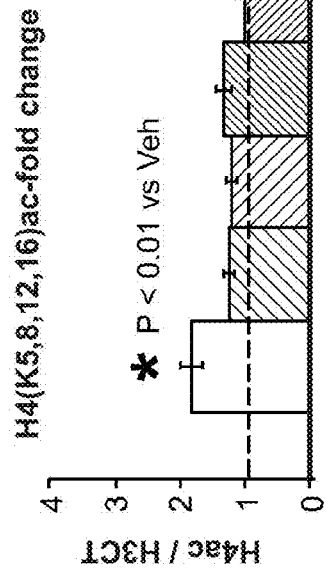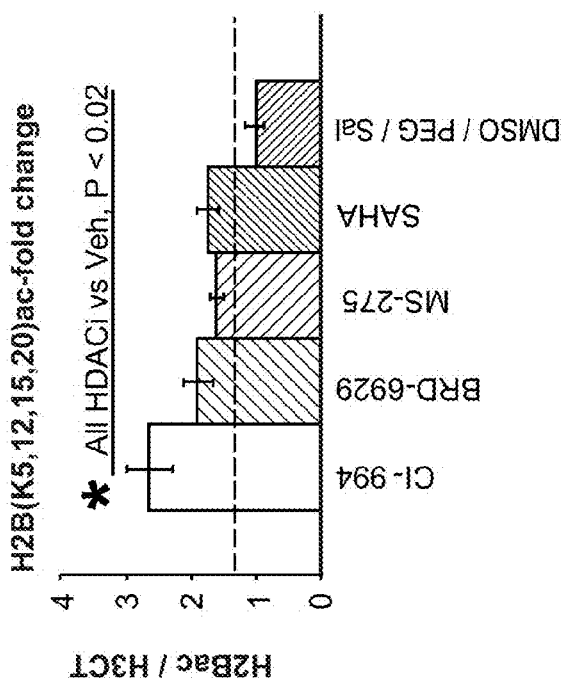
FIG. 22A
FIG. 22B
Acute treatment with CI-994 causes increased H4 and H2B (tetra) histone acetylation in cortex of adult male C57BL/6J mice

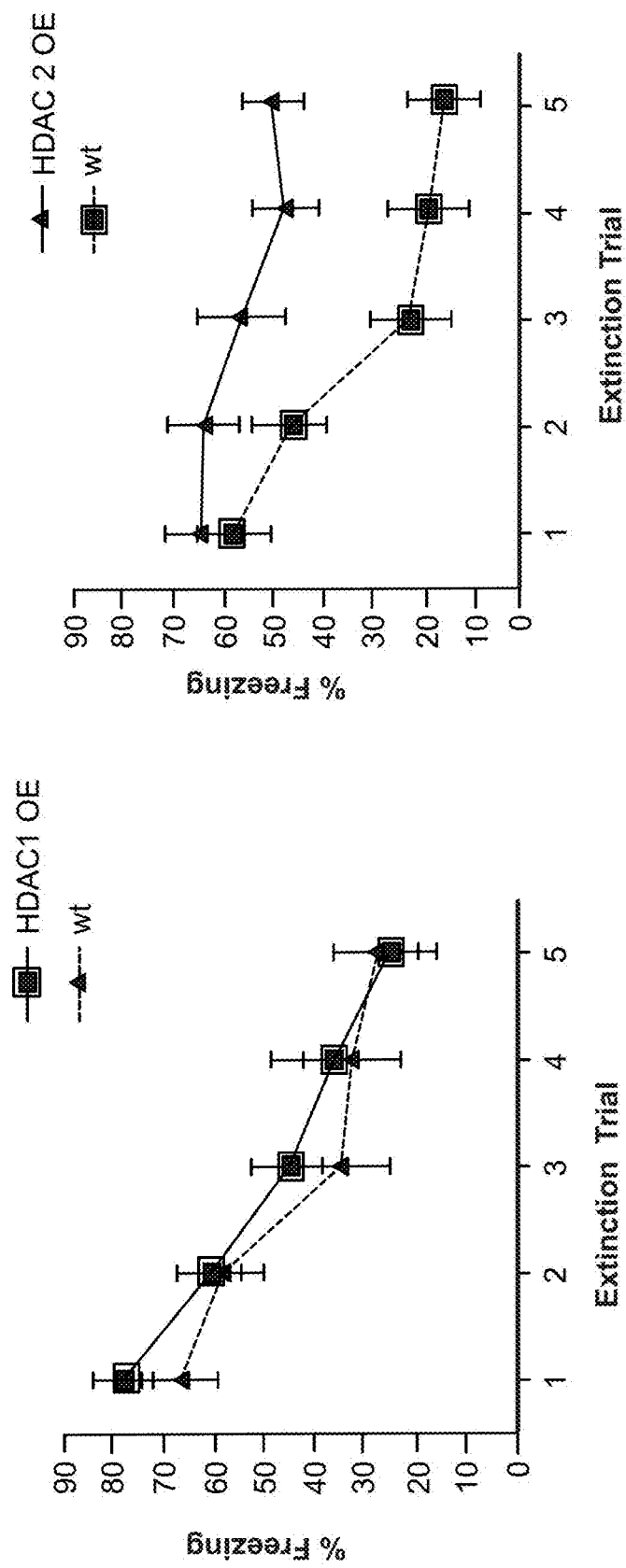

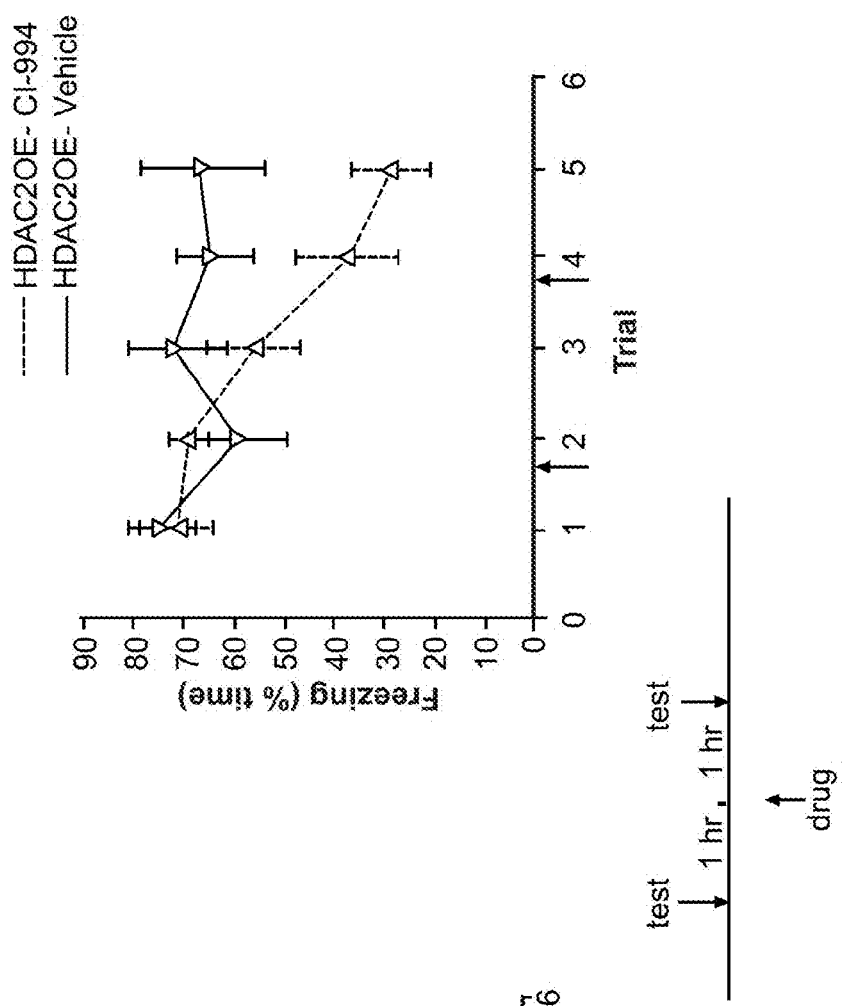
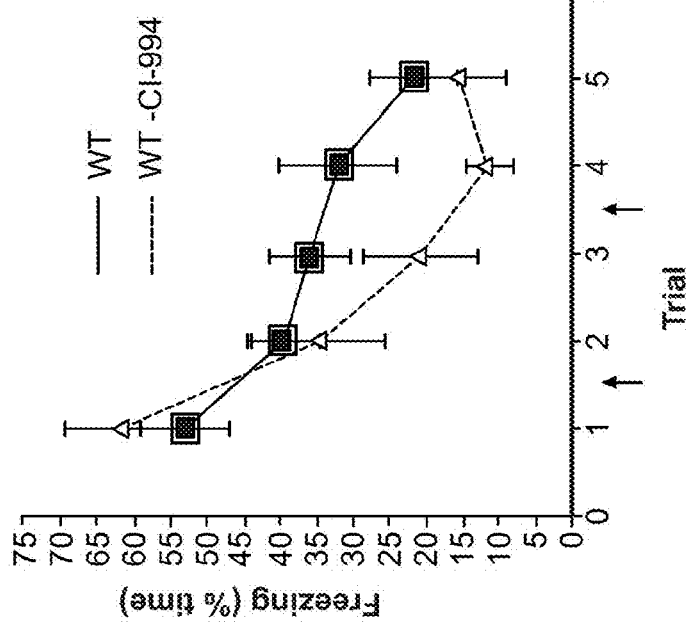
FIG. 33A
FIG. 33B
CI-994 facilitates memory formation and fear extinction. Acute dosing paradigm: 30 mg/kg, i.p. x 2 days

FIG. 38
Combined Formulation Result for CI-994 in various excipient combinations - visual inspection

- Successful formulations
    - 10% DMA+ 45% PEG400+ 45% saline or water or D5W (visual stability for 20hr);
    - 10% NMP+ 45% PEG400+ 45% saline or D5W or water (visual stability for 20hr);
    - 10% EtOH+ 45% PEG400+ 45% saline or D5W or water (visual stability for 20hr);
    - 10% DMA+ 30% Cremophor+ 60% saline or D5W (visual stability for 20hr);
    - 10% DMSO+ 30% Cremophor+ 60% saline or D5W (visual stability for 20hr)

- Potential formulations
    - 5% DMA+ 30% Cremophor+ 65% saline (visual stability for ~20min);
    - 10% DMA+ 20% Cremophor+ 70% saline (visual stability for ~10min);
    - 10% DMA+ 90% (30% HP-ß -CD water solution) (visual stability for ~30min);
    - 10% DMSO+ 40% PG+ 50% saline or D5W or water (visual stability for ~10min)

- Failed formulations
    - 5% DMA+ 95% (30% HP-ß -CD water solution);
    - 10% DMSO+ 90% (30% HP-ß -CD water solution);
    - 5% DMA+ 5% Tween 80+ 90% saline;
    - 5% DMA+ 30% PG+ 65% saline

FIG. 39

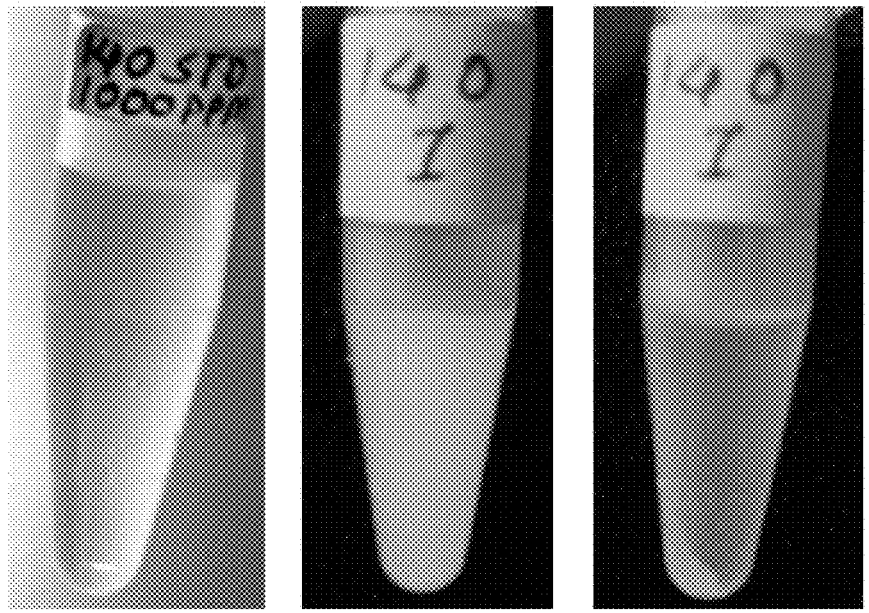

Image 1     Image 2     Image 3

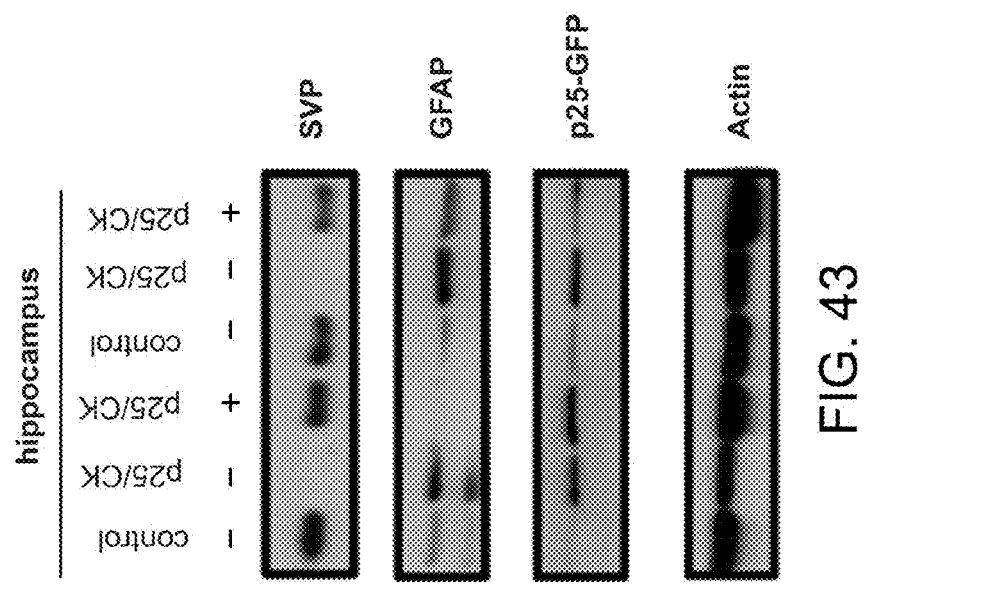
FIG. 43
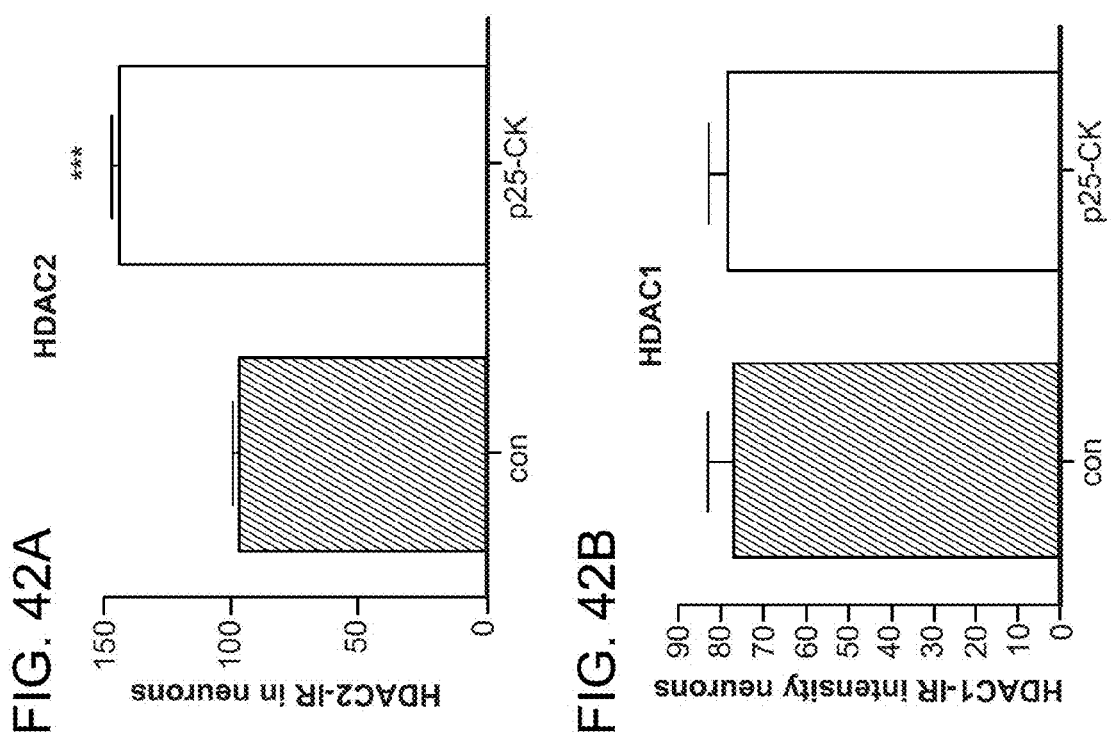
FIG. 42A
FIG. 42B

Hippocampal area C1
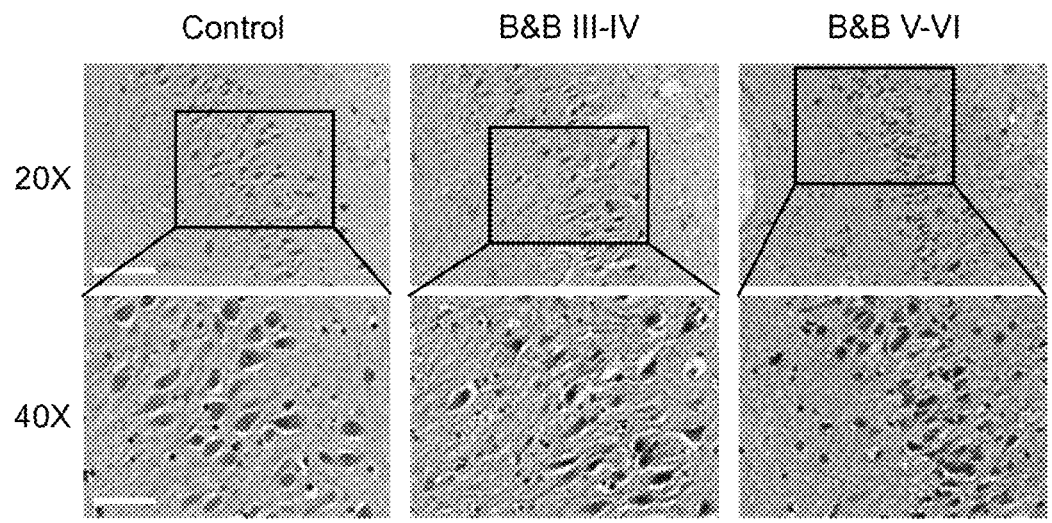
Entorhinal cotex
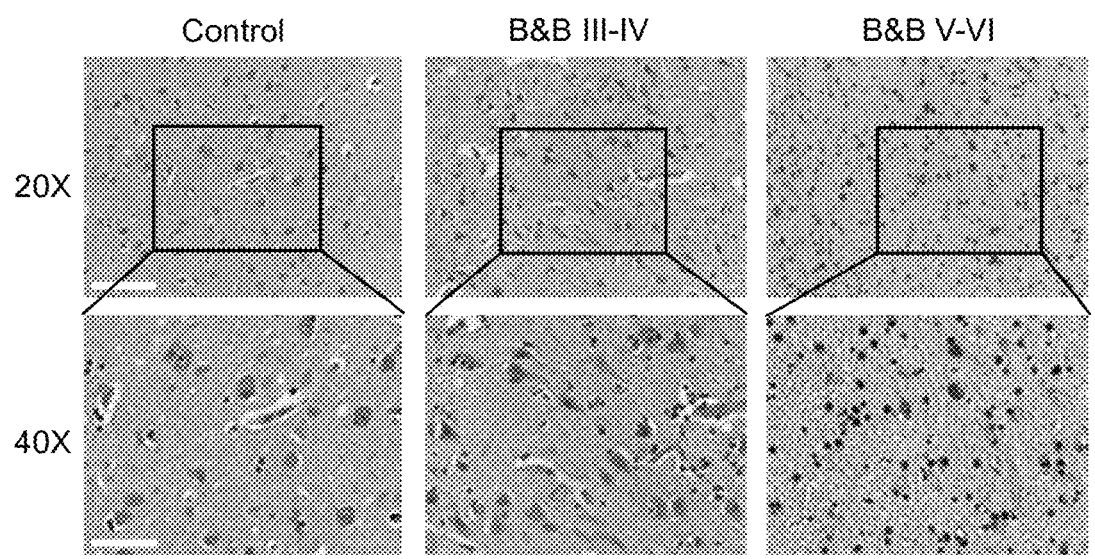
FIG. 44C

Case Details: BB, Braak and Braak stage

| Sample ID | Diagnosis | Sex | Age (years) | Postmortem Interval (hours) |
|---|---|---|---|---|
| BM9 | Control | f | 72 | 23 |
| BM11 | Control | f | 73 | 13 |
| BM17 | Control | f | 77 | 47 |
| 912 | BBIV | f | 103 | 5 |
| 1314 | Control | m | 56 | 36 |
| 1315 | BBVI | f | 64 | 9 |
| 1323 | BBIII-IV | m | 94 | 24 |
| 1325 | BB VI | f | 80 | 30 |
| 1360 | BB VI | f | 88 | 31 |
| 1368 | BB III | f | 95 | 24 |
| 1377 | BB V | m | 78 | 24 |

FIG. 44F

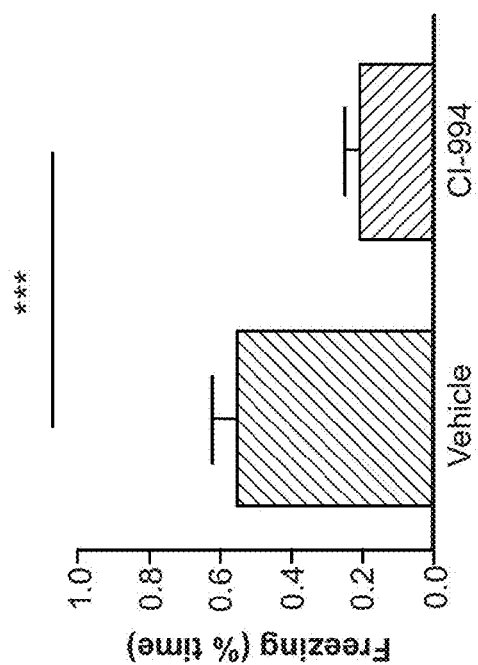
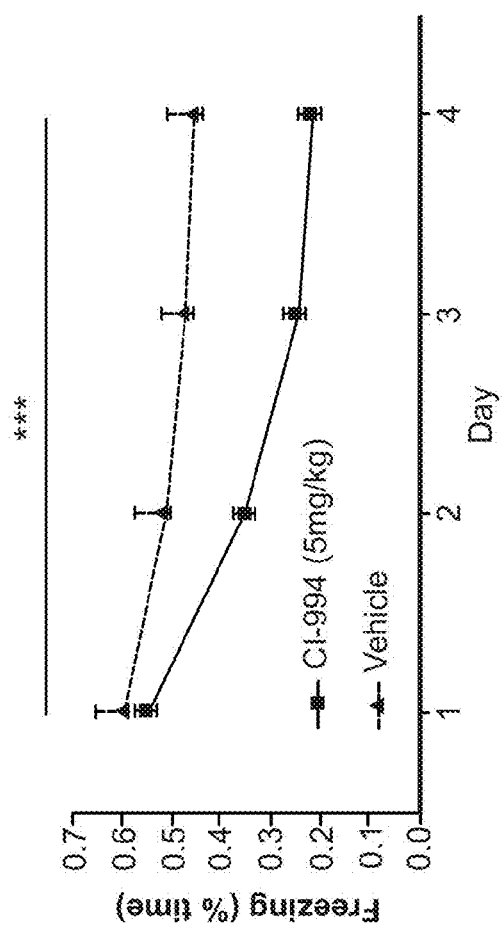

USE OF CI-994 AND DINALINE FOR THE TREATMENT OF MEMORY/COGNITION AND ANXIETY DISORDERS

RELATED APPLICATION

This application claims the benefit under 35 U.S.C. §119 (e) of U.S. Provisional Application Nos. 61/256,927, filed Oct. 30, 2009 and 61/265,468 filed Dec. 1, 2009, the entire contents of which are hereby incorporated by reference.

FIELD OF THE INVENTION

The present invention relates generally to methods and compositions for treating diseases and conditions associated with memory loss and cognitive function impairments.

BACKGROUND OF THE INVENTION

Brain atrophy occurs during normal aging and is an early feature of neurodegenerative diseases associated with impaired cognitive function and memory loss. Alzheimer's disease, Huntington's disease and other related dementias cause marked loss in cognitive function, often reducing an afflicted person to an invalid state. No cure is known for Alzheimer's disease and related dementias, and the causes of these diseases are not well understood. Moreover, pre-clinical research has not yet explored strategies to recover lost memories after substantial neuronal loss has taken place.

In eukaryotic cells, nuclear DNA wraps around a protein core consisting of histones H2A, H2B, H3, and H4 to form chromatin, with basic amino acids of the histones interacting with negatively charged phosphate groups of the DNA. Approximately 146 base pairs of DNA wrap around a histone core to make up a nucleosome particle, the repeating structural motif of chromatin. Histones are subject to posttranslational acetylation of the $\alpha,\epsilon$-amino groups of N-terminal lysine residues. The acetylation reaction is catalyzed by enzymes termed histone acetyl transferase (HATs). Acetylation neutralizes the positive charge of the lysine side chain, and is thought to impact chromatin structure in a manner that facilitates transcription (e.g., by allowing transcription factors increased access to DNA). A family of enzymes termed histone deacetylases (HDACs) has been reported to reverse histone acetylation. Eleven members of the HDAC family, termed HDAC1-HDAC11, have been reported and proposed as three distinct classes: class I, comprising HDACs 1, 2, 3 and 8, class II, comprising HDACs 4, 5, 6 and 7, and class IV, comprising HDAC 11. In vivo, the acetylation state of chromatin is thought to be maintained by a dynamic balance between the activities of HATs and HDACs. Regulating histone acetylation is an integral aspect of chromatin modulation and gene regulation that plays a critical role in many biological processes including cell proliferation and differentiation (Roth et al., 2001). Recent reports have detailed the importance of histone acetylation in CNS functions such as neuronal differentiation, memory formation, drug addiction, and depression (Citrome, 2003; Johannessen and Johannessen, 2003; Tsankova et al., 2006). However, it is not clear which of the 11 histone deacetylases is responsible for the observed CNS effects. For example, it was discovered that while HDAC1 Tg mice do not show any difference in learning behavior compared to the control mice, HDAC2 Tg mice have impaired learning as evaluated by Pavlovian fear conditioning and Morris water maze tests. Thus, HDAC 2 inhibitors are believed to enhance memory and learning. (US Published Patent Application 2008/0300205) Agents that increase HDAC1 activity are believed to be neuroprotective and may serve as agents for treatment of neurological disorders, including Alzheimer's, Parkinson's, Huntington's, Amyotrophic Lateral Sclerosis (ALS), ischemic brain damage and traumatic brain injury. (U.S. patent application Ser. No. 12/508,481 entitled: ACTIVATION OF HISTONE DEACETYLASE 1 (HDAC1) PROTECTS AGAINST DNA DAMAGE AND INCREASES NEURONAL SURVIVAL).

SUMMARY OF THE INVENTION

The invention relates, in one aspect, to the discovery of methods and compositions for promoting cognitive function and thus for the treatment of memory loss and cognitive function disorders/impairments. Accordingly, one aspect of the invention involves methods of treating cognitive function disorders or impairments in a subject in need thereof. The methods comprise administering to the subject 4-(acetylamino)-N-(2aminophenyl)benzamide (CI-994; TACEDINALINE) or a pharmaceutically acceptable salt, ester, prodrug or metabolite thereof. According to some aspects of the invention, cognitive function disorders or impairments are treated by administering to a subject in need thereof dinaline or a pharmaceutically acceptable salt, ester, prodrug or metabolite thereof.

In some embodiments, the CI-994 and dinaline are administered in combination. In some embodiments, the subject also undergoes combinational behavior therapy. The CI-994 and/or dinaline may administered at a dosage lower than 15 mg/m2 once a day for 14 consecutive days. The CI-994 and/or dinaline may be administered once a day for at least 2 consecutive days, once every other day or once a day with at least 2 days between doses. In some embodiments, the CI-994 and/or dinaline is administered in a dose of 0.001 mg/kg to 50 mg/kg for at least 2 consecutive days. In some embodiments, the CI-994 and/or dinaline is administered in a dose of up to 0.4 mg/kg for at least 14 consecutive days. In some embodiments, the CI-994 and/or dinaline is administered in a dose of 0.001 mg/kg to 50 mg/kg for at least 2, 3, 4, 5, 6, or 7 consecutive days.

According to some aspects of the invention, cognitive function disorders or impairments are treated in a subject in need thereof by administering orally, transdermally, intravenously, cutaneously, subcutaneously, nasally, intramuscularly, intraperitonealy, intracranially, or intracerebroventricularly an effective amount of 4-(acetylamino)-N-(2aminophenyl)benzamide (CI-994), dinaline or a pharmaceutically acceptable salt, ester or prodrug thereof. The cognitive function disorders/impairments may be associated with Alzheimer's disease, Huntington's disease, seizure-induced memory loss, schizophrenia, Rubinstein Taybi syndrome, Rett Syndrome, Fragile X, Lewey body dementia, Vascular dementia, bipolar disorder and social, cognitive and learning disorders associated with autism, traumatic head injury, or attention deficit disorder. In some embodiments, the cognitive function disorders/impairments are associated with anxiety disorders, conditioned fear response, panic disorders, obsessive compulsive disorders, post-traumatic stress disorder, phobias, social anxiety disorders, or substance dependence recovery. In some embodiments, the subject may be exposed to psychotherapy, behavioral exposure treatments, virtual reality exposure (VRE) or cognitive remediation therapy.

According to some aspects of the invention, methods of treating Alzheimer's disease are provided. The methods comprise administering to the subject 4-(acetylamino)-N-(2-aminophenyl)benzamide (CI-994) or a pharmaceutically acceptable salt, ester, prodrug or metabolite thereof, wherein the CI-994 is administered at a dosage effectively low to maintain a cumulative effective CI-994 serum concentration. According to some aspects of the invention, Alzheimer's disease is treated in a subject by administering dinaline or a pharmaceutically acceptable salt, ester, prodrug or metabolite thereof wherein the dinaline is administered at a dosage effectively low to maintain a cumulative effective dinaline serum concentration. In some embodiments, the dinaline is administered once every other day.

According to some aspects of the invention, methods of treating Huntington's disease are provided. The methods comprise administering to the subject an effective amount of CI-994, dinaline or pharmaceutically acceptable salts, esters, prodrugs or metabolites thereof. The CI-994 and/or dinaline may be administered once every other day. In some embodiments, the CI-994 and/or dinaline may be administered orally, transdermally, nasally or intraperitonealy. The method of treatment may be selected based on medical history, family history or brain imaging tests. In some embodiments, the method of treatment is not selected based on expression levels of Huntington disease biomarker genes selected from the group consisting of ANXA1, AXOT, CAPZA1, HIF1A, JJAZ1, P2Y5, PCNP, ROCK1 (p160ROCK), SF3B1, SP3, TAF7 and YIPPEE.

According to some aspects of the invention, methods of improving cognitive function in a normal subject are provided. The methods comprise administering to the subject an effective amount of CI-994, dinaline or pharmaceutically acceptable salts, esters, prodrugs, or metabolites thereof. In some embodiments, the CI-994 or dinaline is administered at a dosage lower than 15 mg/m$^2$ once a day for 14 consecutive days. In some embodiments, the CI-994 and/or dinaline is administered at a dosage of 1 mg/kg once a day for 10 consecutive days. The CI-994 or dinaline may be administered once every other day, or once a day with at least 2 days between doses. The CI-994 or dinaline may be administered to the subject orally, transdermally, intravenously, cutaneously, subcutaneously, nasally, intramuscularly, intraperitonealy, intracranially, or intracerebroventricularly.

According to some aspects of the invention, methods of promoting fear extinction in a subject are provided. The methods comprise administering to the subject an effective amount of CI-994, dinaline or pharmaceutically acceptable salts, esters, prodrugs or metabolites thereof. The CI-994 or dinaline may be administered once every other day. Routes of administration include oral, transdermal, nasal and intraperitoneal.

In other aspects, the invention is a method for promoting fear extinction in a subject by administering to the subject 4-(acetylamino)-N-(2-aminophenyl)benzamide (CI-994) or dinaline or a pharmaceutically acceptable salt, ester, prodrug or metabolite thereof before exposure to a fear associated context. The CI-994 or dinaline may be administered 1-3 hours prior to the exposure to the fear associated context in some embodiments. In other embodiments the subject is provided with only a single administration of CI-994 or dinaline. The exposure to the fear associated context may be in a reconsolidation paradigm.

Some aspects of the invention relate to compositions comprising CI-994, dinaline or pharmaceutically acceptable salts, esters, prodrugs or metabolites thereof. The compositions may be formulated for oral, transdermal, intravenous, cutaneous, subcutaneous, nasal, intramuscular, intraperitoneal, intracranial, or intracerebroventricular administration. The composition may comprise 4-(acetylamino)-N-(2-aminophenyl)benzamide (CI-994) or a pharmaceutically acceptable salt, ester, prodrug or metabolite thereof formulated in a dosage of lower than 0.001 mg/kg to 50 mg/kg once a day for at least 2, 3, 4, 5, 6, or 7 consecutive days. In some embodiments, the CI-994 and/or dinaline is administered in a dose of 0.001 mg/kg to 15 mg/kg for at least 2 consecutive days. In some embodiments, the CI-994 and/or dinaline is administered in a dose of up to 15 mg/kg for at least 14 consecutive days. In some embodiments, the CI-994 and/or dinaline is administered in a dose of 0.04 mg/kg. The compositions may be formulated in a dosage of lower than 15 mg/m$^2$ once a day for 14 consecutive days. Some aspects of the invention relate to a kit comprising a container housing an effective amount of 4-(acetylamino)-N-(2-aminophenyl)benzamide (CI-994) or a pharmaceutically acceptable salt, ester prodrug or metabolite thereof formulated for oral, transdermal, intravenous, cutaneous, subcutaneous, nasal, intramuscular, intraperitoneal, intracranial, or intracerebroventricular for enhancing cognitive function and instructions for administering the CI-994 to a subject in need of cognitive enhancement.

Compositions comprising a HCL salt of CI-994 are also contemplated within the scope of the invention. In some embodiments, the salt of CI-994 has the following chemical structure:

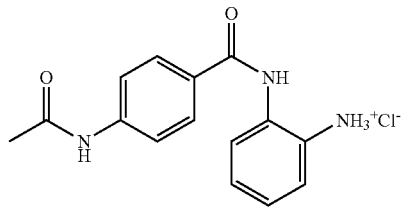

CI-994
HCl salt
Chemical Formula:
$C_{15}H_{16}ClN_3O_2$
Molecular Weight: 305.76

According to some aspects of the invention, a salt of 4-(acetylamino)-N-(2-aminophenyl)benzamide (CI-994) having a crystalline form is provided. According to some aspects of the invention, compositions comprising 4-(acetylamino)-N-(2-aminophenyl)benzamide (CI-994) in a formulation are provided. The formulation may comprise a) 5-15% of a compound selected from the group consisting of DMA, NMP, EtOH, and DMSO; b) 25-50% of a compound selected from the group consisting of PEG400, cremophor and HP-β and c) 0-70% of a compound selected from the group consisting of saline, water and D5W. Different embodiments of the formulation include: 10% DMA, 45% PEG400, and 45% saline or water or D5W; 10% DMA, 45% PEG400, and 45% saline or water or D5W; 10% EtOH, 45% PEG400, and 45% saline or water or D5W; 10% DMA, 30% cremophor, and 60% saline or water or D5W; 10% DMSO, 30% cremophor, and 60% saline or water or D5W; 5% DMA, 30% cremophor, and 65% saline or water or D5W; 10% DMA, 20% cremophor, and 70% saline or water or D5W; 10% DMA and 90% HP-b-CD water solution and 10% DMSO, 40% PG, and 50% saline or water or D5W.

According to some aspects of the invention, methods of treating cognitive function disorders or impairments in a subject in need thereof are provided. The method comprises administering to the subject 4-(acetylamino)-N-(2aminophenyl)benzamide (CI-994) in a dose of 0.1-1.0 mg/kg or a pharmaceutically acceptable salt, ester, prodrug or metabolite thereof. In some embodiments, the CI-994 is administered at the dose of 01.-1.0 mg/kg once per day for at least 10 consecutive days.

According to some aspects of the invention, methods of treating cognitive function disorders or impairments in a subject in need thereof are provided. The method comprises administering to the subject 4-(acetylamino)-N-(2aminophenyl)benzamide (CI-994) in a dose of 0.001-50.0 mg/kg or a pharmaceutically acceptable salt, ester, prodrug or metabolite thereof. In some embodiments, the CI-994 and/or dinaline is administered in a dose of 0.001 mg/kg to 15 mg/kg for at least 2 consecutive days. In some embodiments, the CI-994 and/or dinaline is administered in a dose of up to 15 mg/kg for at least 14 consecutive days. In some embodiments, the CI-994 and/or dinaline is administered in a dose of 0.04 mg/kg. In some embodiments, the CI-994 is administered at the dose of 0.1-1.0 mg/kg once per day for at least 10 consecutive days. In some embodiments, the CI-994 is administered once per day once a day for at least 2, 3, 4, 5, 6, or 7 consecutive days.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

The figures are illustrative only and are not required for enablement of the invention disclosed herein.

FIG. 1 shows the enzymatic inhibitory activity of CI-994 and dinaline. Both compounds are primarily Class I HDAC inhibitors. FIG. 1A shows the time dependent enzymatic inhibitory activity of CI-994 and dinaline. Both compounds are primarily Class I HDAC inhibitors.

FIG. 2 shows the decreased in histone acetylation marks in Rubinstein Taybi CBP$^{+/-}$ mice. Immunostaining of sagittal brain sections of Rubinstein Taybi CBP$^{+/-}$ mice using antibodies revealed a decreased level of AcH2B in hippocampal neurons (FIG. 2A). Western blot analysis of hippocampal protein extracts from CBP$^{+/-}$ and WT mice using antibodies against β-actin, H2B (nonacetylated), AcH2A, AcH3 and AcH4 revealed a similar decrease in AcH2B level (FIG. 2B). Quantification of Western blot analysis showed no differences in the level of β-actin, total H2B, AcH2A, AcH3, but a significant difference in the level of AcH2B. A similar reduction in H2B acetylation was also observed using another AcH2B antibody (FIG. 2C).

FIG. 14. The graph demonstrates that CI-994 treatment activates a TCF/LEF luciferase reporter gene in human neural progenitor cells with an EC50 of ~7 uM. CI-994 shows strong synergistic effects on the TCF/LEF reporter when combined with Wnt conditioned media with the same EC50, but a significantly higher level of activation. These potencies are consistent with the potency observed for histone acetylation.

FIG. 19 shows that acute treatment with CI-994 increases H4K5 histone acetylation in whole brain. A. CI-994 was formulated in several different excipient combinations and dosed at 30 mg/kg via intraperitoneal injection. At 1 h post dose, whole brains were fixed and analyzed via western blot analysis for the effects on H4K5 acetylation. B. The quantified histograms demonstrate that CI-994 when formulated in either 5% DMSO/30% Cremophor/65% saline or 10% DMA/30% Cremophor/60% saline causes changes in the brain histone acetylation levels. DMSO—Dimethyl sulfoxide; DMA—Dimethylacetamide.

FIG. 21 shows the experimental protocol for acute treatment with CI-994 and the corresponding effects on histone acetylation in brain specific regions of adult male C57BL/6J mice. The experiments were performed using a series of HDAC inhibitors that were dosed according to the protocol shown in the figure—acute dosing, systemic administration followed by specific brain region dissection and fixation to examine histone acetylation changes caused by the different compounds. Changes in histone acetylation levels would be consistent with the functional activity of an HDAC inhibitor. Therefore, these experiments help demonstrate that CI-994 has entered the brain, and the nucleus of cells located in specific brain regions associated with learning and memory. Moreover, CI-994 causes an increase in specific acetylation marks which have also been associated with learning and memory effects.

FIG. 22 demonstrates that acute treatment with CI-994 causes a significant increase in the levels of tetra-acetylated H4 and H2B in the cortex of mice. The histograms shown in panel A are the quantification of the Western gel data shown in panel B. The data was normalized to the level of histone H3 levels. CI-994 caused a 2 fold increase in cortex for both of these marks. This demonstrates that CI-994 is a functional inhibitor of HDACs in the cortex.

FIG. 32 demonstrates that HDAC2 overexpression mice were impaired in extinction of fear memory compared to WT control mice. A. The graph shows that mice which overexpress HDAC1 exhibit normal extinction. B. HDAC2 overexpressing mice are unable to extinguish the conditioned fear response.

FIG. 33 demonstrates that CI-994 facilitates memory formation and fear extinction with an acute dosing paradigm. A. In wild type mice, there is little difference between CI-994 treated vs untreated. B. HDAC2 overexpressing mice treated with 2 doses (acute treatment paradigm) of CI-994 demonstrate improved memory formation and fear extinction. Significant improvement was seen relative to the untreated HDAC2 overexpressing mice.

FIG. 38 shows the combined formulation result for CI-994 in various excipient combinations.

FIG. 39 shows the images of CI-994 HCl salt solutions.

FIG. 42 shows the expression of HDAC1 and HDAC2 in the cortex of p25 mice. A. Quantification of HDAC2 immunoreactivity intensity in cortical neurons. (>600 neurons from 3 mice were quantified.) B. Quantification of HDAC1-IR intensity in cortical neurons. (>500 neurons from 3 mice were quantified).

FIG. 43 demonstrates that CI-994 treatment (1 mg/kg, i.p.) increased synaptophysin (SVP) expression in CK-p25 mice.

FIGS. 44C-E demonstrate the human Alzheimer's brain is characterized by increased levels of the histone deacetylase HDAC2. FIG. 44C shows representative immunohistochemistry images of HDAC2 in paraffin-embedded sections of hippocampal area CA1 and entorhinal cortex of control brains, cases with mild Alzheimer's Disease (Braak and Braak (B&B) stage III-IV) and cases with severe Alzheimer's Disease (B&B stage V-VI). Scale bar=0.7 mm for upper panels, 0.35 mm for lower panels. D. Quantification of HDAC2 levels in area CA1 of control (n=4), B&B III-IV (n=3) and B&B V-VI (n=4) brains, F2, 8=4.495, p<0.05. E. Quantification of HDAC2 levels in the entorhinal cortex (EC) of control (n=4), B&B III-IV (n=3) and B&B V-VI (n=4) brains, F2, 8=4.988, p<0.05. FIG. 44F provides case details—BB stages III-IV represent patients with so-called "mild" Alzheimer's Disease, which is characterized by mild to progressive memory loss and noticeable decreases in cognitive functions; BB stages V-VI represent patients with so-called "severe" Alzheimer's Disease, characterized by severe memory loss and dementia, loss of motor skills and delusions.

FIGS. 49A-H shows that CI-994 efficiently and persistently extinguishes traumatic long-term memories.

DETAILED DESCRIPTION

Figure 3:
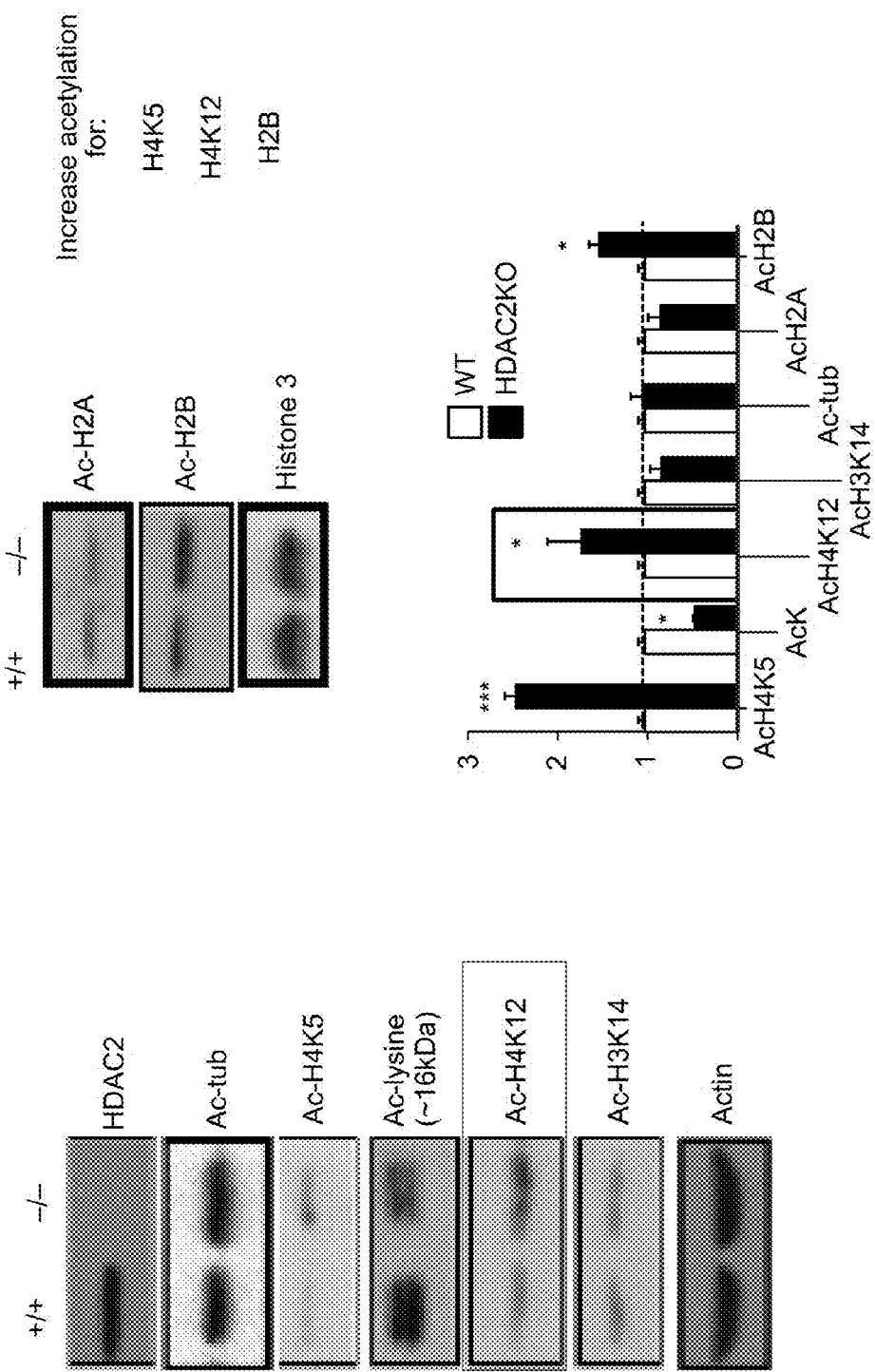
FIG. 3 shows increased histone acetylation marks (H4K5, H4K12 and H2B) associated with HDAC2 knock out in mouse brain. Histone acetylation marks associated with HDAC2 knockout mice were analyzed using Western blot.
Figure 4:
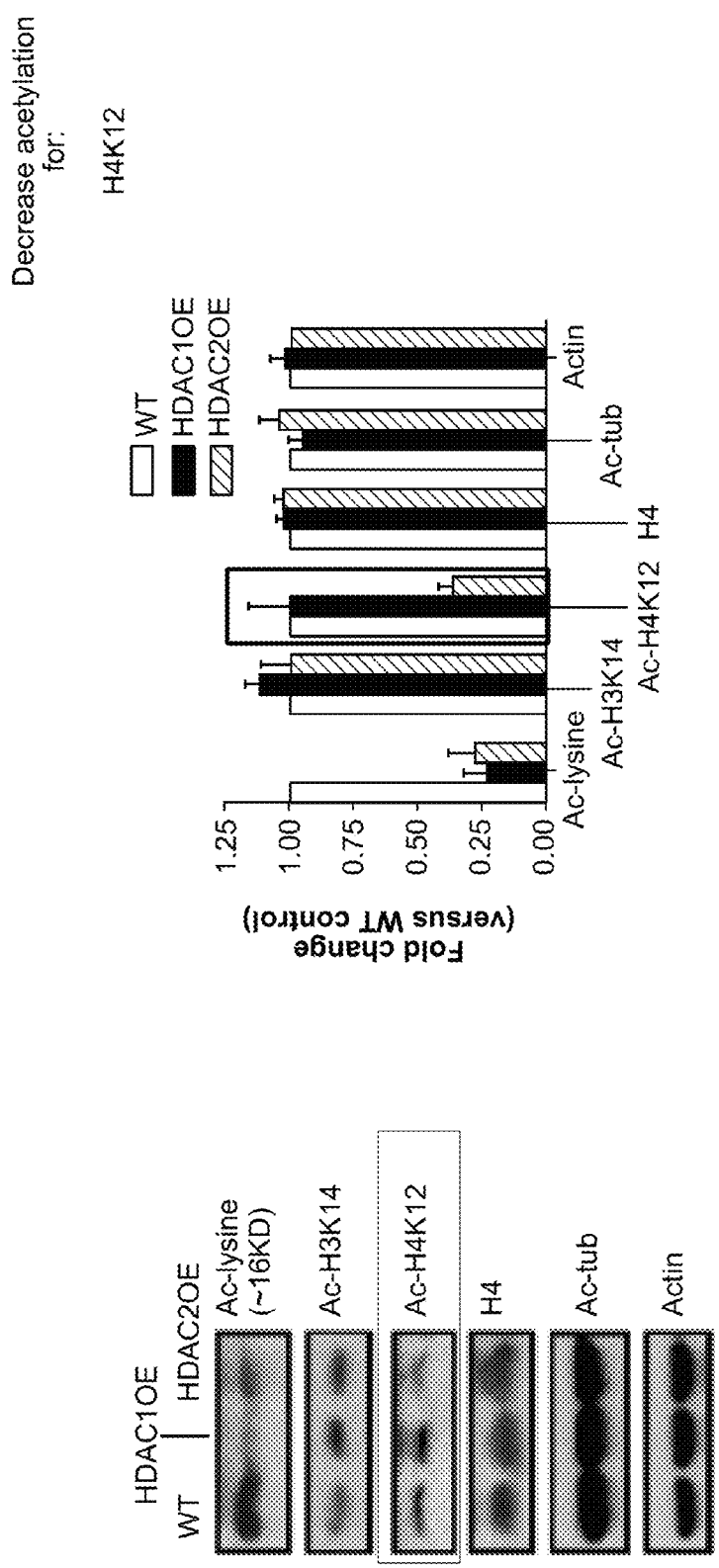
FIG. 4 shows decreased histone acetylation mark (H4K12) associated with HDAC2 overexpression in mouse brain. H4K12 is a key histone mark associated with the function of HDAC2. Histone acetylation marks associated with HDAC2 overexpression mice were analyzed using Western blot.
Figure 5:
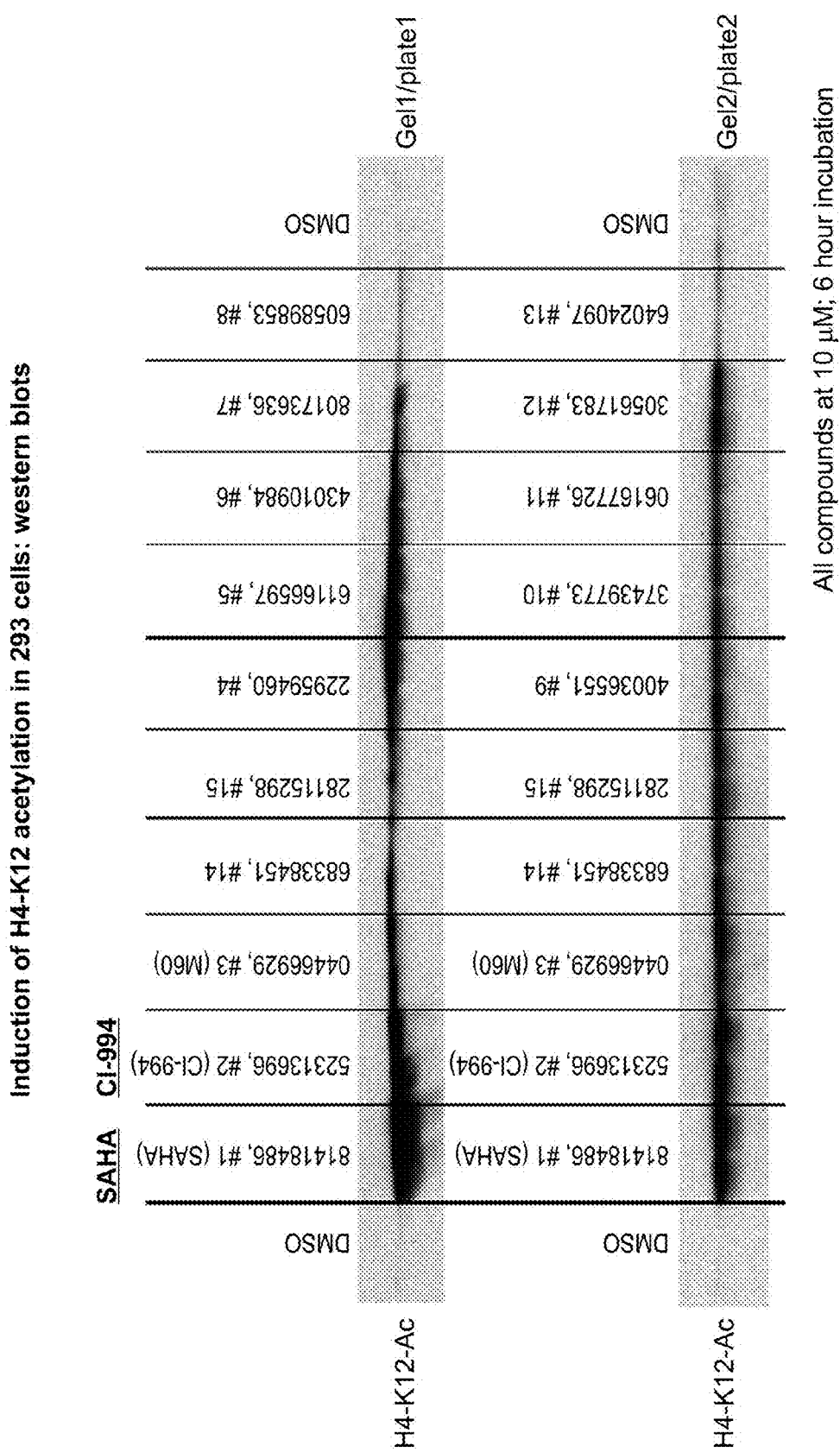
FIG. 5 shows the effects of HDAC inhibitors on histone acetylation marks in HEK293 cells. Series of compounds including SAHA and CI-994, were incubated with whole HEK293 cells at 10 uM for a 6 hour time period. Western blot analysis showed increased acetylation levels over DMSO controls using anti-acetyl H4K12 antibodies and horseradish peroxidase conjugated secondary antibody along with a luminol-based substrate. This demonstrates cellular HDAC activity of CI-994 and the increase in acetylation in the specific mark, H4K12.
Figure 6:
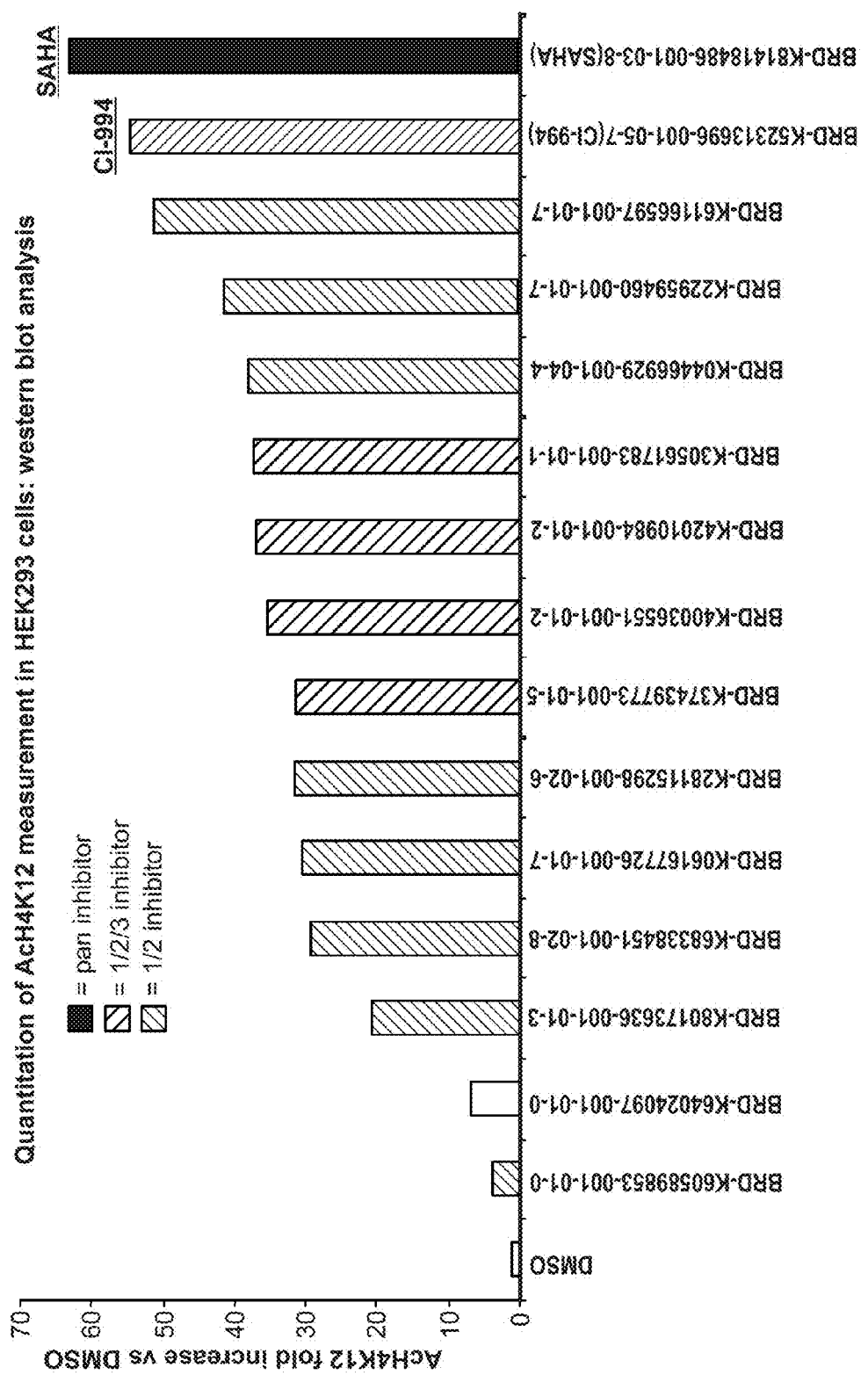
FIG. 6 is the quantification of the raw western data shown in FIG. 5. Relative to the DMSO control, CI-994 increases H4K12 acetylation levels by more than 50 fold. This demonstrates the robust HDAC activity of CI-994 in whole cells and the effect of CI-994 on a specific histone loci (H4K12).
Figure 7:
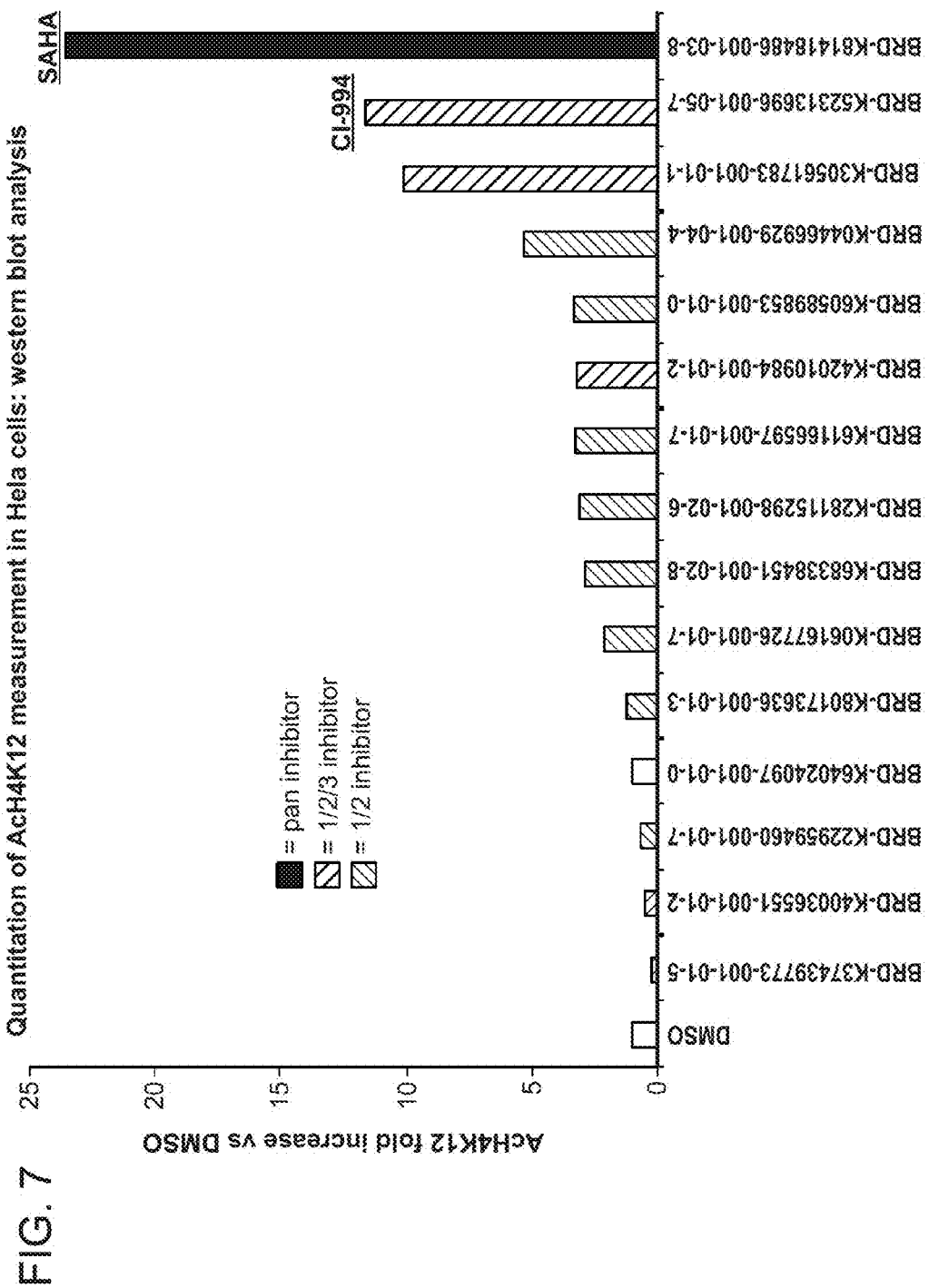
FIG. 7 is the quantification of the raw western blots used to measure the effects of HDAC inhibitors on histone acetylation marks in HeLa cell lysate. A series of compounds were profiled and CI-994 and SAHA are highlighted. Relative to the DMSO control, CI-994 increases H4K12 acetylation levels by more than 10 fold. This histogram demonstrates the robust HDAC activity of CI-994 in whole cells and the effect of CI-994 on the specific histone loci (H4K12).
Figure 8A:
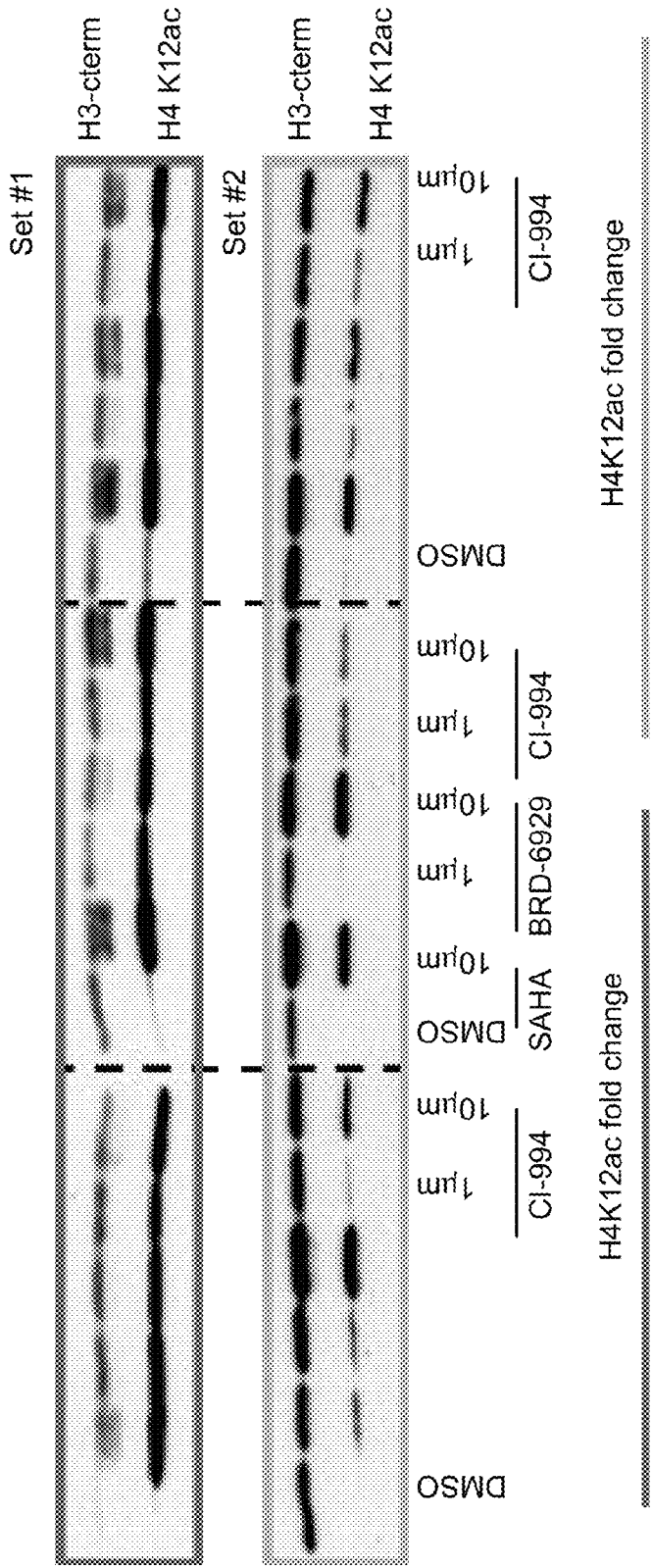
FIG. 8 shows the increased H4K12 acetylation marks in mouse primary striatal cells. A. Western blots of primary striatal cells isolated from mouse brain that have been treated with HDAC inhibitors. 2 sets with 3 independent samples per set are shown. B. The histograms represent the quantification of westerns shown in FIG. 8A. Relative to DMSO controls, CI-994 has a significant effect on the acetylation levels of histone loci H4K12. CI-994 treatment results in a 5 fold increase at 1 and 10 uM.
Figure 8B:
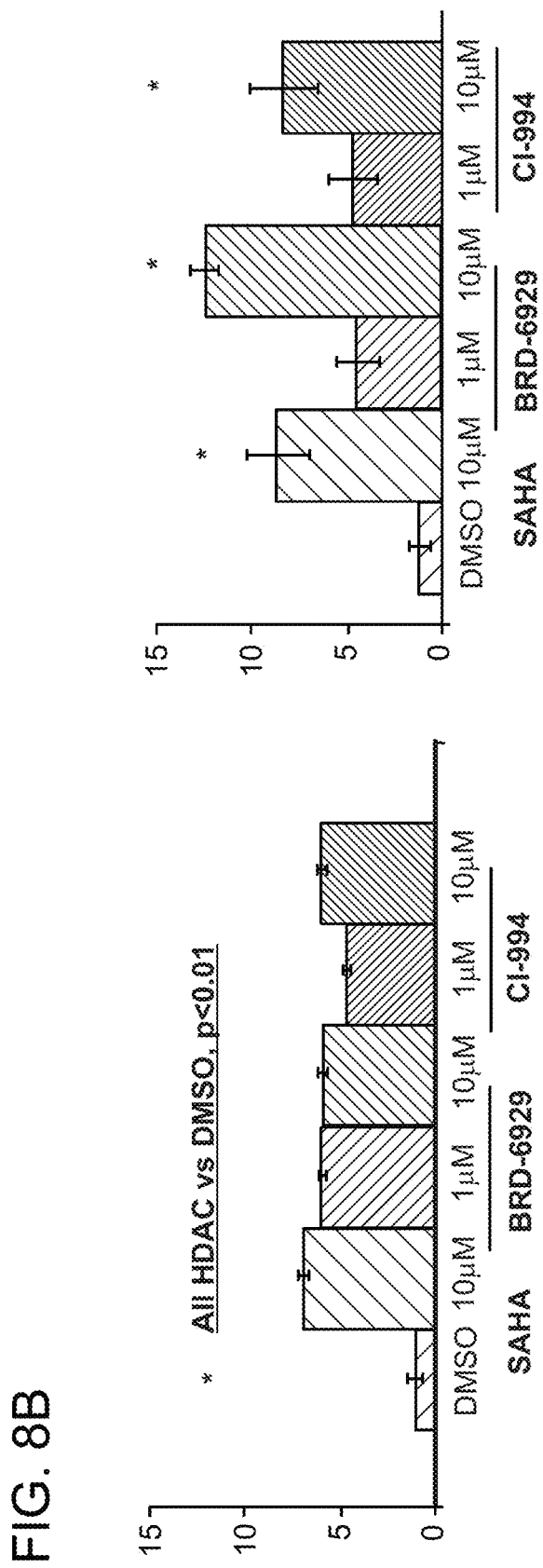
Figure 9:
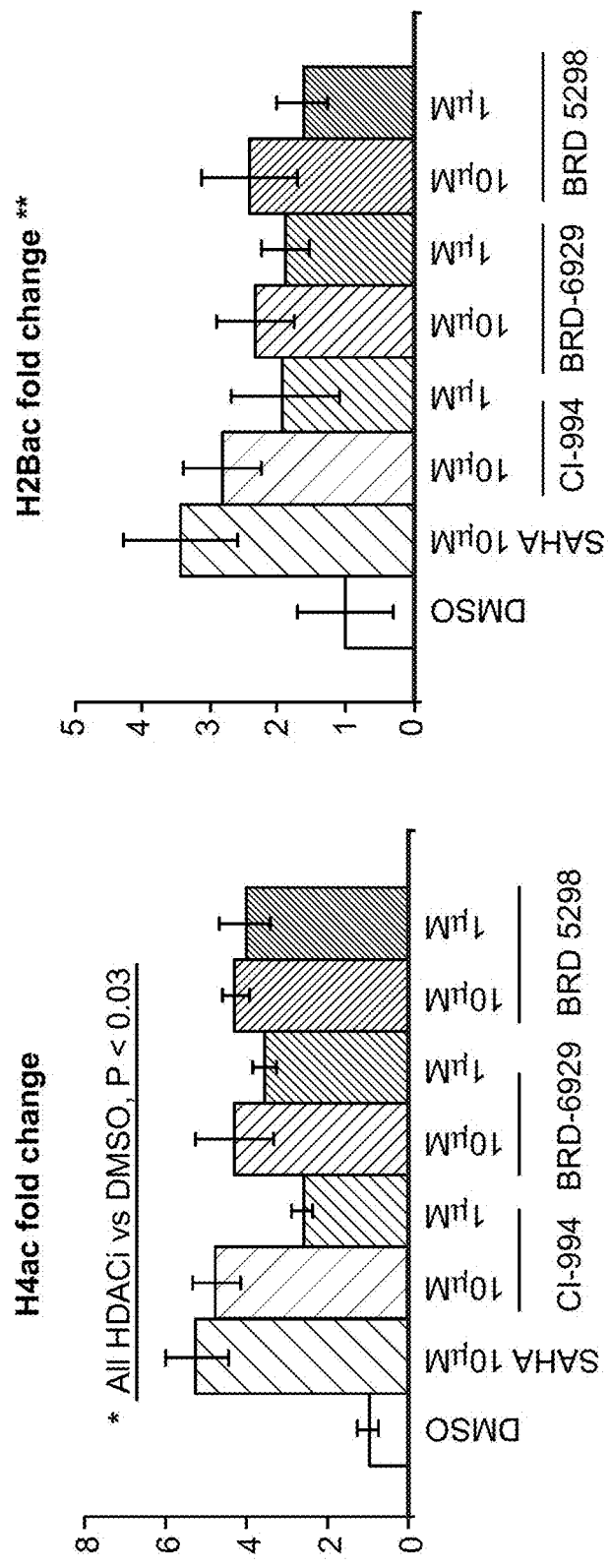
FIG. 9 shows that treatment of neuronal cells with CI-994 enhances H4 and H2B histone acetylation in vitro. The histograms represent the quantification of western gel analysis examining additional acetylation marks in primary striatal cells. Three compounds were tested including CI-994 and SAHA. Relative to DMSO controls, CI-994 has a significant increased tetra-acetylated H4 and tetra-acetylated H2B. CI-994 treatment results in a 2-5 fold increase in both marks at 1 and 10 uM.

The invention relates, in one aspect, to the discovery of methods and compositions for promoting cognitive function and thus for the treatment of memory loss and cognitive function disorders/impairments. Accordingly, one aspect of the invention, involves methods of treating cognitive function disorders/impairments by administering to a subject in need thereof an effective amount of the HDAC inhibitor 4-(acetylamino)-N-(2-aminophenyl)benzamide (CI-994), its metabolite dinaline or pharmaceutically acceptable salts, esters, or prodrugs thereof. Surprisingly it has been discovered according to the invention that CI-994 and its metabolite improve cognitive function in vivo, when other HDAC inhibitors, even some having similar structures, do not function in this manner in vivo. It was quite unexpected that CI-994 demonstrated dramatic in vivo efficacy when other HDAC inhibitors that appeared more promising in in vitro assays failed to achieve the same results on cognitive function.

As shown in the Examples below, using enzymatic binding assays on 10 recombinant human HDAC isoforms (selectivity and potency) it was discovered that the compounds useful according to the invention are predominately Class I HDAC inhibitors. However, it was also discovered that the binding profile alone is not sufficient to determine if a compound will show an improvement in cognitive function in vivo. For instance several compounds that are HDAC I inhibitors were found to not result in improved memory assays in vivo. For example MS-275, MGC-D0103, and apicidin did not result in improved cognition. The data demonstrate that several chemical classes of HDAC inhibitors are ineffective at increasing the memory of mice as measured by % freezing in a contextual fear conditioning paradigm. It was not obvious which compounds would be efficacious based on their ability to inhibit the HDAC enzyme in vitro. More importantly, this data shows that other compounds from the same benzamide chemical class as CI-994 (MS-275 and MGCD0103) are not efficacious in this model under these conditions. In contrast to these other molecules a dose ranging from 1-30 mg/kg of CI-994 given every day for 10 days improves the memory of mice in a contextual fear conditioning paradigm as measured by % time. It was not obvious that this compound or this class would be efficacious based on the data shown on the previous page.

Not only is CI-994 effective in this model of memory using an every day for 10 days dosing paradigm, it is equally effective using an alternate day dosing schedule at the 1 mg/kg and 30 mg/kg dose. As shown in the data the effective total dose was lowered by 50% and efficacy was retained. It was also discovered that even at low doses administered systemically there are significant levels of CI-994 in brain and plasma for producing in vivo effects. A single dose of 1 mg/kg CI-994 administered systemically via intraperitoneal injection produced effective concentrations. It was not obvious what the necessary exposure requirements in the brain are that correlate with a behavioral phenotype associated with improved memory. It is demonstrated herein, quite surprisingly that CI-994 at low doses and exposure is just as effective as doses and exposures that are 20-30 fold higher. As shown in the Examples a concentration time curve in mouse brain after a single dose at 30, 10 and 1 and 0.1 mg/kg CI-994 administered systemically via intraperitoneal injection was generated. Brain exposure is dose proportional across these dose levels. All four exposure profiles were shown to be efficacious in subsequent in vivo models of memory. It was not obvious that this dosing paradigm should be effective and what the optimal dosing schedule is. It is believed that an efficacious every other day dosing schedule with CI-994 or any other HDAC inhibitor has not been reported. It was not obvious that this dosing schedule would work with CI-994, that this schedule could be extended to other members of this chemical class of HDAC inhibitors or with other chemical classes of HDAC inhibitors.

It has also been demonstrated experimentally that CI-994 has entered the brain, and the nucleus of cells located in specific brain regions associated with learning and memory. Moreover, CI-994 causes an increase in specific acetylation marks which have also been associated with learning and memory effects.

It was also discovered according to the invention that CI-994 could be modified into a salt form that has a dramatic effect on solubility. As shown in the Examples below the HCl salt form of CI-994 has a 35 times greater solubility than CI-994 in an aqueous solution. HPLC analysis confirmed the chemical and solution stability of the HCl salt form of CI-994 for a minimum of 2 hours. This salt formulation is suitable for use in the delivery of CI-994 without the use of other excipients. Such findings were quite unexpected.

Additionally, several formulations that were able to improve the solubility of CI-994 were discovered according to the invention. The claimed formulations are stable (chemical and solution) 5 mg/ml solution formulations which include organic solvents and a broad array of pharmaceutically acceptable excipients. These formulations in some instances demonstrated a 62 times improvement over the 2 hour solubility of the CI-994 free base in saline alone.

In some embodiments, methods of treating Alzheimer's disease are provided. For example the data shown herein demonstrate that at a low dose of 0.1 mg/kg dosed every day for 10 days, CI-994 is able to rescue the cognitive defects in this mouse model of Alzheimer's. It was quite unexpected that such a low dose would be effective in this model. In some embodiments, subjects having impaired cognitive function and substantial neuronal loss are treated. Some aspects of the invention relate to methods of improving cognitive function in a normal subject.

It has also been discovered surprisingly according to the invention that the compounds described herein are useful in fear extinction. Fear extinction is the decrease in conditioned fear responses that normally occurs when a conditioned stimulus (CS) is repeatedly presented in the absence of the aversive unconditioned stimulus (US). Extinction does not erase the initial CS-US association, but is thought to form a new memory. Deficits in fear extinction are thought to contribute to post-traumatic stress disorder (PTSD), phobias, anxiety disorders, etc. The fear extinction behavioral paradigm is recognized as a model for human stress disorders and phobias. Importantly, extinction is not simply forgetting but involves new inhibitory learning (Myers and Davis, 2002). The data presented below demonstrates that mice that overexpress HDAC1 exhibit normal extinction. The HDAC2 overexpressors are unable to extinguish the conditioned fear response. Conversely, fear extinction is faciliated in HDAC2 loss of function mice. CI994, a chemical that inhibits HDAC1, 2 and 3, when administered into mice, faciliated extinction of fear memory. In wild type mice there is little difference between CI-994 treated vs untreated. However, HDAC2OE mice treated with 2 doses (acute treatment paradigm) of CI-994 demonstrated improved memory formation and fear extinction. The results are significant and surprising. This data demonstrates that CI-994 is effective in another distinct form of memory formation. Additionally, CI-994 is effective in an acute dosing setting. The rescue of the HDAC2 OE was achieved with 2 doses of CI-994 over the course of 5 days.

Much of the research on fear extinction involves the normal extinction paradigm. Recently a reconsolidation paradigm has been described. See for instance, Monfils et al Science, 324, p. 951, 2009 and Schiller et at Nature, 463, p. 49, 2010. The reconsolidation paradigm involves a phase in which memories become labile for a period of time after being retrieved. Manipulation of the memory, by pharmacological intervention or presentation of non-fearful memories, during the critical window, referred to as the reconsolidation window, can cause the old memory to be re-updated with non-fearful information, thus lessening the fear experienced by the subject upon memory recall. The reconsolidation paradigm is believed to be more relevant to human therapy.

Figure 52:
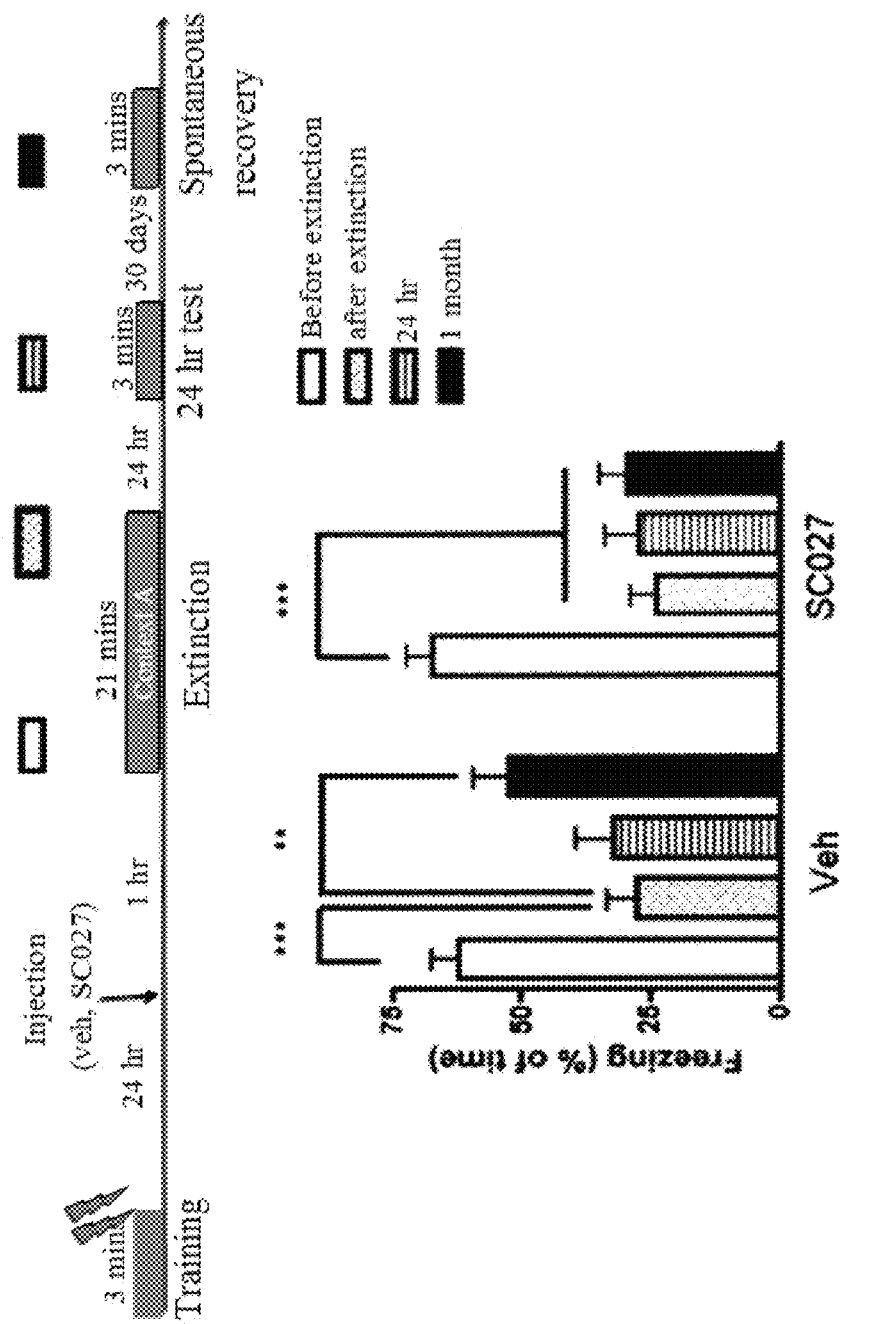
FIG. 52 shows that CI-994 facilitated fear extinction under the reconsolidation paradigm, even when the first exposure of the memory reconsolidation paradigm is eliminated.
Figure 53:
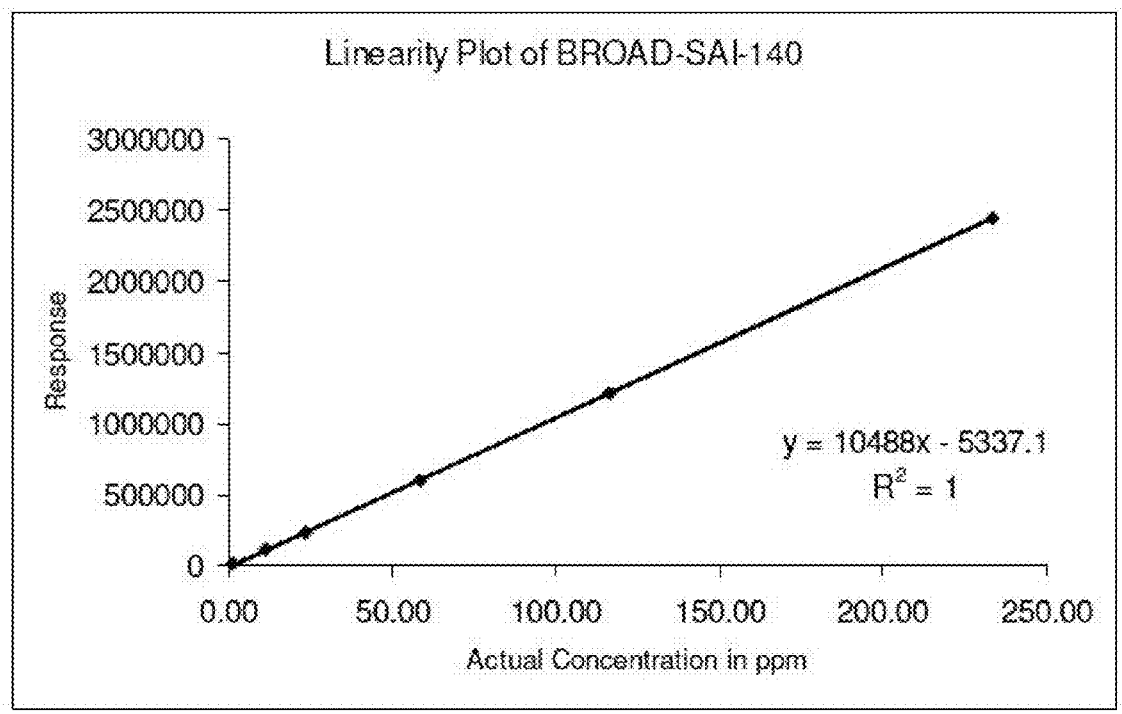
FIG. 53 shows the linearity plot of BROAD-SAI-140.

It was discovered herein that CI-994 was useful for fear extinction using the normal extinction paradigm. CI-994 functioned similar to D-cycloserine, which is known to be useful in promoting fear extinction. Surprisingly, it was discovered herein that in the reconsolidation paradigm, which appears to be more relevant to humans, CI-994 was significantly more effective than D-cycloserine (FIG. 48). Even more surprisingly, it was discovered that CI-994 can replace the first exposure of the memory reconsolidation paradigm to extinguish fear memory (FIG. 48 and FIG. 52). These discoveries, which were unexpected, support the finding that CI-994 is beneficial in therapeutic fear extinction.

Thus, the invention involves in some embodiments administering to a subject CI-994 before exposure to a fear associated context. A fear associated context is a cue that triggers the fear. A fear associated context may be, for instance, a therapy session that recalls the original triggering event, a later safe event that triggers a fear based on the original triggering event, or some other cue that triggers a fear based on the original triggering event, such as in a research, an environmental cue that is associated with the triggering event. The CI-994 should be administered such that it is effective during the reconsolidation phase. For example it could be administered within 10 hours of the exposure to the fear associated context. In some embodiments it is administered within 6 hours, within 5 hours, within 4 hours, within 3 hours, within 2 hours, within 1 hour of the fear associated context. In other embodiments it is administered 1-3 hours before the fear associated context or any time therebetween.

The subject may be administered multiple doses of CI-994 per therapy session. Alternatively the subject may be administered only a single dose of CI-994 per therapy session. Some subjects will only require a single therapy session/CI-994 treatment to develop long term fear extinction, whereas others may require multiple sessions, sometimes set several weeks or months apart in time in order produce therapeutic extinction. The amount of therapy session required may depend on the severity and extent of the fear requiring extinction.

A "memory" as used herein refers to the ability to recover information about past events or knowledge. A subject having memory loss is a subject that cannot recall one or more memories. Memories include short-term memory (also referred to as working or recent memory) and long-term memory. Short-term memories involve recent events, while long-term memories relate to the recall of events of the more distant past. Methods for assessing the ability to recall a memory are known to those of skill in the art and may include routine cognitive tests.

"Cognitive function" refers to mental processes of an animal or human subject relating to information gathering and/or processing; the understanding, reasoning, and/or application of information and/or ideas; the abstraction or specification of ideas and/or information; acts of creativity, problem-solving, and possibly intuition; and mental processes such as learning, perception, and/or awareness of ideas and/or information. The mental processes are distinct from those of beliefs, desires, and the like. In some embodiments, cognitive function may be assessed, and thus optionally defined, via one or more tests or assays for cognitive function. Non-limiting examples of a test or assay for cognitive function include CANTAB (see for example Fray et al. "CANTAB battery: proposed utility in neurotoxicology." *Neurotoxicol Teratol.* 1996; 18(4):499-504), Stroop Test, Trail Making, Wechsler Digit Span, or the CogState computerized cognitive test (see also Dehaene et al. "Reward-dependent learning in neuronal networks for planning and decision making. *Brain Res.* 2000; 126:21729; Iverson et al. "Interpreting change on the WAIS-III/WMS-III in clinical samples." *Arch Clin Neuropsychol.* 2001; 16(2):183-91; and Weaver et al. "Mild memory impairment in healthy older adults is distinct from normal aging." Cogn. 2006; 60(2):146-55).

The methods of the invention may be used to promote cognitive function in a normal subject or to treat a subject having a cognitive dysfunction. A normal subject, as used herein, is a subject that has not been diagnosed with a disorder associated with impaired cognitive function.

Impaired cognitive function refers to cognitive function that is not as robust as that observed in an age-matched normal subject and includes states in which cognitive function is reduced. In some cases, cognitive function is reduced by about 5%, about 10%, about 30%, or more, compared to cognitive function measured in an age-matched normal subject. Cognitive function may be promoted to any detectable degree, but in humans preferably is promoted sufficiently to allow an impaired subject to carry out daily activities of normal life.

In some embodiments, methods for treating cognitive function disorders or impairments are provided. The methods comprise administering to a subject in need thereof an effective amount of 4-(acetylamino)-N-(2-aminophenyl)benzamide (CI-994) or its metabolite dinaline. The CI-994 or dinaline may be administered at a dosage effectively low to maintain an effective cumulative CI-994 serum concentration in the subject. The CI-994 or dinaline may be administered once every other day. In some embodiments the CI-994 or dinaline may be administered once, twice, three, four, or five times a day, and/or every other day, every third day, every fourth day, every fifth day, every sixth day, every seventh day, etc. The CI-994 or dinaline may also be administered for at least 1, 2, 3, 4, 5, 6, 7, 8, 9, 10, 11, 12, 13, 14, 15, 16, 17, 18, 19, or 20 days. The CI-994 or dinaline may be administered orally, transdermally, intravenously, cutaneously, subcutaneously, nasally, intramuscularly, intraperitonealy, intracranially, or intracerebroventricularly.

In some embodiments, the cognitive function disorders or impairments are associated with, but not limited to, Alzheimer's disease, Huntington's disease, seizure-induced memory loss, schizophrenia, Rubinstein Taybi syndrome, Rett Syndrome, Fragile X, Lewey body dementia, Vascular dementia, bipolar disorder and social, cognitive and learning disorders associated with autism, ADHD, dyslexia, learning disorders, traumatic head injury, stroke induced cognitive and motor impairment, traumatic brain injury, neurodegeneration and neuronal loss mediated cognitive impairment, and attention deficit disorder. In some embodiments, the cognitive function disorders or impairments are associated with, but not limited to, anxiety disorders, conditioned fear response, panic disorders, obsessive compulsive disorders, post-traumatic stress disorder, phobias, social anxiety disorders, substance dependence recovery or Age Associated Memory Impairment (AAMI), and Age Related Cognitive Decline (ARCD). A person of skill in the art will that the methods of the inventions may be used to treat any condition associated with cognitive function disorders or impairments.

Alzheimer's disease is a degenerative brain disorder characterized by cognitive and noncognitive neuropsychiatric symptoms, which accounts for approximately 60% of all cases of dementia for patients over 65 years old. In Alzheimer's disease the cognitive systems that control memory have been damaged. Often long-term memory is retained while short-term memory is lost; conversely, memories may become confused, resulting in mistakes in recognizing people or places that should be familiar. Psychiatric symptoms are common in Alzheimer's disease, with psychosis (hallucinations and delusions) present in many patients. It is possible that the psychotic symptoms of Alzheimer's disease involve a shift in the concentration of dopamine or acetylcholine, which may augment a dopaminergic/cholinergic balance, thereby resulting in psychotic behavior. For example, it has been proposed that an increased dopamine release may be responsible for the positive symptoms of schizophrenia. This may result in a positive disruption of the dopaminergic/cholinergic balance. In Alzheimer's disease, the reduction in cholinergic neurons effectively reduces acetylcholine release resulting in a negative disruption of the dopaminergic/cholinergic balance. Indeed, antipsychotic agents that are used to relieve psychosis of schizophrenia are also useful in alleviating psychosis in Alzheimer's patients and could be combined with the compositions described herein for use in the methods of the invention.

Methods for recapturing a memory in a subject having Alzheimer's disease by administering a CI-994 or dinaline or the other related compounds of the invention are also provided according to the invention. Such methods optionally involve administering the inhibitor and monitoring the subject to identify recapture of a memory that was previously lost. Subjects may be monitored by routine tests known in the art. For instance some are described in books such as DSM described above or in the medical literature.

In other embodiments the Alzheimer's patient is one that has late stage Alzheimer's disease. Many of the drugs suggested for treating Alzheimer's disease are designed to treat the early stages of the disease by preventing plaque build up. The instant compounds are useful for treating both early stages and late stages of dementia, because they actually improve memory and cognition rather than preventing only plaque accumulation.

Vascular dementia, also referred to as "multi-infarct dementia", refers to a group of syndromes caused by different mechanisms all resulting in vascular lesions in the brain. The main subtypes of vascular dementia are, for example vascular mild cognitive impairment, multi-infarct dementia, vascular dementia due to a strategic single infarct (affecting the thalamus, the anterior cerebral artery, the parietal lobes or the cingulate gyms), vascular dementia due to hemorrhagic lesions, small vessel disease (including, e.g. vascular dementia due to lacunar lesions and Binswanger disease), and mixed Alzheimer's Disease with vascular dementia.

Figure 40:
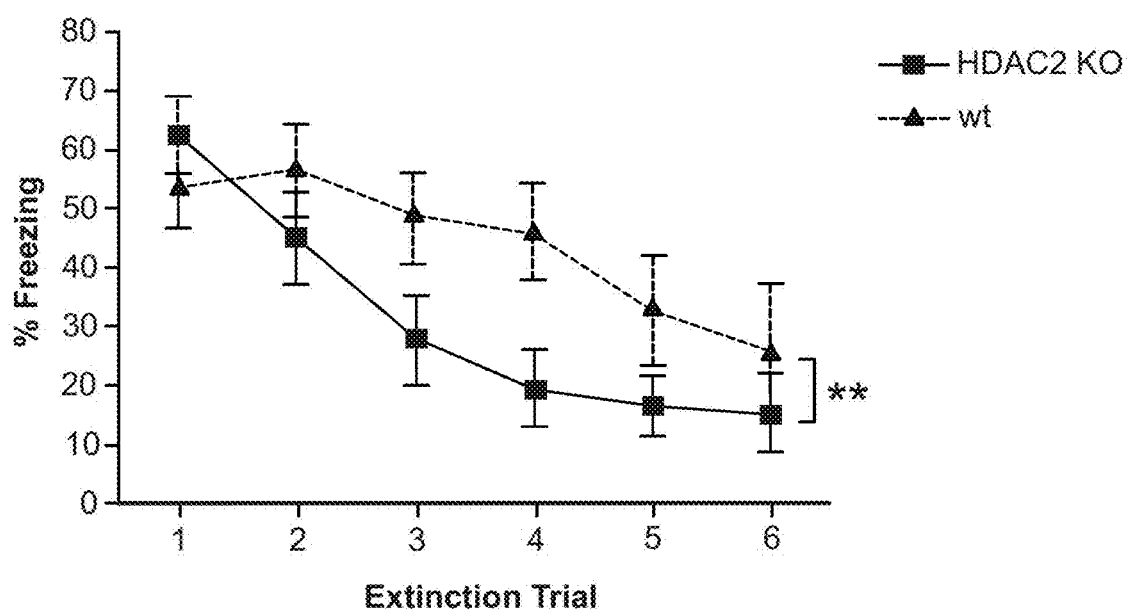
FIG. 40 demonstrates that HDAC2 knockout mice (n=8 males) exhibited faster contextual fear extinction compared to wt controls (n=7 males, **P=0.0043, Two-way-ANOVA).
Figure 41A:
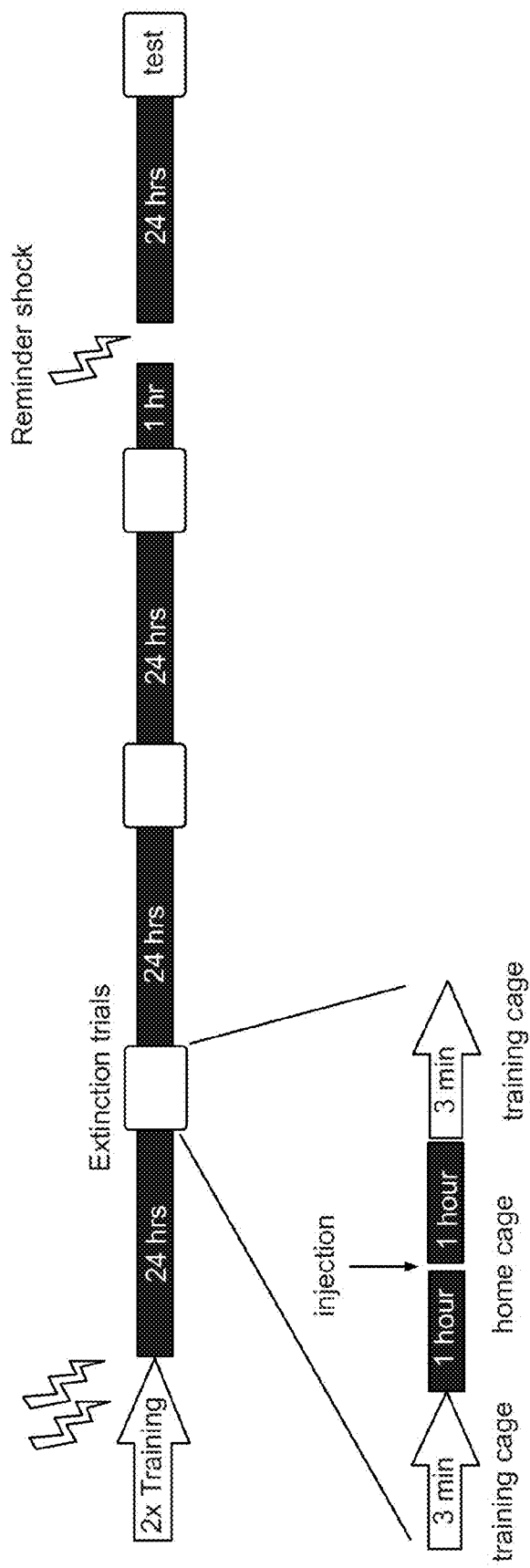
FIG. 41 demonstrates that CI-994 promotes fear memory extinction. A. The protocol used to test the effect of CI-994 on fear memory extinction. B. Extinction of the fear memory was much faster in the CI-994 treated group than the vehicle treated group during the first 3-min-exposure in each day. On the third day, CI-994 group showed significantly less freezing time than the control group. N=8 for each group. *, p<0.05. C. CI-994 group showed faster decay of freezing time in the two contextual exposure training, before and after injection, during extinction day 1. D. CI-994 group showed faster decay of freezing time in the two contextual exposure training, before and after injection, during extinction day 2. E. No significant differences were observed between CI-994 group and control group, both of which showed high level of freezing 24 hours after the reminder shock.
Figure 41C:
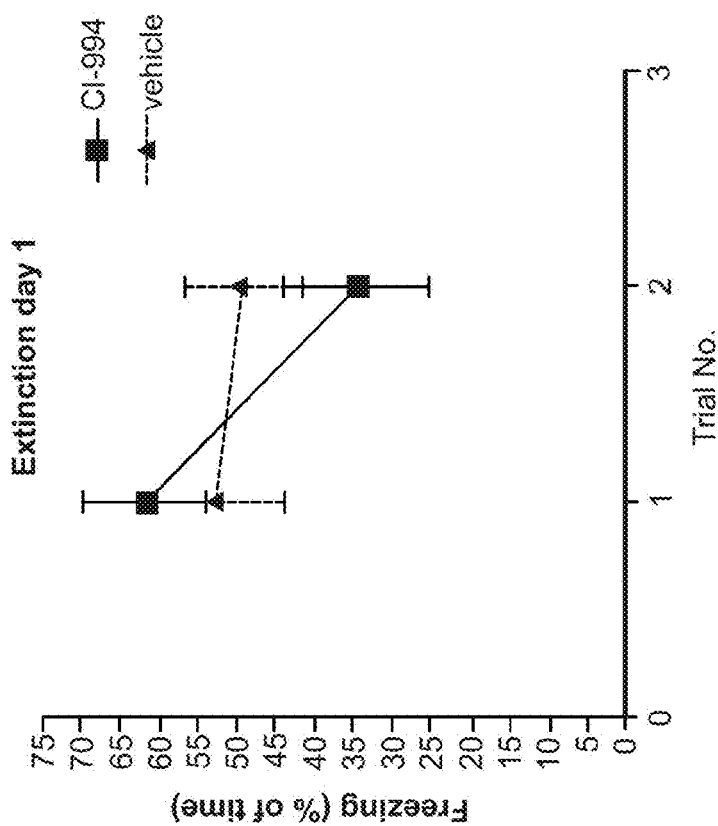
Figure 41B:
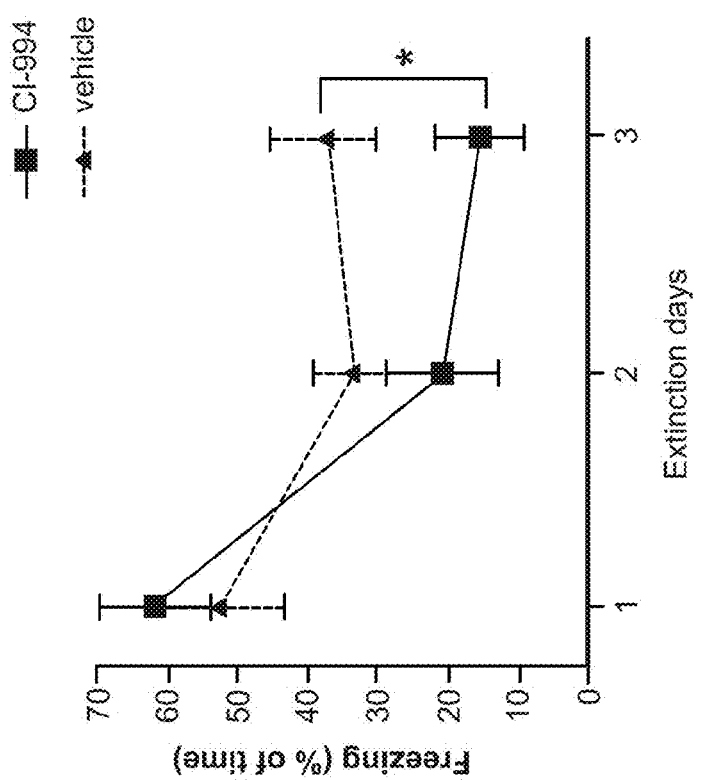
Figure 41E:
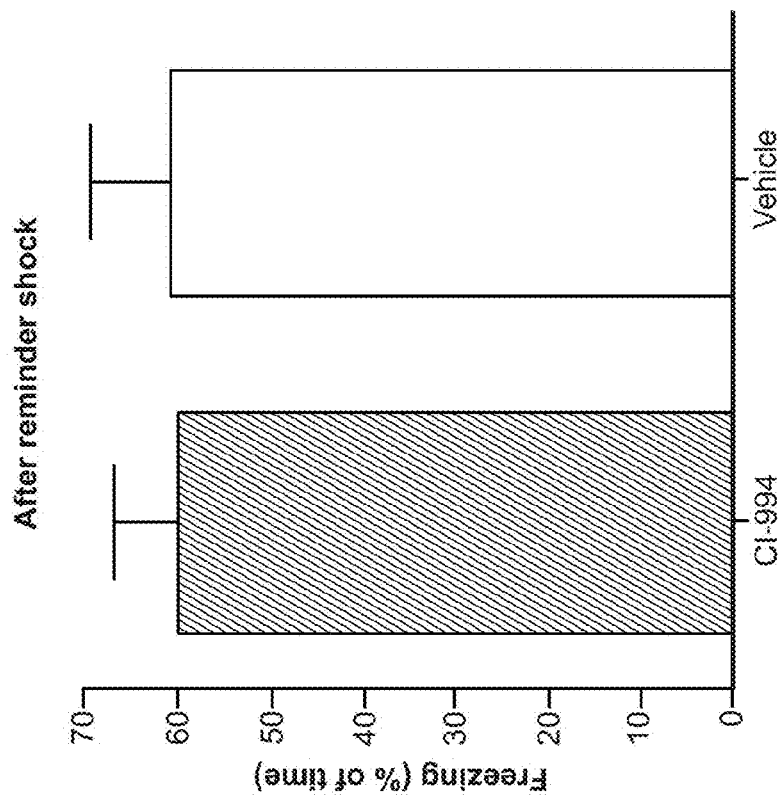
Figure 41D:
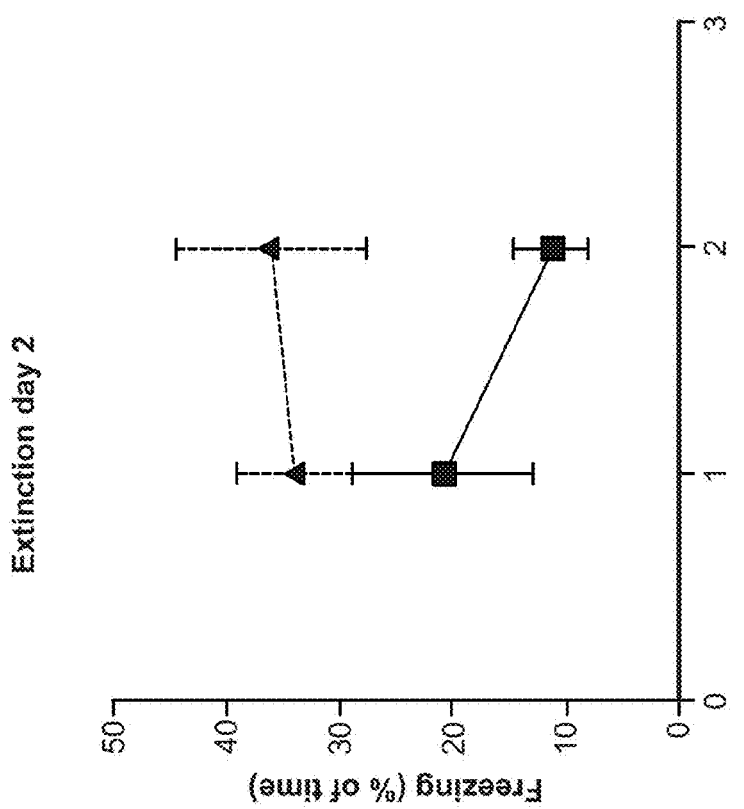

Post-Traumatic Stress Disorder, PTSD, is an anxiety disorder that can develop after exposure to a terrifying event or ordeal in which grave physical harm occurred or was threatened. Traumatic events that may trigger PTSD include violent personal assaults, natural or human-caused disasters, accidents, or military combat. In general, it is a disease with impaired fear memory extinction. Fear extinction is the decrease in conditioned fear responses that normally occurs when a conditioned stimulus (CS) is repeatedly presented in the absence of the aversive unconditioned stimulus (US). Extinction does not erase the initial CS-US association, but is thought to form a new memory. Deficits in fear extinction are thought to contribute to post-traumatic stress disorder (PTSD), phobias, anxiety disorders, etc. Interestingly, we found that HDAC2 over expression mice were impaired in extinction of fear memory compared to WT control mice (FIG. 32), while HDAC2 knockout mice exhibited faster contextual fear extinction compared to wild type controls (FIG. 40).

In some embodiments, the subject may undergo additional therapies to treat the disorder in addition to the CI-994 or dinaline. The combination therapies may be any type of therapy appropriate for treating the particular disease. For instance the combination therapy may be behavioral therapy or medicaments. Behavioral therapy comprises, but is not limited to, electroconvulsive seizure therapy, exercise, group therapy, talk therapy, or conditioning. In another embodiment, the behavioral therapy is cognitive-behavioral therapy. Examples of behavioral therapy that may be used in the ongoing methods are described, for example, in Cognitive-Behavioral Therapies by K. Dobson, ed., Guilford Publications, Inc., 2002; The new Handbook of Cognitive Therapy Techniques by Rian E. McMullin; Norton, W. W. & Company, Inc., 2000; and Cognitive Therapy: Basics and Beyond by Judith S. S. Beck, Guilford Publications, Inc., 1995, herein incorporated by reference in their entireties.

The HDAC inhibitor CI-994 is of the formula:

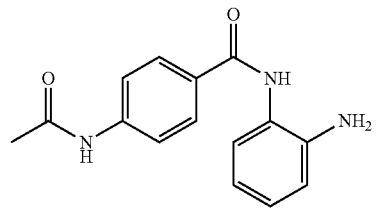

CI-994
(tacedinaline)
Chemical Formula:
$C_{15}H_{15}N_3O_2$
Molecular Weight: 269.30

In some embodiments, a pharmaceutically acceptable salt of CI-994 is administered. In some embodiments, the pharmaceutically acceptable salt is of the formula:

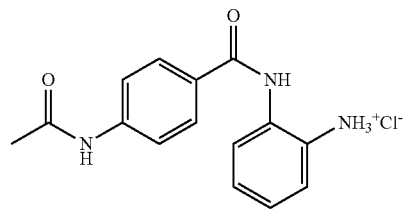

CI-994
HCl salt
Chemical Formula:
$C_{15}H_{16}ClN_3O_2$
Molecular Weight: 305.76

In some embodiments, dinaline, a metabolite of CI-994 is administered. The dinaline is of the formula:

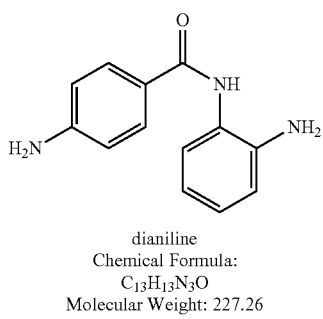 [SMILES: Nc1ccc(C(=O)Nc2ccccc2N)cc1]

dianiline
Chemical Formula:
$C_{13}H_{13}N_3O$
Molecular Weight: 227.26

According to some aspects of the invention, CI-994 or dinaline or pharmaceutically acceptable salts thereof are administered alone. In some embodiments, CI-994 and dinaline are administered in combination. CI-994 may administered at the same time as dinaline administration, or prior to the administration of dinaline. In some aspects, CI-994 is administered following the use of dinaline.

Furthermore, all possible combinations of the above-mentioned embodiments form also part of this invention. The present invention, in some aspects, also provides metabolites, salts, solvates and prodrugs of CI-994, dinaline and pharmaceutically acceptable salts thereof. Thus, the compounds of the invention may form salts with acids. Examples of pharmaceutically acceptable salts include, among others, addition salts with inorganic acids such as hydrochloric, hydrobromic, hydroiodic, nitric, perchloric, sulphuric and phosphoric acid, as well as addition salts of organic acids such as acetic, methanesulfonic, trifluoromethanesulfonic, ethanesulfonic, benzenesulfonic, p-toluenesulfonic, benzoic, camphorsulfonic, mandelic, oxalic, succinic, fumaric, tartaric, and maleic acid. Likewise, compounds of the present invention may contain one or more acid protons and, therefore, they may form salts with bases, that also form part of this invention. Examples of these salts include salts with metal cations, such as for example an alkaline metal ion, an alkaline-earth metal ion or an aluminum ion; or it may be coordinated with an organic with an organic or inorganic base. An acceptable organic base includes among others diethylamine and triethylamine. An acceptable inorganic base includes aluminium hydroxide, calcium hydroxide, potassium hydroxide, sodium carbonate, and sodium hydroxide. There may be more than one cation or anion depending on the number of functions with charge and on the valency of cations and anions.

Salts derived from pharmaceutically acceptable organic nontoxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

There is no limitation on the type of salt that can be used provided that these are pharmaceutically acceptable when they are used for therapeutic purposes. Salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, such as ether, ethyl acetate, ethanol, isopropanol, or acetonitrile or in a mixture of the two.

Some of the compounds of the present invention may exist in unsolvated as well as solvated forms such as, for example, hydrates. The present invention encompasses all such above-mentioned forms which are pharmaceutically active.

Compounds of the invention may include at least one chiral center. The present invention includes each one of the possible stereoisomers and mixtures thereof, particularly racemic mixtures thereof. A single enantiomer may be prepared by any of the commonly used processes, for example, by chromatographic separation of the racemic mixture on a stationary chiral phase, by resolution of the racemic mixture by fractional crystallisation techniques of the diastereomeric salts thereof, by chiral synthesis, by enzymatic resolution or by biotransformation. This resolution can be carried out on any chiral synthetic intermediate or on CI-994 or dinaline. Alternatively, any enantiomer may be obtained by enantiospecific synthesis using optically pure starting materials or reagents of known configuration.

Some of the compounds of the present invention may exist as several diastereoisomers, which may be separated by conventional techniques such as chromatography or fractional crystallization. Some compounds of the present invention may exhibit cis/trans isomers. The present invention includes each of the geometric isomers and its mixtures. The present invention covers all isomers and mixtures thereof (for example racemic mixtures) whether obtained by synthesis and also by physically mixing them. The present invention relates to a process for the preparation of the above said novel compounds, their derivatives, their analogues, their tautomeric forms, their stereoisomers, or their pharmaceutical acceptable salts and solvates.

A histone deacetylase inhibitor as used herein is a compound that inhibits, reduces, or otherwise modulates the activity of histone deacetylase. In various embodiments, administering CI-994 or dinaline according to methods provided herein reduces histone deacetylase activity by at least about 5%, at least about 15%, at least about 25%, at least about 50%, at least about 75%, at least about 90%, or at least about 100% or more in comparison to the absence of CI-994 or dinaline. In further embodiments, histone deacetylase activity is reduced by at least about 95% or by at least about 99% or more. Methods for assessing histone deacetylase activity are known in the art, and are described, e.g., in Richon et al., *Methods Enzymol.*, 376:199-205 (2004), Wegener et al., *Mol Genet Metab.*, 80(1-2): 138-47 (2003), U.S. Pat. No. 6,110,697, and U.S. Patent Publication Nos. 20050227300, 20050118596, 20030161830, 20030224473, 20030082668, 20030013176, and 20040091951, all of which are incorporated herein by reference in their entirety. Methods for assessing histone deacetylase activity in human patients are also known in the art, and are described, e.g., in U.S. Patent Publication No. 20050288227, herein incorporated by reference in its entirety.

The present invention also provides methods for treating Alzheimer's disease by administering CI-994, dinaline or a pharmaceutically acceptable salt, ester or prodrug thereof. Alzheimer's disease is a disorder in which the cognitive systems that control memory have been damaged. Often long-term memory is retained while short-term memory is lost; conversely, memories may become confused, resulting in mistakes in recognizing people or places that should be familiar.

The CI-994 or dinaline may be administered on a recurring basis, such as daily, weekly, or monthly in one or more doses. Alternatively, it can be administered on a non-regular basis e.g. whenever symptoms begin.

The CI-994 or dinaline may be administered orally, transdermally, intravenously, cutaneously, subcutaneously, nasally, intramuscularly, intraperitonealy, intracranially, or intracerebroventricularly.

The present invention also provides methods for treating Huntington's disease by administering an effective amount of CI-994 or dinaline. Huntington's disease is a neurological disease which results in cognitive decline associated with inexorable progression to death. Cognitive symptoms associated with Huntington's disease include loss of intellectual speed, attention and short term memory and/or behavioral symptoms. The CI-994 or dinaline may be administered once every other day. The CI-994 or dinaline may be administered orally, transdermally, intravenously, cutaneously, subcutaneously, nasally, intramuscularly, intraperitonealy, intracranially, or intracerebroventricularly. In some embodiments, the method of treatment is not selected based on expression levels of Huntington disease biomarker genes selected from the group consisting of ANXA1, AXOT, CAPZA1, HIF1A, JJAZ1, P2Y5, PCNP, ROCK1 (p160ROCK), SF3B1, SP3, TAF7 and YIPPEE. In some embodiments, the diagnosis and the method of treatment are not selected based on expression levels of Huntington disease biomarker genes disclosed in US patent application US 2007/0015183. In some embodiments, the diagnosis and the method of treatment are selected based on medical history, family history or brain imaging tests.

As used herein, treating condition or patient refers to taking steps to obtain beneficial or desired results, including clinical results. Beneficial or desired clinical results include, but are not limited to, alleviation or amelioration of one or more symptoms associated with disorders involving cognitive dysfunction, diminishment of extent of disease, delay or slowing of disease progression, amelioration, palliation or stabilization of the disease state, and other beneficial results, such as improvement of cognitive function or a reduced rate of decline of cognitive function.

The invention also relates to improving cognitive function in a normal subject by administering an effective amount of CI-994 or dinaline. Improving cognitive function includes promoting cognitive function in the subject so that it more closely resembles or exceeds the function of an age-matched normal, unimpaired subject. A normal subject is a subject that has not been diagnosed with any disorder or condition associated with impaired cognitive function. Cognitive performance of a subject is influenced by a variety of factors and the methods of the invention can be practiced to counteract any factors, for example, sleep deprivation, mental exhaustion, physical exhaustion or overexertion.

A subject shall mean a human or vertebrate animal or mammal including but not limited to a dog, cat, horse, cow, pig, sheep, goat, turkey, chicken, and primate, e.g., monkey. In some embodiments subjects are those which are not otherwise in need of an HDAC inhibitor. Human subjects are preferred.

The term effective amount of the therapeutic compounds of the invention refers to the amount necessary or sufficient to realize a desired biologic effect. For example, an effective amount of a therapeutic compounds of the invention is that amount sufficient to re-establish access to a memory. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic compounds being administered the size of the subject, or the severity of the disease or condition. One of ordinary skill in the art can empirically determine the effective amount of a particular therapeutic compounds of the invention without necessitating undue experimentation. Compositions of the invention include compounds as described herein, or a pharmaceutically acceptable salt or hydrate thereof.

Subject doses of the compounds described herein for delivery typically may be less than 15 mg/m2 once a day for 14 straight days, which depending on the application could be given daily, weekly, or monthly and any other amount of time there between. In some embodiments, the CI-994 and/or its metabolite is administered at a dosage lower than 15 mg/m2 once a day for 14 consecutive days. In one embodiment, the composition is administered once a day for at least 2 consecutive days. In another embodiment, the therapeutic compounds are administered once every other day, or once a day with at least 2 days between doses. In yet other embodiments the dosage may be 30 mg/m2 every other day or even an acute dose of 80 mg/m2 may be tolerated. Since there is some variance in humans at a given dose the dose may be personalized in some instances. Such manipulation is within the skill of the ordinary artisan in view of the teachings found herein. The serum levels associated with an oral dose level of less than 15 mg/m2 once a day are given below as the average with the associated variance in parenthesis (the variance is expressed as a percentage of the mean value). There are 2 measures of concentration, the Cmax and the AUC.

$C_{max}$ (ng/mL)=570 (25.1%)

AUC (ng·hr/mL)=9500 (62.7%)

In some embodiments, the CI-994 and/or its metabolite is administered at a dosage of 0.01 mg/kg, 0.05 mg/kg, 0.1 mg/kg, 0.5 mg/kg, 1 mg/kg, 5 mg/kg, 10 mg/kg, 20 mg/kg, 30 mg/kg, 50 mg/kg, 75 mg/kg or 100 mg/kg. In some embodiments, the CI-994 and/or its metabolite is administered at a dosage of less than 15 mg/kg. In some embodiments, the CI-994 and/or its metabolite is administered at a dosage of 1 mg/kg once a day for 10 consecutive days.

The formulations of the invention are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of the therapeutic compounds of the invention can be administered to a subject by any mode that delivers the therapeutic agent or compound to the desired surface, e.g., mucosal, systemic. Administering the pharmaceutical composition of the present invention may be accomplished by any means known to the skilled artisan. In some embodiments, routes of administration include but are not limited to oral, transdermal, parenteral, intravenously, cutaneously, subcutaneously, intramuscular, intranasal, intraperitoneal, sublingual, intratracheal, inhalation, ocular, vaginal, rectal, intracranial and intracerebroventricular. Preferred routes of administration include oral, transdermal, nasal and intraperitoneal.

For oral administration, the therapeutic compounds of the invention can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the therapeutic agent or by release of the biologically active material beyond the stomach environment, such as in the intestine.

To ensure full gastric resistance a coating impermeable to at least pH 5.0 is important. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the therapeutic agent may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the therapeutic agent either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of therapeutic agent. Typically, each formulation is specific to the type of device employed and may involve the use of an appropriate propellant material, in addition to the usual diluents, and/or carriers useful in therapy. Also, the use of liposomes, microcapsules or microspheres, inclusion complexes, or other types of carriers is contemplated. Chemically modified therapeutic agent may also be prepared in different formulations depending on the type of chemical modification or the type of device employed.

Formulations suitable for use with a nebulizer, either jet or ultrasonic, will typically comprise therapeutic agent dissolved in water. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol. Formulations for use with a metered-dose inhaler device will generally comprise a finely divided powder containing the therapeutic agent suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing therapeutic agent and may also include a bulking agent, such as lactose, sorbitol, sucrose, or mannitol in amounts which facilitate dispersal of the powder from the device, e.g., 50 to 90% by weight of the formulation. The therapeutic agent should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990, which is incorporated herein by reference.

The therapeutic compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a therapeutic compound of the invention optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agents may be delivered to the brain using a formulation capable of delivering a therapeutic agent across the blood brain barrier. One obstacle to delivering therapeutics to the brain is the physiology and structure of the brain. The blood-brain, barrier is made up of specialized capillaries lined with a single layer of endothelial cells. The region between cells are sealed with a tight junction, so the only access to the brain from the blood is through the endothelial cells. The barrier allows only certain substances, such as lipophilic molecules through and keeps other harmful compounds and pathogens out. Thus, lipophilic carriers are useful for delivering non-lipohilic compounds to the brain. For instance, DHA, a fatty acid naturally occurring in the human brain has been found to be useful for delivering drugs covalently attached thereto to the brain (Such as those described in U.S. Pat. No. 6,407,137). U.S. Pat. No. 5,525,727 describes a dihydropyridine pyridinium salt carrier redox system for the specific and sustained delivery of drug species to the brain. U.S. Pat. No. 5,618,803 describes targeted drug delivery with phosphonate derivatives. U.S. Pat. No. 7,119,074 describes amphiphilic prodrugs of a therapeutic compound conjugated to an PEG-oligomer/polymer for delivering the compound across the blood brain barrier. The compounds described herein may be modified by covalent attachment to a lipophilic carrier or co-formulation with a lipophilic carrier. Others are known to those of skill in the art.

The therapeutic agents of the invention may be delivered with other therapeutics for enhancing memory retrieval or treating other symptoms or causes of disorders associated with the memory loss. For instance, environmental enrichment (EE) has been used for enhancing memories. EE involves creating a stimulating environment around a subject. Other therapeutics may also be combined to treat the underlying disorder or to enhance memory recall.

Examples of combinations of the compounds of the present invention with other drugs in either unit dose or kit form include combinations with: anti-Alzheimer's agents, beta-secretase inhibitors, gamma-secretase inhibitors, HMG-CoA reductase inhibitors, NSAID's including ibuprofen, N-methyl-D-aspartate (NMDA) receptor antagonists, such as memantine, cholinesterase inhibitors such as galantamine, rivastigmine, donepezil, and tacrine, vitamin E, CB-1 receptor antagonists or CB-1 receptor inverse agonists, antibiotics such as doxycycline and rifampin, anti-amyloid antibodies, or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The invention also includes articles, which refers to any one or collection of components. In some embodiments the articles are kits. The articles include pharmaceutical or diagnostic grade compounds of the invention in one or more containers. The article may include instructions or labels promoting or describing the use of the compounds of the invention.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of cognitive disorders such as Alzheimer's disease.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kits, in one set of embodiments, may comprise a carrier means being compartmentalized to receive in close confinement one or more container means such as vials, tubes, and the like, each of the container means comprising one of the separate elements to be used in the method. For example, one of the containers may comprise a positive control for an assay. Additionally, the kit may include containers for other components, for example, buffers useful in the assay.

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In another embodiment, compositions of the invention are stored in containers with biocompatible detergents, including but not limited to, lecithin, taurocholic acid, and cholesterol; or with other proteins, including but not limited to, gamma globulins and serum albumins. More preferably, compositions of the invention are stored with human serum albumins for human uses, and stored with bovine serum albumins for veterinary uses.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures and other monitoring information.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising a needle or syringe, preferably packaged in sterile form, for injection of the formulation, and/or a packaged alcohol pad.

In a specific embodiment, an article of manufacture comprises packaging material and a pharmaceutical agent and instructions contained within said packaging material, wherein said pharmaceutical agent is a CI-994 or dinaline and a pharmaceutically acceptable carrier, and said instructions indicate a dosing regimen for preventing, treating or managing a subject with cognitive disorders such as Alzheimer's disease.

Therapeutic Monitoring: The adequacy of the treatment parameters chosen, e.g. dose, schedule, adjuvant choice and the like, is determined by conventional methods for monitoring memory. In addition, the clinical condition of the patient can be monitored for the desired effect, e.g. increases in cognitive function. If inadequate effect is achieved then the patient can be boosted with further treatment and the treatment parameters can be modified, such as by increasing the amount of the composition of the invention and/or other active agent, or varying the route of administration.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Characterization of CI-994 and Dinaline as HDAC Inhibitors

In vitro binding data: The enzymatic inhibitory activity of CI-994 and dinaline against several of the known HDAC isoforms was assayed. The enzymatic inhibition profile for these two compounds is shown in FIG. 2. Comparison was also made to other known memory enhancers and their ability to inhibit the same HDAC enzymes. Both compounds are primarily Class I HDAC inhibitors.

Example 1A

Characterization of CI-994 and Dinaline as Time Dependent HDAC Inhibitors

In vitro binding data: The enzymatic inhibitory activity of CI-994 and diniline against several of the known HDAC isoforms was assayed with 1-3 h preincubation. The enzymatic inhibition profile for these two compounds is shown in FIG. 1A. Comparison was also made to other known memory enhancers and their ability to inhibit the same HDAC enzymes. Both compounds are primarily Class I HDAC inhibitors.

Example 2

Acetylation Marks in Rubinstein Taybi CBP$^{+/-}$ Mice

The data of this Example was previously published, but is presented herein to demonstrate the relevance of the specific acetylation mark (H2B) elicited by CI-994 in the brain and how this relates to the treatment of Rubinstein Taybi. The data of Example 2 is not part of the invention.

Immunostaining of sagittal brain sections of Rubinstein Taybi CBP$^{+/-}$ mice using antibodies revealed a decreased level of AcH2B in hippocampal neurons (FIG. 2A). Western blot analysis of hippocampal protein extracts from CBP$^{+/-}$ and WT mice using antibodies against β-actin, H2B (non-acetylated), AcH2A, AcH3 and AcH4 revealed a similar decrease in AcH2B level (FIG. 2B). Quantification of Western blot analysis showed no differences in the level of β-actin, total H2B, AcH2A, AcH3, but a significant difference in the level of AcH2B. A similar reduction in H2B acetylation was also observed using another AcH2B antibody (FIG. 2C).

Example 3

In Vitro Data with CI-994 in Neuronal Cell Lines

Figure 10A:
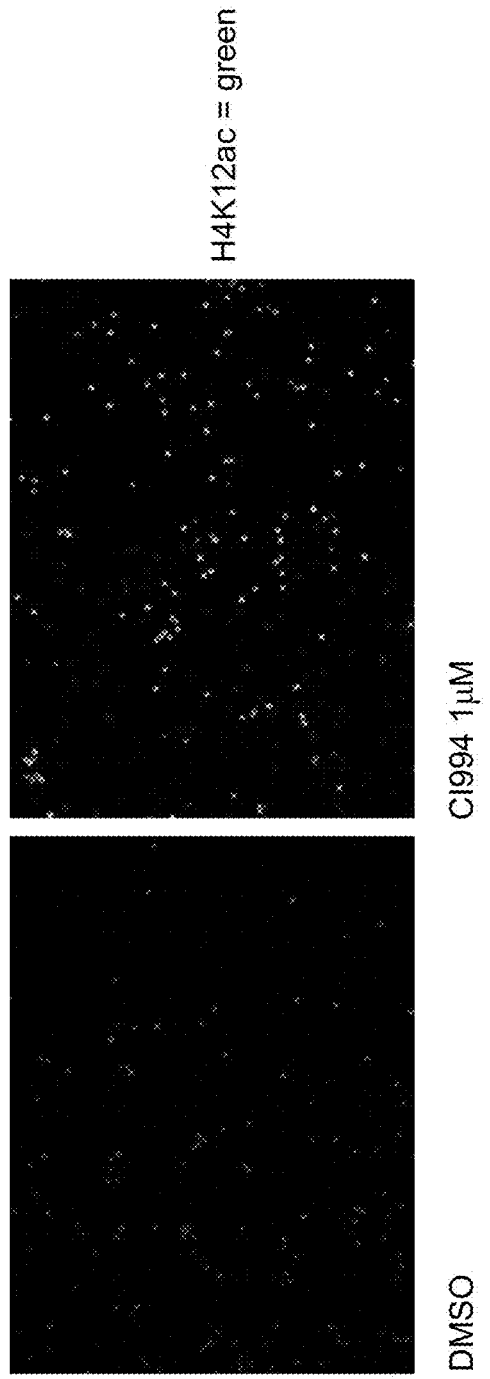
FIG. 10 shows that treatment of neuronal cells with CI-994 increases H4K12 acetylation in vitro. A. The micrograph shows the increased fluorescence in primary neuronal cells after treatment with DMSO or 1 uM CI-994 after 6 h incubation. The increased green fluorescence corresponds to increased levels of H4K12 acetylation. B. Control demonstrating that CI-994 at 1 and 10 uM does not cause an increase or decrease in overall cell number after 6 h incubation in brain region specific primary cultures (cortex and striatum). C. Histograms showing that CI-994 at 1 and 10 uM causes an increase in H4K12 acetylation after 6 h incubation in brain region specific primary cultures (cortex and striatum).
Figure 10C:
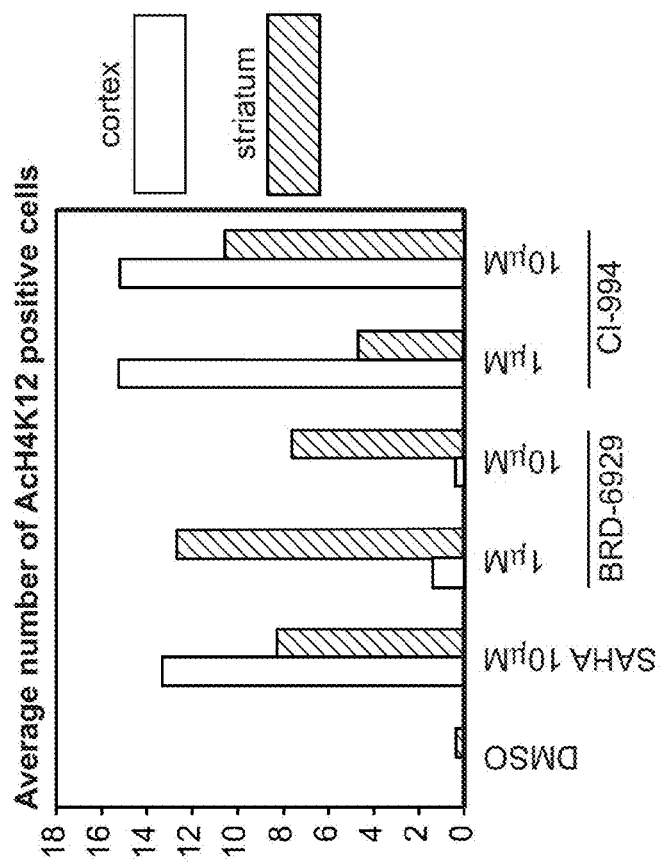
Figure 10B:
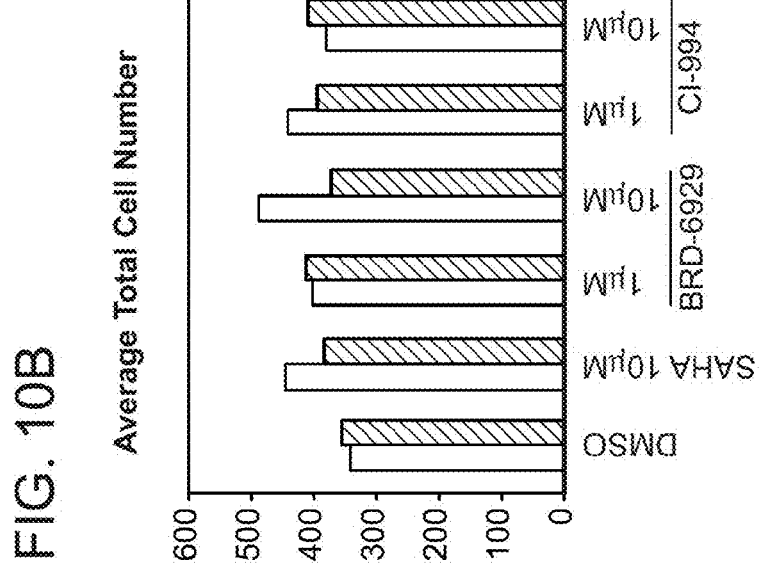
Figure 11A:
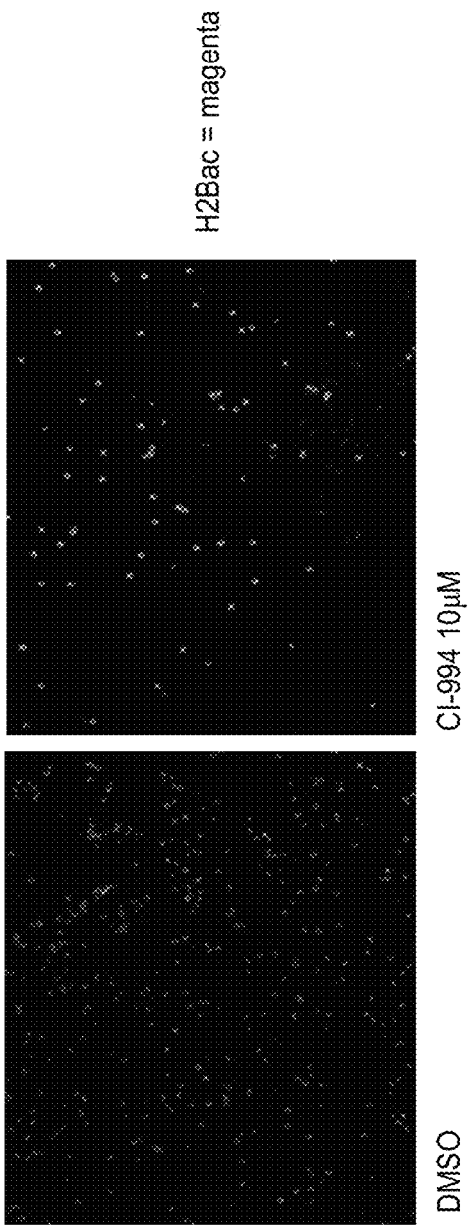
FIG. 11 shows that treatment of neuronal cells with CI-994 increases H2B acetylation in vitro. A. The micrograph shows the increased fluorescence in primary neuronal cells after treatment with DMSO or 10 uM CI-994 after 6 h incubation. The increased magenta fluorescence corresponds to increased levels of H2B tetra-acetylation. B. Control demonstrating that CI-994 at 1 and 10 uM does not cause an increase or decrease in overall cell number after 6 h incubation in brain region specific primary cultures (striatum). C. The histograms showing that CI-994 at 1 and 10 uM causes an increase in H2B tetra-acetylation after 6 h incubation in brain region specific primary cultures (striatum).
Figure 11C:
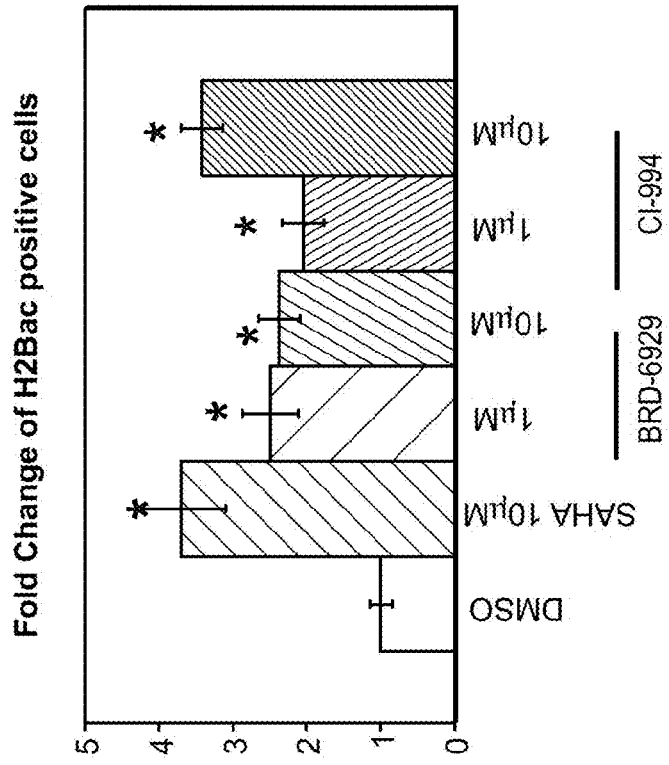
Figure 11B:
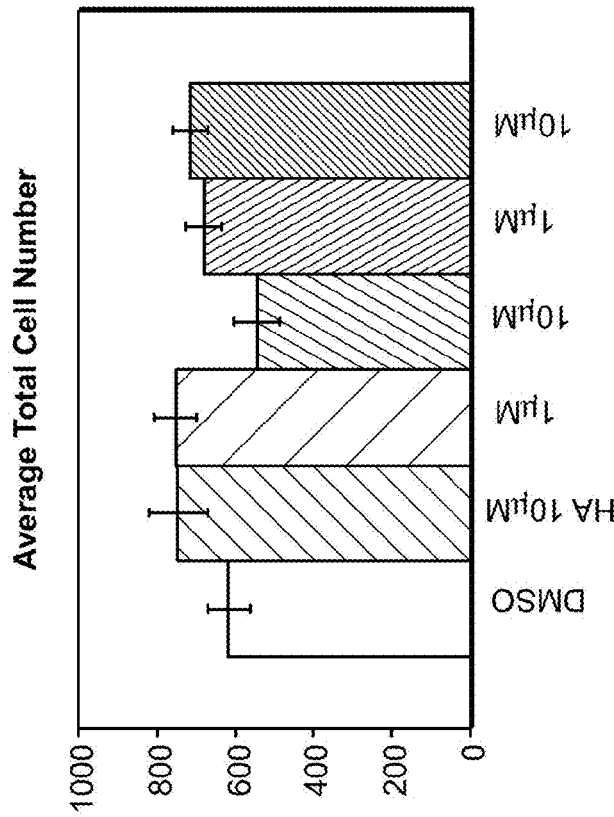
Figure 12:
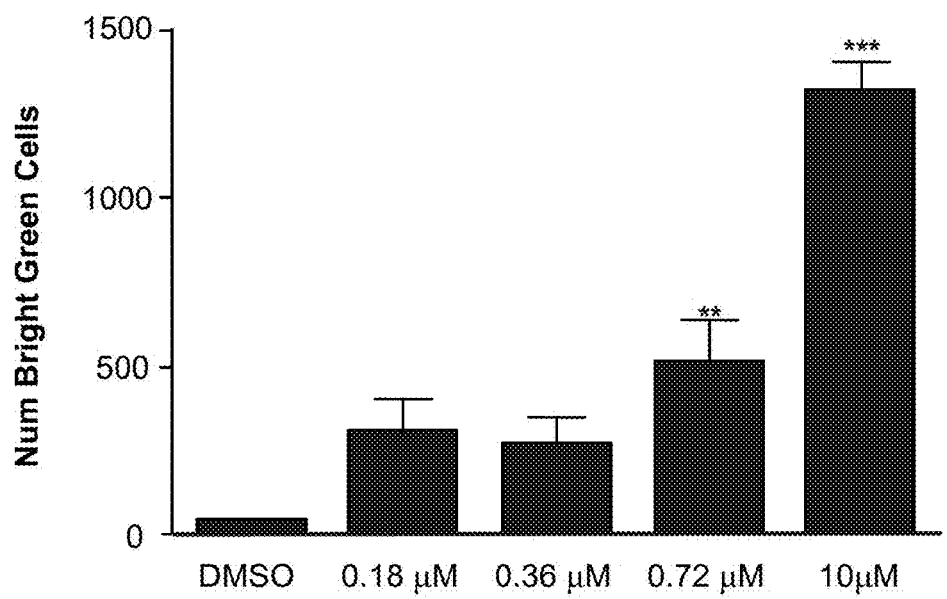
FIG. 12 shows a dose response of CI-994 in a primary cell culture from mouse forebrain. The data demonstrates the effect of increasing doses of CI-994 on H4K12 acetylation levels. CI-994 is able to functionally inhibit HDAC enzymes at relative low dose and causes an increasing functional response at increasing doses.
Figure 13A:
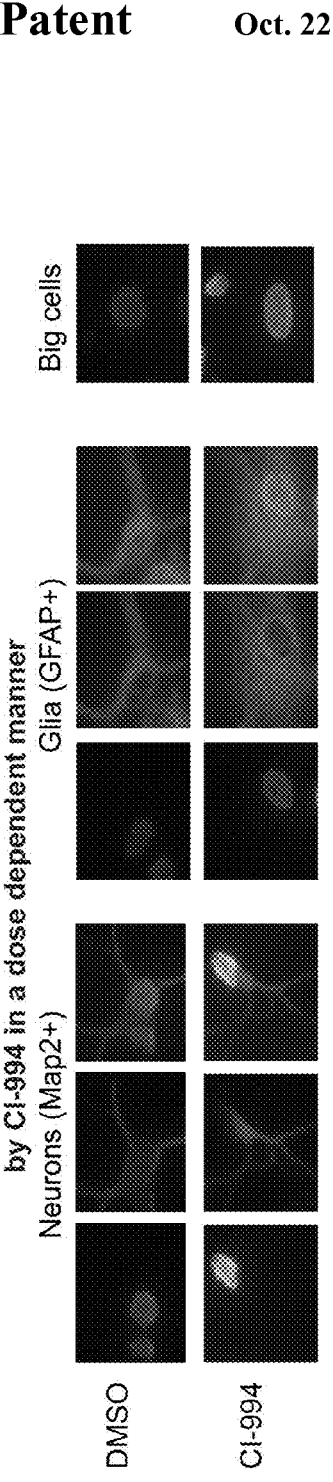
FIG. 13 shows that CI-994 increases H4K12 acetylation in specific cell types and brain regions in a dose dependent manner. A. The micrographs demonstrate the effect on specific cell types in a primary neuronal cell culture after the treatment with DMSO or 10 uM CI-994 (6 h). Increased H4K12 immunofluorscence (green) co-localized with neurons (map2+ stain), glia (GFAP+ stain) and large cell types. B. Quantitation of the increased fluorescence associated with H4K12 acetylation on specific cell types and in specific brain region cell cultures.
Figure 13B:
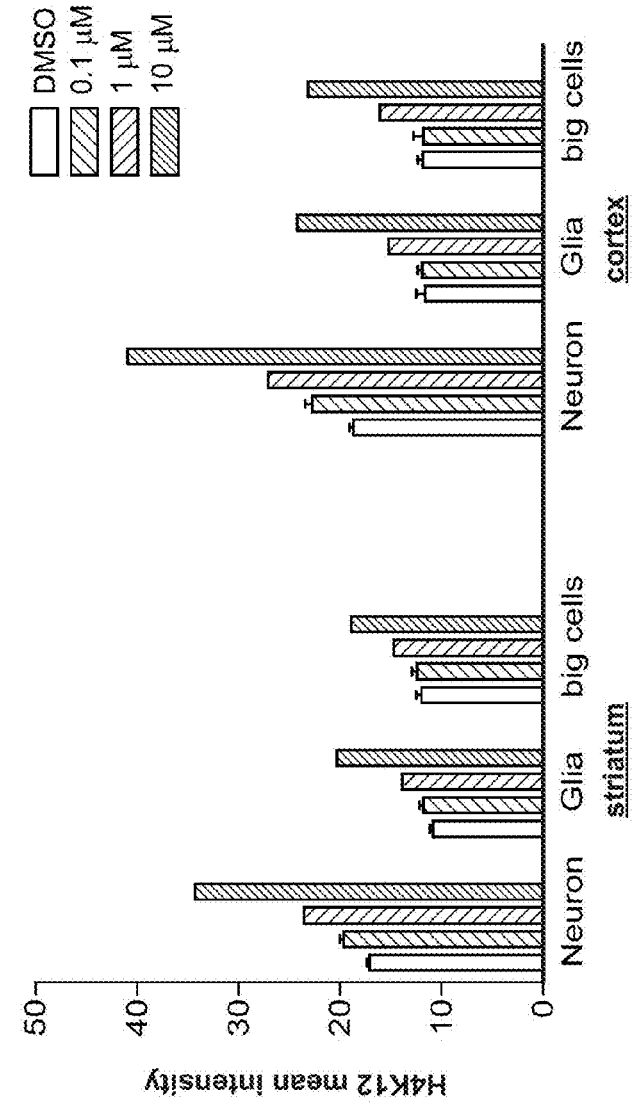
Figure 15:
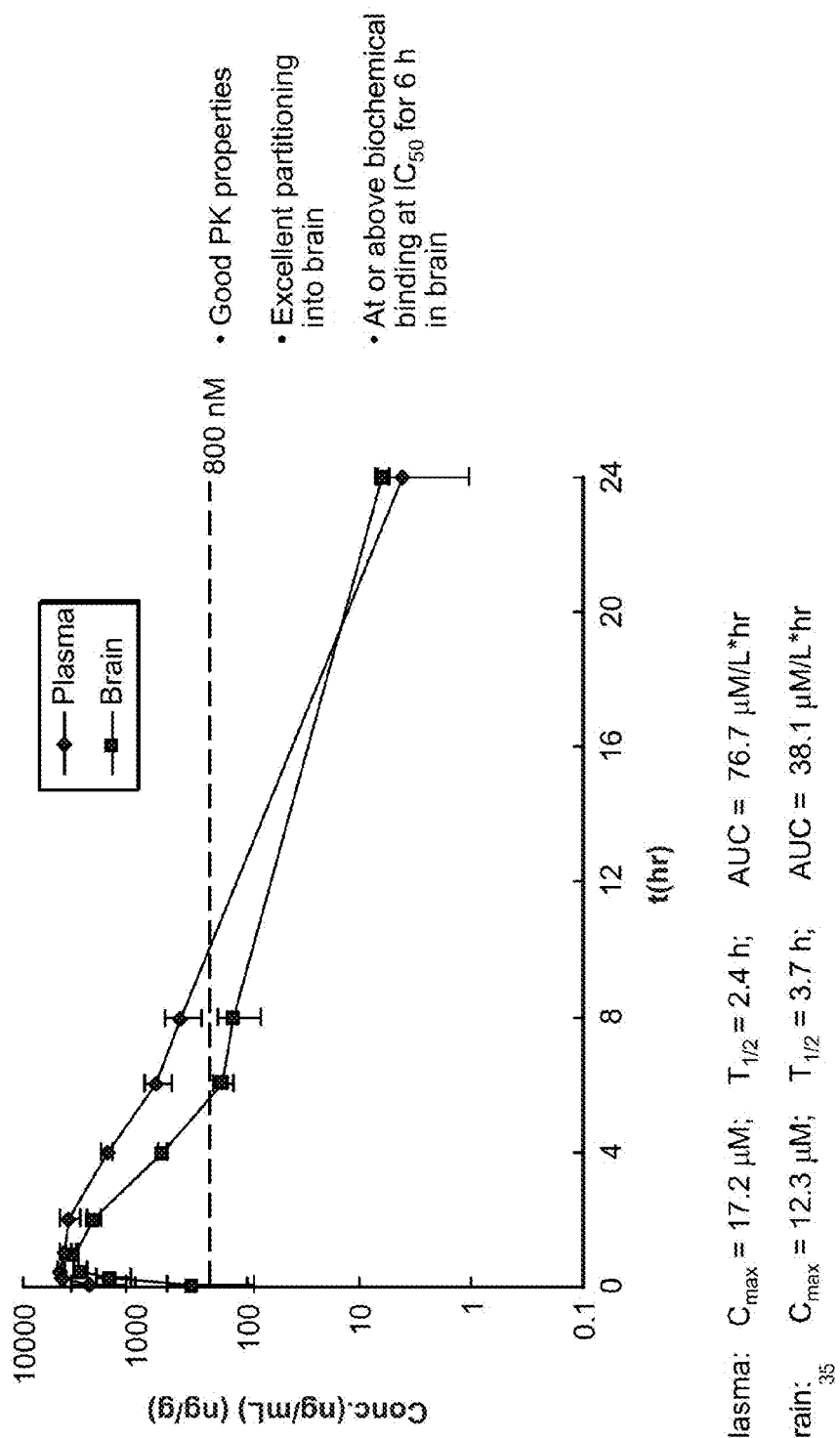
FIG. 15 is a summary of the pharmacokinetic data after a single dose of 30 mg/kg CI-994 administered systemically via intraperitoneal injection. The concentration time curve for CI-994 in the plasma and brain of C-57 mice from 5 min to 24 h is shown. This data demonstrates the large concentration of CI-994 achieved in brain and plasma. The brain Cmax (12.3 uM) and the AUC (38.1 uM) levels are well above effective in vitro concentrations. CI-994 readily crosses the blood-brain barrier.
Figure 16:
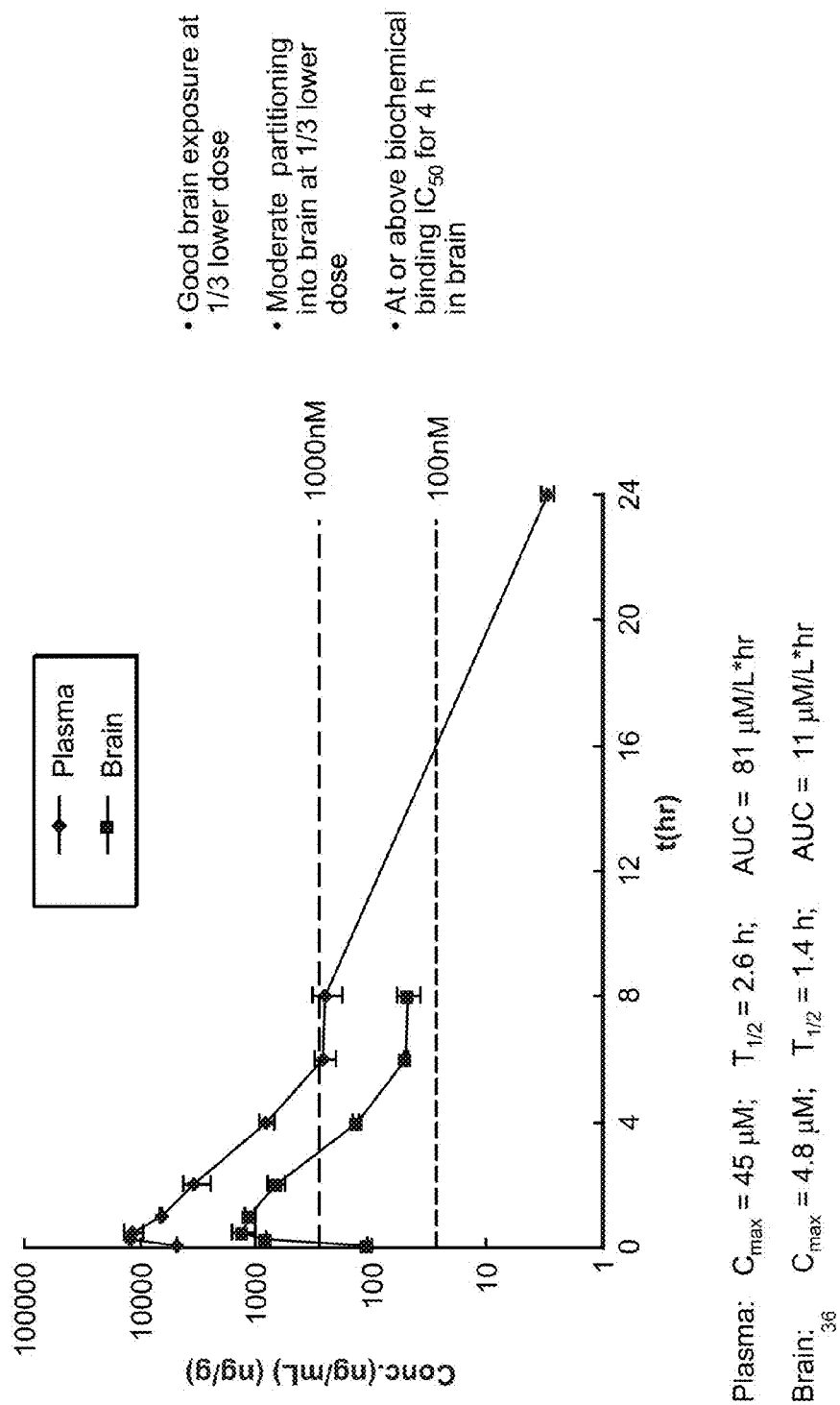
FIG. 16 is a summary of the pharmacokinetic data after a single dose of 10 mg/kg CI-994 administered systemically via intraperitoneal injection. The concentration time curve for CI-994 in the plasma and brain of C-57 mice from 5 min to 24 h is shown. This data demonstrates the large concentration of CI-994 achieved in brain and plasma. The brain Cmax (4.8 uM) and the AUC (11 uM) levels are well above effective in vitro concentrations. CI-994 readily crosses the blood-brain barrier at this lower dose.
Figure 17:
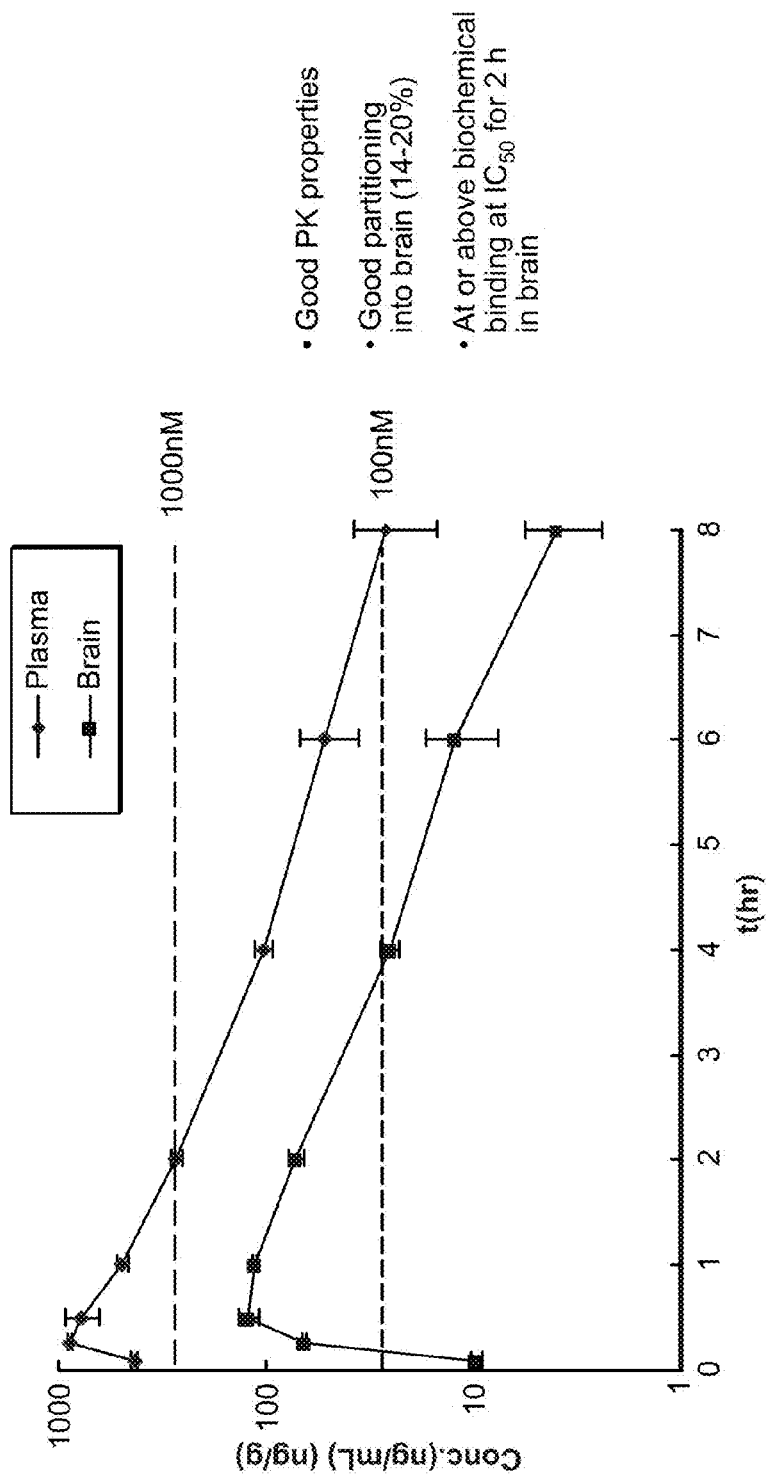
FIG. 17 is a summary of the pharmacokinetic data after a single dose of 1 mg/kg CI-994 administered systemically via intraperitoneal injection. The concentration time curve for CI-994 in the plasma and brain of C-57 mice from 5 min to 8 h is shown. This data demonstrates even at low doses administered systemically there are significant levels of CI-994 in brain and plasma. The brain Cmax (0.45 uM) and the AUC (1.2 uM) levels are near effective in vitro concentrations. It is not obvious what the necessary exposure requirements in the brain are that will correlate with a behavioral phenotype associated with improved memory. This demonstrates that CI-994 at low doses and exposure is just as effective as doses and exposures that are 20-30 fold higher.
Figure 18:
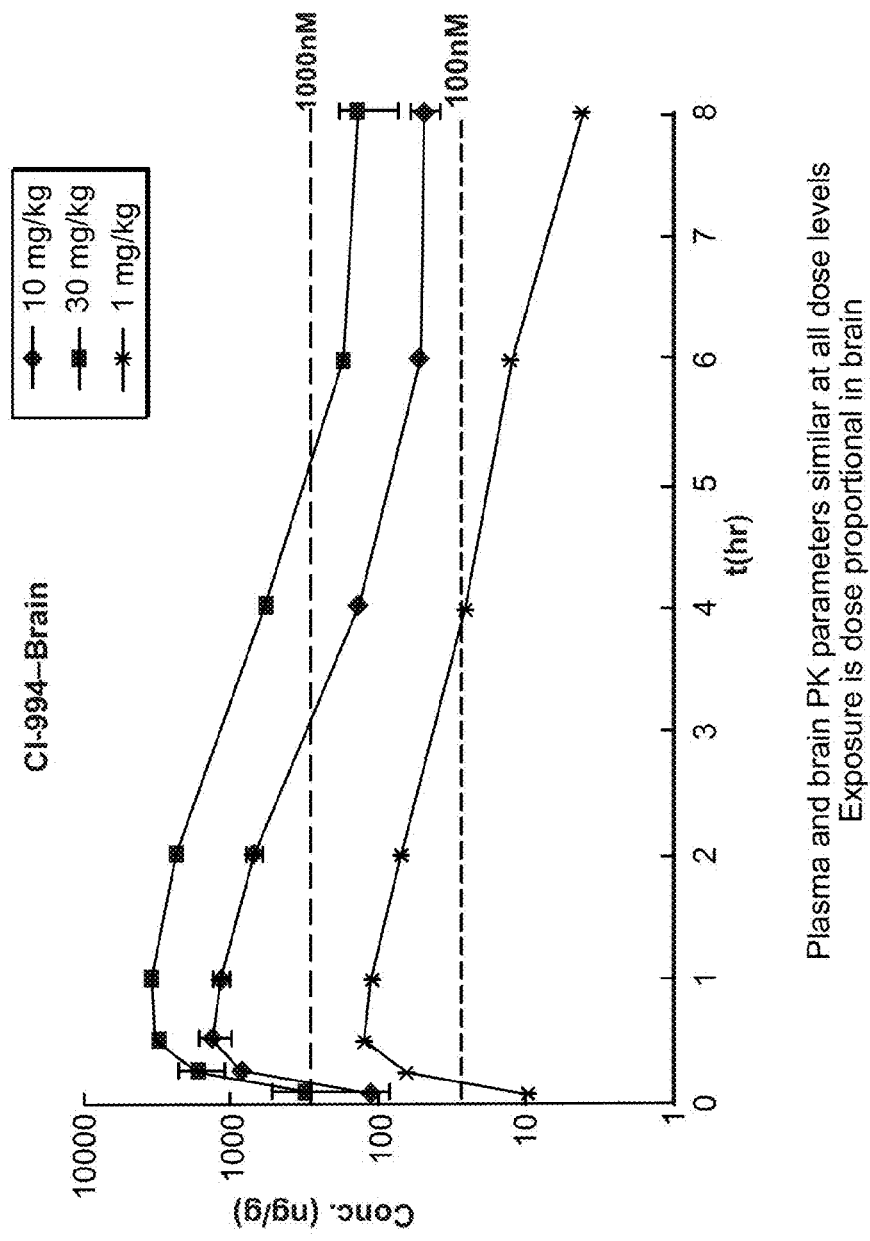
FIG. 18 is a summary of the concentration time curve in mouse brain after a single dose at 30, 10 and 1 mg/kg CI-994 administered systemically via intraperitoneal injection. Brain exposure is dose proportional across these dose levels. All three exposure profiles have been shown to be efficacious in subsequent in vivo models of memory. This data is defining the optimal and minimal exposure needed for efficacy in CNS related indications which to our knowledge had not been reported before.
Figure 20A:
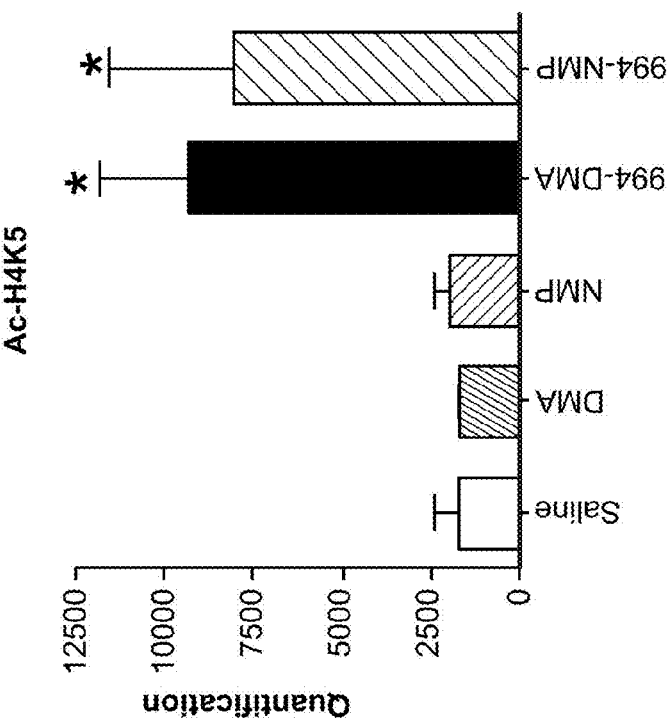
FIG. 20 shows that acute treatment with CI-994 increases histone acetylation in whole brain. A. CI-994 was formulated in several different excipient combinations and dosed at 30 mg/kg via intraperitoneal injection. At 1 h post dose, brains were fixed and analyzed via western blot analysis for the effects on H4K5 acetylation. B. The quantified histograms demonstrate that CI-994 when formulated in either 5% DMA/45% PEG 400/50% saline or 5% NMP/30% 45% PEG 400/60% saline causes changes in the brain histone acetylation levels. PEG—polyethylene glycol; DMA—Dimethylacetamide; NMP—N-methylpyrrolidinone.
Figure 20B:
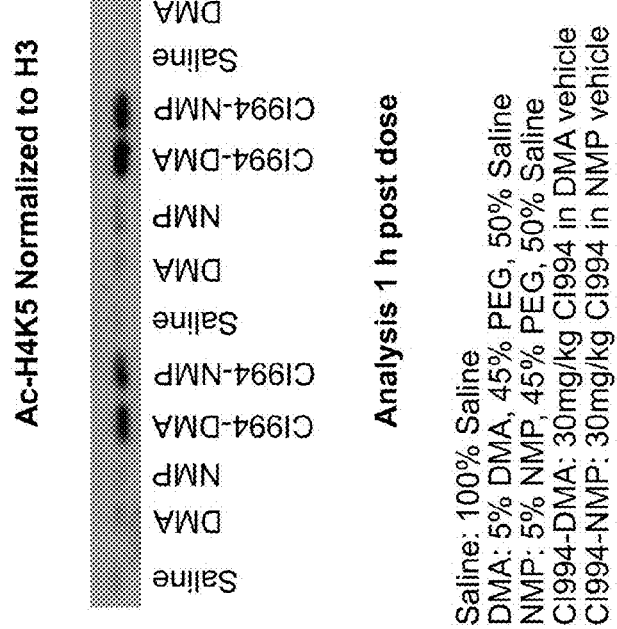

Functional measures of CI-994's cellular HDAC activity (Immunoflourescent analysis)
Materials and Methods:
Immunofluorescent detection of histone acetylation level changes in culture neurons was performed as follows:
Day 1:
1) Compounds were pin transferred from 384-well plates (Abgene) using a 185 nl pin tool using a no touch bottom protocol.
Day 2: After ~24 Hour Compound Treatment—
1) Media was aspirated using a plate washer (Tecan) protocol that leaves ~5 ul residual volume and without touching the bottom of plates); or alternatively, wells were gently aspirated to remove media with 12-channel aspirator wand.
2) A multichannel pipet or use liquid handling system (e.g. Combi, standard tubing; slow speed) was used to add 75 ul formaldehyde (4% in PBS) and wells incubated 10 min at room temperature.
3) Formaldehyde was aspirated and cells rinsed 3 times with 100 ul PBS;
4) PBS was aspirated and 100 ul blocking/permeablization buffer (0.1% Triton-X100, 2% BSA, in PBS) added and wells incubate 1 hour at room temperature.
5) Blocking buffer was aspirated and 50 ul primary antibody diluted 1:500 in blocking buffer was added and wells incubated overnight at 4 degrees.
Day 3:
1) Primary antibody was aspirated and wells rinsed 3 times with 100 ul blocking buffer
2) 50 ul of secondary antibody diluted 1:500 and with Hoeschst (1:1000 from 10 mg/mL (16 mM) stock) added and wells incubated 1.5 hours at room temperature covered in foil to prevent photobleaching.
3) Wells were rinsed 3 times with 100 ul PBS, and a 100 uls of PBS added and the plates, sealed
4) Plates were then read on Acumen/IX Micro
5) Plates were stored at 4 degrees.
Results:
CI-994 at 1 and 10 uM caused an increase in H4K12 acetylation and H2B tetra-acetylation after 6 h incubation in brain region specific primary cultures (cortex and striatum). CI-994 was able to functionally inhibit HDAC enzymes at relative low dose and caused an increasing functional response at increasing doses (FIGS. 10, 11 and 12).

Example 4

Increase in Acetylation Marks in Brain Specific Regions Related to Learning and Memory after Acute Dosing Materials and Methods:
The experimental protocol for acute treatment with CI-994 and the corresponding effects on histone acetylation in brain specific regions of adult mice is shown in FIG. 21. Crude Protein Lysis for western blot analysis of specific brain sections was prepared as follows:
1. For dissected, frozen brain tissue:
a. On ice, thaw frozen tissue and immediately homogenize carefully in 250 uL of ice-cold Suspension Buffer.

(100 uL was used for tissue approx. 2-3 mm3; adjust as needed)

1.5 mL disposable pestles (Fisher cat#03-392-100)

b. As soon as possible, add an equal volume of 2×SDS gel-loading buffer, pipetting up and down to mix.

2. Place the sample at 95° C. for 5 min.

3. Shear viscous chromosomal DNA by smoothly passaging through 23-25 gauge hypodermic needle (2-3×) or by sonicating briefly (Al used the needle method and it worked fine). Avoid foaming/bubbles.

4. Centrifuge the sample at 10,000 g for 10 min at room temperature, transferring supernatant to fresh tube.

5. Aliquot sample as needed based on protein concentration.

Suspension Buffer:

0.1M NaCl, 0.01M TrisCl (pH 7.6), 0.001M EDTA (pH 8.0) (buffer to this point can be prepared ahead, room temp. storage) Just before use, add: 1× phosphatase/protease inhibitor cocktail (ex. ThermoFisher "HALT," cat#78440)

5 mM Sodium Butyrate (HDAC inhibitor).

2×SDS gel-loading Buffer:

100 mM TrisCl (pH 6.8), 4% SDS, 20% glycerol (buffer to this point can be prepared ahead, room temp. storage) Just before use, add: 200 mM dithiothreitol (from 1M stock) 5 mM Sodium Butyrate (HDAC inhibitor)

Figures 23A, 23B:
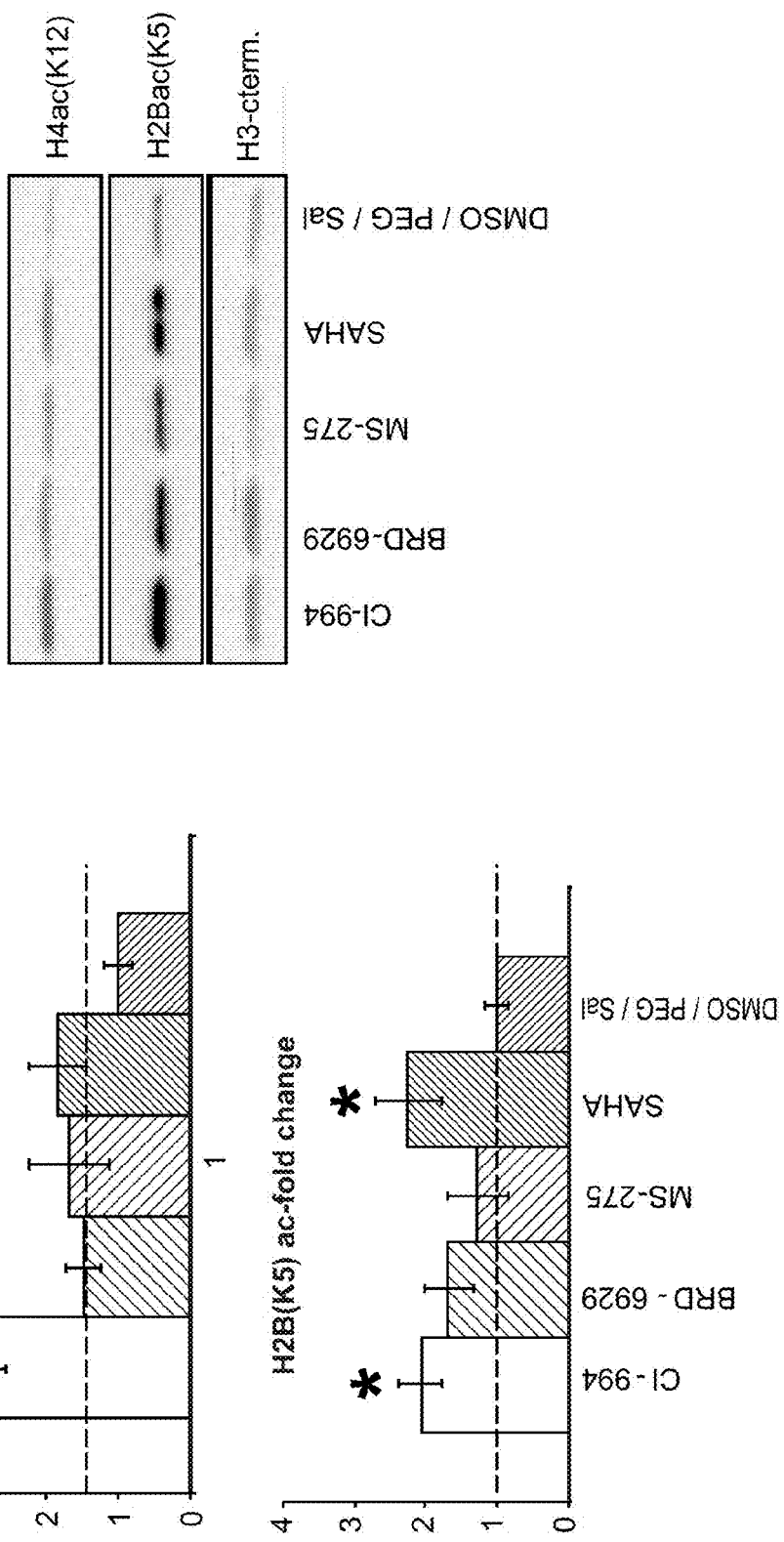
FIG. 23 demonstrates that acute treatment with CI-994 increases the levels of acetylation of H4K12 and H2B5. In cortex after 1 hour, CI-994 caused a 2-3 fold increase in the acetylation levels for H4K12 and H2BK5. In the case of H4K12 this effect is unique to CI-994 under these conditions.

Results:

Acute treatment with CI-994 caused a significant increase in the levels of H4 and H2B (tetra) histone acetylation in the cortex of adult mice. This is unique to CI-994 as other known HDAC inhibitors fail to produce an effect in this brain region for these specific marks under these conditions (FIG. 22). CI-994 also increases the acetylation on specific single histone loci in the cortex (H4K12 and H2BK5). In the case of H4K12, the effect is unique to CI-994 under these conditions (FIG. 23).

Figure 24:
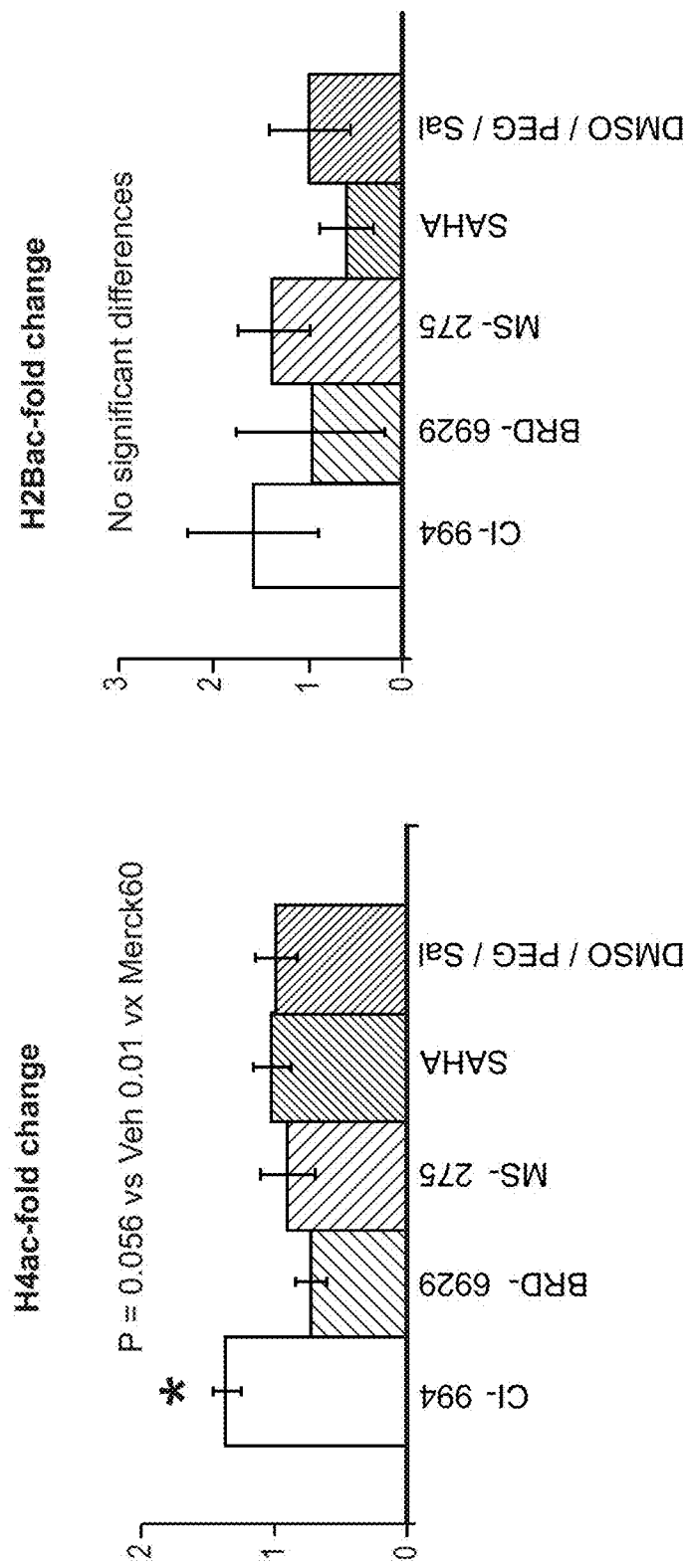
FIG. 24 demonstrates that acute treatment with CI-994 caused an increase in the acetylation levels of tetra acetylated H4 in the hippocampus of adult male mice. In hippocampus, 1 hour after the administration of CI-994, there was a 2-3 fold increase in the acetylation levels for tetra-acetylated H4. There was no effect in the hippocampus in this experiment on the levels of tetra-acetylated H2B.
Figure 25:
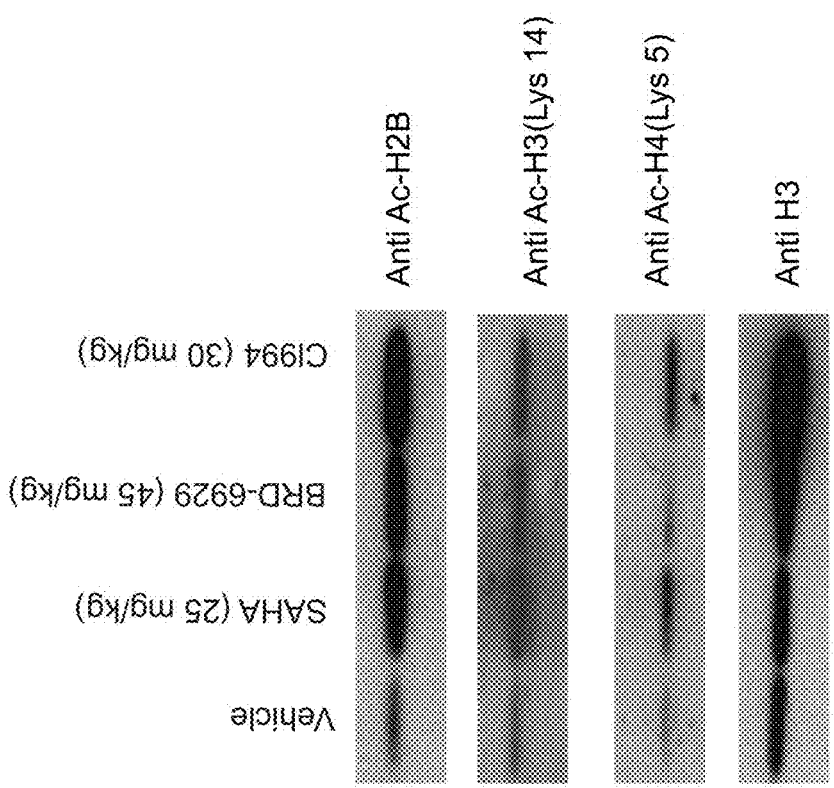
FIG. 25 shows that chronic administration of CI-994 enhances histone acetylation in whole brain. Western gel analysis demonstrates that even after chronic administration of CI-994, every day for 10 days, CI-994 can still exert and effect on acetylation levels in the brains of mice. The western blot shows an increase in tetra-acetylated H2B and acetylated H4K5 relative to the vehicle control.

Acute treatment with CI-994 also caused an increase in the acetylation levels of tetra acetylated H4 in the hippocampus of adult male mice. No effect was observed on the levels of tetra-acetylated H2B in the hippocampus (FIG. 24).

Example 5

Behavioral Data in Mice—Phenotypes that Correspond to Improved Memory and Cognition Materials and Methods:

C57/BL6 WT mice were injected with vehicle or HDAC inhibitor for 10 days. On day 11, mice were trained in contextual fear conditioning paradigm (Training consisted of a 3 min exposure of mice to the conditioning box (context, TSE) followed by a foot shock (2 sec, 0.8 mA, constant current). One hour after training, mice were injected with the HDAC inhibitor or vehicle. On day 12 mice were returned to the training box and the freezing behavior were monitored and recorded.

Figure 26:
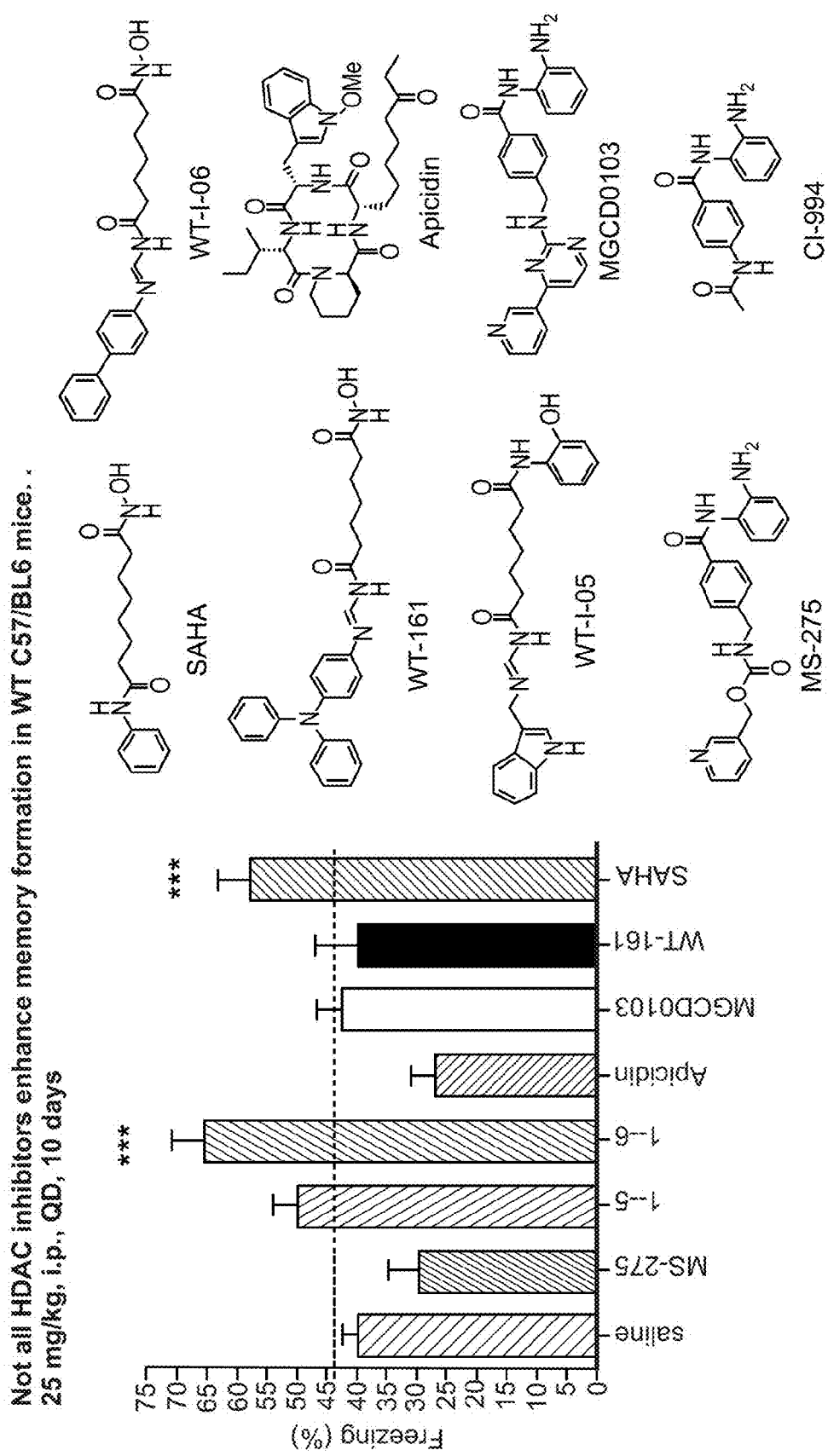
FIG. 26 demonstrates that several chemical classes of HDAC inhibitors are ineffective at increasing the memory of mice as measured by % freezing in a contextual fear conditioning paradigm.

Results:

Several chemical classes of HDAC inhibitors are ineffective at increasing the memory of mice as measured by % freezing in a contextual fear conditioning paradigm. It is not obvious which compounds will be efficacious based on their ability to inhibit the HDAC enzyme in vitro. More importantly, this data shows that other compounds form the same benzamide chemical class as CI-994 (MS-275 and MGCD0103) are not efficacious in this model under these conditions (FIG. 26).

Figure 27:
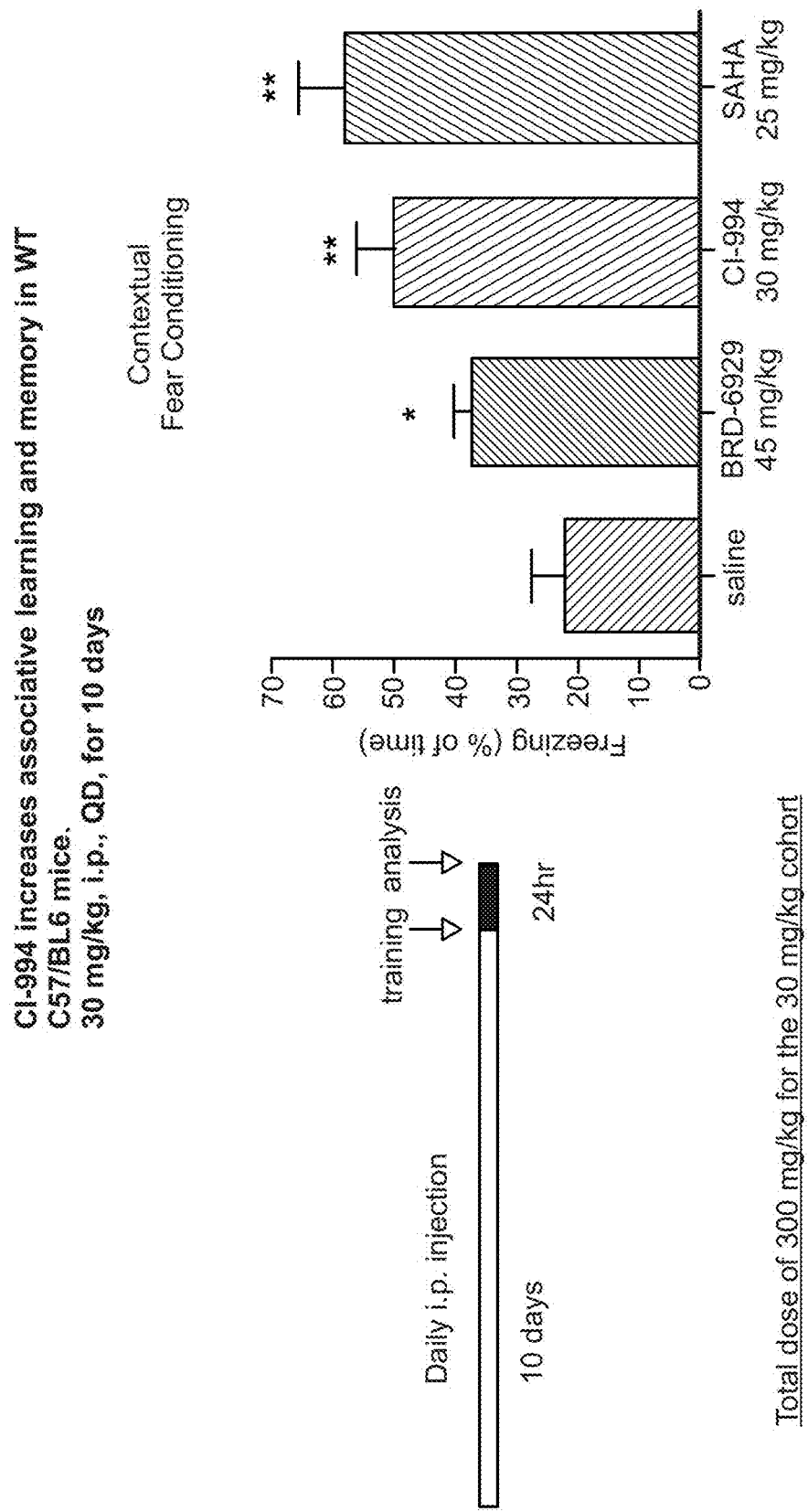
FIG. 27 demonstrates that a 30 mg/kg dose of CI-994 given every day for 10 days improves the memory of mice in a contextual fear conditioning paradigm as measured by % time freezing.

FIG. 27 demonstrates that a 30 mg/kg dose of CI-994 given every day for 10 days improves the memory of mice in a contextual fear conditioning paradigm as measured by % time freezing. It is as effective as SAHA, the efficacy of which has been reported. To our knowledge, this effect has not been reported previously for CI-994 or for this class of compounds under any conditions. It is not obvious that this compound or this class would be efficacious based on the data shown in FIG. 26.

Figure 28:
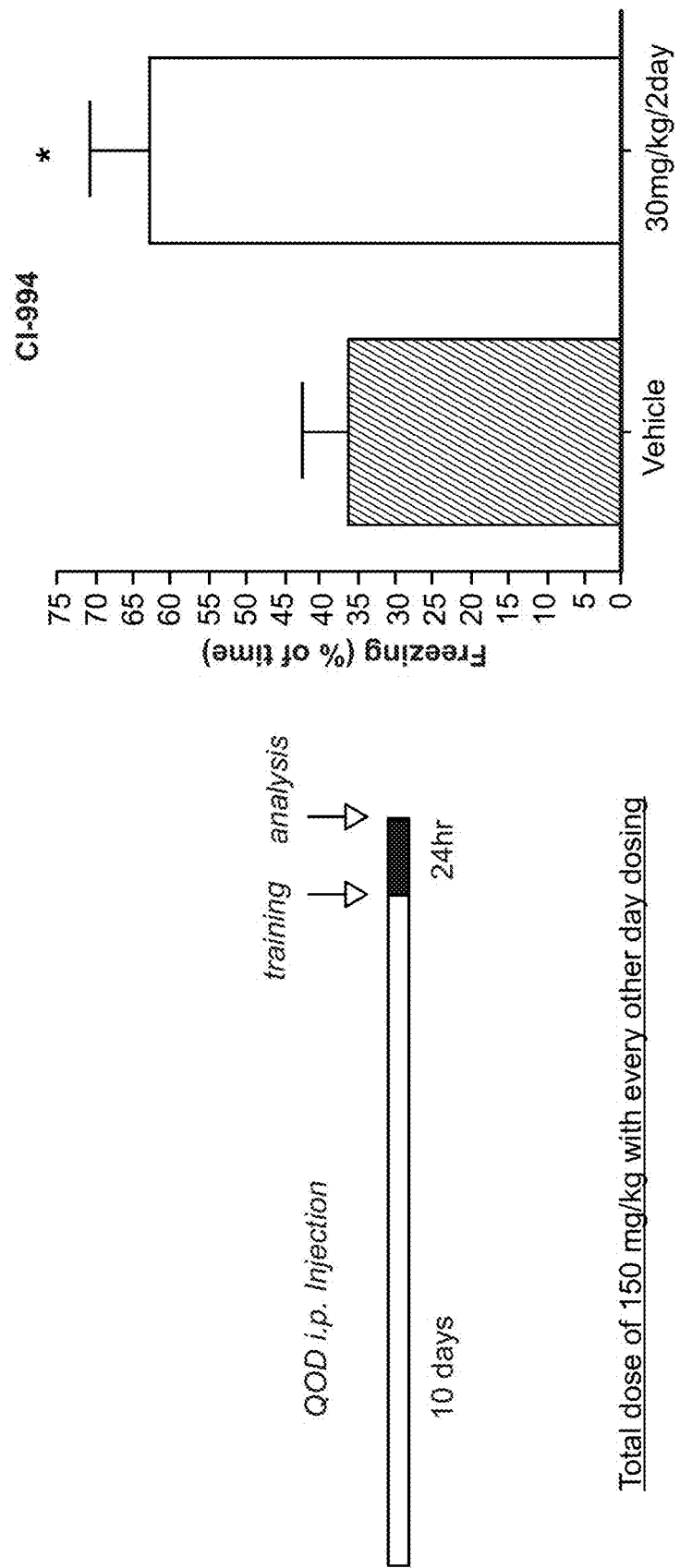
FIG. 28 shows that CI-994 is equally effective in this model of memory using an alternate day dosing schedule at the same 30 mg/kg dose. The effective total dose was reduced by 50% and retained efficacy.

CI-994 is also equally effective in this model of memory using an alternate day dosing schedule at the same 30 mg/kg dose (FIG. 28). CI-994 is also equally effective in this model using every day and alternate day dosing schedule at low doses of 1 mg/kg dose. We have lowered the effective total dose by 50% and retained efficacy. It was not obvious that this dosing paradigm should be effective or what would be the optimal dosing schedule. An efficacious every other day dosing schedule with CI-994 or any other HDAC inhibitor has to our knowledge not been reported. It is/was not obvious that this dosing schedule would work with CI-994, that this schedule could be extended to other members of this chemical class of HDAC inhibitors or with other chemical classes of HDAC inhibitors.

Figure 29:
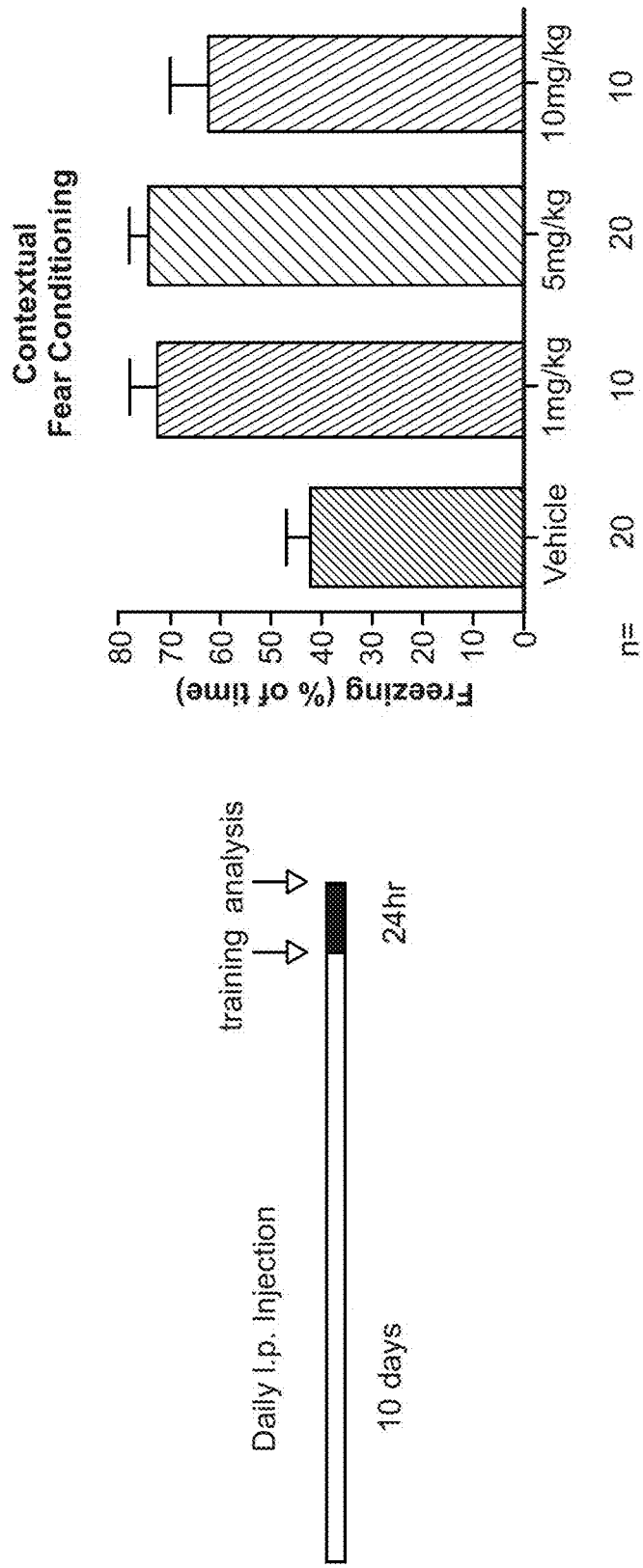
FIG. 29 shows a dose response study examining lower doses of CI-994 following the same every day for 10 days dosing schedule. The histograms demonstrate, CI-994 is efficacious as a memory enhancer at all doses; 10, 5, and 1 mg/kg.

A dose response study examining lower doses of CI-994 following the same every day for 10 days dosing schedule demonstrated that CI-994 is efficacious as a memory enhancer at all doses; 10, 5, and 1 mg/kg. At the low dose of 1 mg/kg, the total dose required over the 10 day dosing period is 10 mg/kg (FIG. 29). There have been no reports describing this with CI-994 or any other HDAC inhibitor at such low doses.

Example 6

CI-994 Rescues the Cognitive Defects in the Rubinstein-Taybi Mouse Model

Materials and Methods:

CBP mutant mice (B6.Cg-Tg(Camk2a-Crebbp*)1364Tabe/J) were obtained from Jackson lab. Expression of this FLAG-epitope tagged, dominant negative truncation of the CREB-binding protein (FLAG-CBPA1, lacking the coding sequence for amino acids 1084-2441) is spatially directed to neurons in the forebrain (hippocampus, amygdala, striatum, and cortex) and temporally directed to postnatal development by the CaMKIIα promoter. This dominant negative mutant form of CBP (designed to interrupt transcription factors utilizing CBP as a coactivator for the expression of their target genes) is expressed from the transgene at 95% of endogenous CBP levels in the hippocampus and 84% of endogenous CBP levels in the cortex. Hemizygous mice exhibit hippocampus-dependent memory deficits (such as reduced long-term potentiation, defective spatial learning, and impaired contextual fear conditioning) with none of the developmental impairments observed in CBP-deficient mutant models. We injected CBP mutant hemizygous mice and their control littermates with vehicle or CI-994 for 10 days. On day 11, mice were trained in contextual fear conditioning paradigm (Training consisted of a 3 min exposure of mice to the conditioning box (context, TSE) followed by a foot shock (2 sec, 0.8 mA, constant current). One hour after training, mice were injected with CI-994 or vehicle. On day 12 mice were returned to the training box and the freezing behavior were monitored and recorded.

REFERENCES

Figure 30:
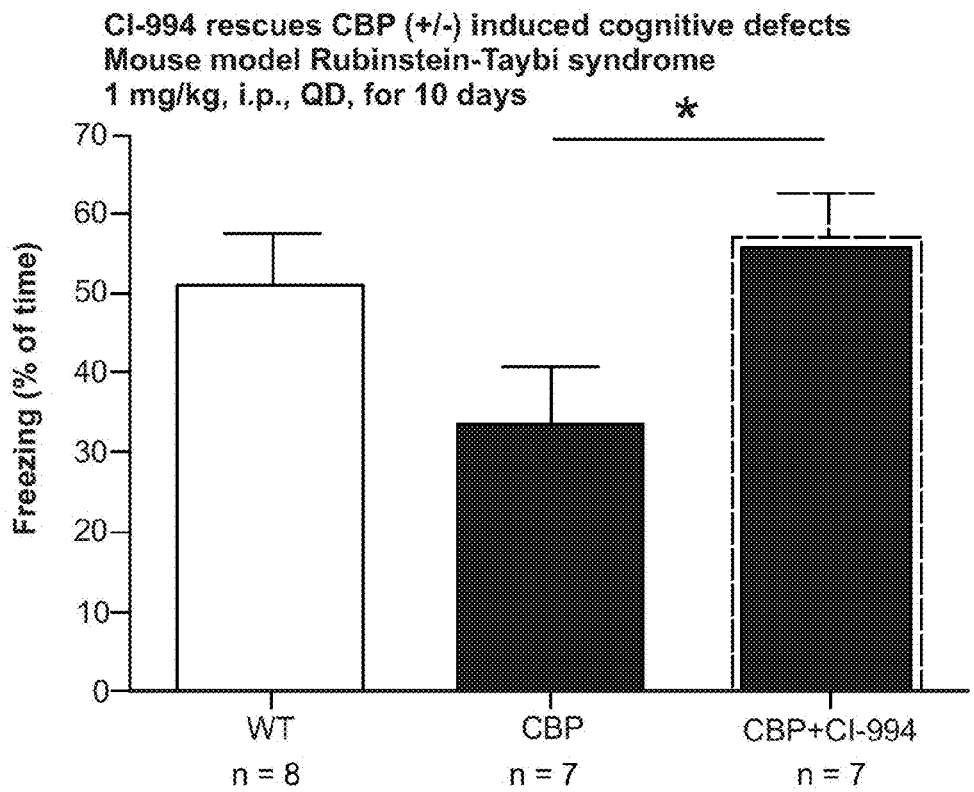
FIG. 30 shows that CI-994 was able to rescue the induced cognitive defects seen in the $CBP^{+/-}$ mouse model of Rubinstein-Taybi syndrome. At a low dose of 1 mg/kg dosed every day for 10 days, CI-994 restores the memory of these mice to an equivalent level as found in the wild-type littermates.

Learn Mem. 2005 March-April; 12(2):111-9. Transgenic mice expressing a truncated form of CREB-binding protein (CBP) exhibit deficits in hippocampal synaptic plasticity and memory storage. Wood M A, Kaplan M P, Park A, Blanchard E J, Oliveira A M, Lombardi T L, Abel T Results:

CBP (+/−) heterozygous mice represent a model of the human disease syndrome of Rubinstien Taybi. It is the same genetic mutation which is believed to be casual in humans. People affected by this syndrome have memory/cognition and developmental deficits. Using our standard dosing paradigm (1 mg/kg, QD, 10 days) CI-994 restores the memory of these mice to an equivalent level as found in the wild-type littermates. The effect of CI-994 was highly significant at this low dose of 1 mg/kg (FIG. 30).

Example 7

CI-994 Rescues p25/CK Induced Cognitive Defects in the Alzheimer's Disease Mouse Model Materials and Methods:

CK/p25 mouse is an inducible neurodegenerative disease mouse model. The bitransgenic mice were created by crossing the CamK2a-tTA and the tetO-p25 Tg mouse lines. In the presence of doxycyclin, the expression of p25 is suppressed. When doxycyclin is removed, the expression of p25 is strongly induced in the forebrain. Six weeks of p25 induction causes massive neuronal loss, elevated beta-amyloid peptide production, tau associated pathology, and impairment in learning and memory. For these experiments, doxycyclin was removed from 3-month old CK/p25 mice and the control littermates for 6 weeks. The mice were subsequently injected with CI-994 or vehicle for 10 days. On day 11, mice were trained in contextual fear conditioning paradigm (training consisted of a 3 min exposure of mice to the conditioning box (context, TSE) followed by a foot shock (2 sec, 0.8 mA, constant current). One hour after training, mice were injected with CI-994 or vehicle. On day 12 mice were returned to the training box and the freezing behavior were monitored and recorded.

REFERENCES

Cruz J C, Tseng H-C, Goldman J A, Shih H, Tsai L-H. Aberrant Cdk5 activation by p25 triggers pathological events leading to neurodegeneration and neurofibrillary tangles. Neuron 2003, 40:471-483.

Fischer A, Sananbenesi F, Pang P T, Lu B, Tsai L-H. Opposing roles of transient and prolonged expression of p25 in synaptic plasticity and hippocampus-dependent memory. Neuron, 2005, 48: 825-838.

Fischer A, Sananbenesi F, Wang X, Dobbin M, Tsai, L-H. Recovery of learning and memory is associated with chromatin remodeling. Nature 2007, 447: 178-182.

Figure 31:
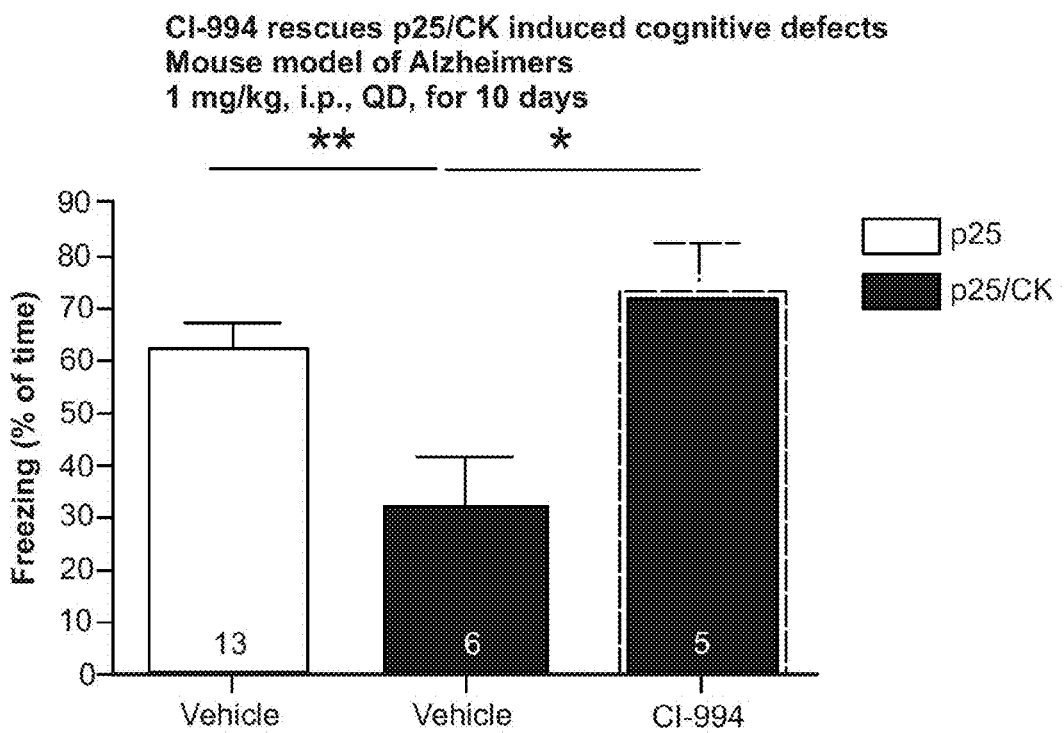
FIG. 31 shows that CI-994 rescues p25/CK induced cognitive defects in the mouse model of Alzheimer's disease. At a low dose of 1 mg/kg dosed every day for 10 days, CI-994 is able to rescue the cognitive defects in this mouse model of Alzheimer's disease. The numbers in each column represent the number of mice in each cohort. The p25 vehicle group represent non-induced vehicle treated mice, the p25/CK vehicle group represent the induced untreated mice. The control group consisted of the tetO-p25 Tg mice fed on normal diet, which did not express p25.

Results:

At a low dose of 1 mg/kg dosed every day for 10 days, CI-994 was able to rescue the cognitive defects in this mouse model of Alzheimer's disease (FIG. 31). The p25 vehicle group represent non-induced vehicle treated mice, the p25/CK vehicle group represent the induced untreated mice. The control group consisted of the tetO-p25 Tg mice fed on normal diet, which did not express p25.

It is remarkable that even after massive neuronal loss, 1 mg/kg of CI-994 treatment was able to restore contextual fear conditioning learning. The brain pathology of p25 is reminiscent of human patients with neurodegeneration and memory impairment. Thus, the beneficial effects of CI-994 in the CK/p25 model provide promise for treating human patients (with Alzheimer's disease and other dementias) with CI-994 to improve their cognitive functions.

Example 8

CI-994 Facilitates Memory Formation and Fear Extinction

Materials and Methods:

Mice were trained using contextual fear conditioning paradigm on day 0. (Training consisted of a 3 min exposure of mice to the conditioning box (context, TSE) followed by three foot shocks (2 sec, 0.8 mA, constant current with 15-seconds-intervals). From day 1, mice were trained in extinction trials. For each training day, mice were twice exposed to the conditioning box for 3 min without foot shock (two extinction trials/day). One hour after the first trial, mice were injected with CI-994 (30 mg/kg, i.p.). One hour after the injection, the second extinction trial was performed. The freezing time in each individual trial was measured.

Figure 34:
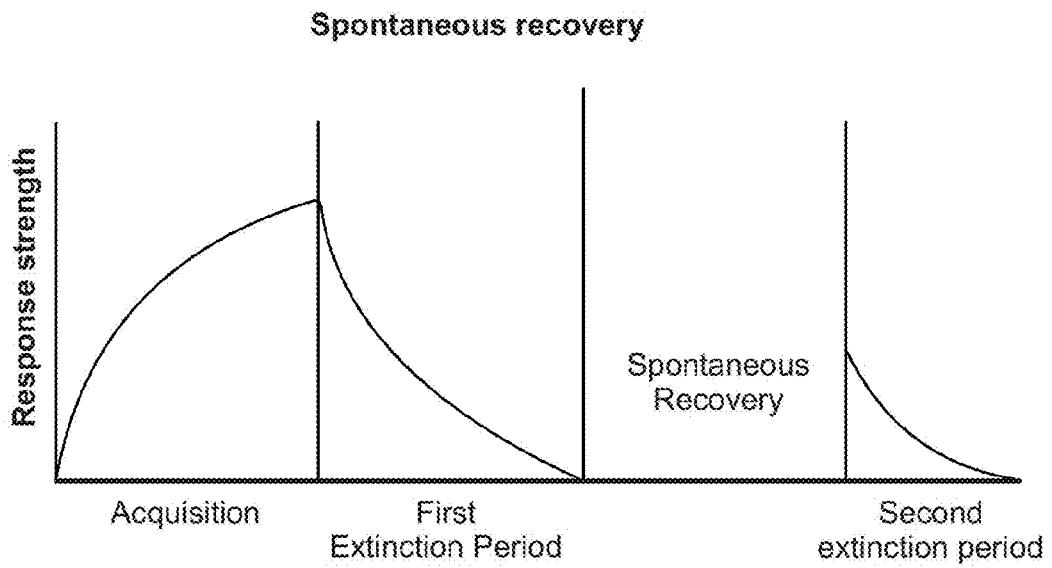
FIG. 34 demonstrates that after the fear memory extinction trials, fear memory will spontaneously recover after resting in the home cage for a period of time.

For the memory reconsolidation paradigm, after the fear extinction training as described above, mice were housed in the home cage for one month. Mice were subsequently re-exposed to the conditioning box for 3 min, their freezing behavior measured. It is well established that after the fear memory extinction trials, fear memory will spontaneously recover after resting in the home cage for a period of time (FIG. 34). The speculated mechanism for fear extinction is to trigger the formation of new memory which competes with fear memory and in turn reduces the fear response. Conversely, reconsolidation based fear memory extinction paradigm has been proposed to directly modify the activated fear memory, so that the reduced fear response does not spontaneously recover (Extinction-reconsolidation boundaries: key to persistent attenuation of fear memories. Monfils M H, Cowansage K K, Klann E, LeDoux J E. Science. 2009 May 15; 324(5929):951-5. Epub 2009 Apr. 2).

Results:

Interestingly, WT mice received CI-994 treatment extinct significantly faster than the vehicle treated group. Importantly, CI-994 treatment ameliorated the impairment of fear memory extinction in HDAC2 overexpression mice. After 5 extinction trials, the freezing level of CI-994 treated HDAC2OE mice declined to 30% while vehicle treated HDAC2 overexpressing mice continued to exhibit high level of freezing behavior (70%). Thus, CI-994 was effective in another distinct form of memory formation. Additionally, CI-994 was effective in an acute dosing setting. The rescue of the HDAC2 overexpressing mice is achieved with 2 doses of CI-994 at 30 mg/kg over the course of 5 days (FIG. 33).

We have now demonstrated several dosing paradigms in terms of frequency and dose in multiple disease states. These experiments suggest that CI-994 treatment is beneficial for extinction of aversive memories. Thus, this treatment has promise in treating phobias, stress disorders including post-traumatic stress disorder (PTSD) and emotional disorders.

Figure 35:
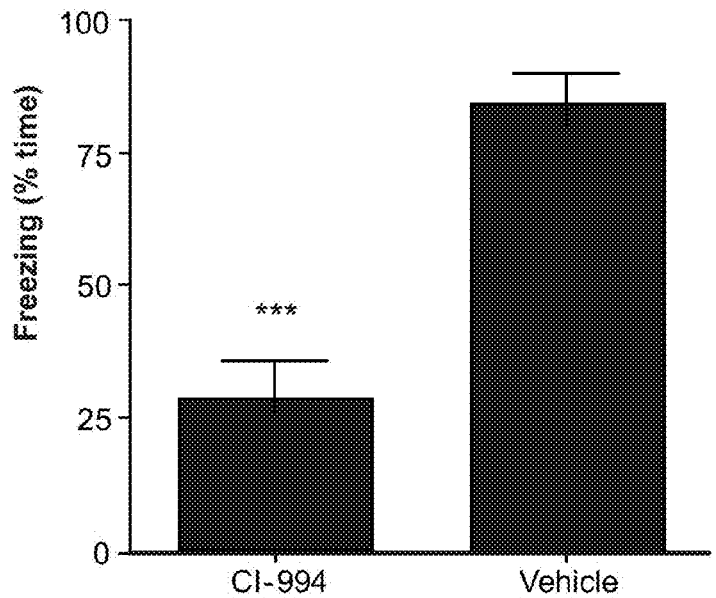
FIG. 35 shows that CI-994 treatment significantly reduced the freezing levels of HDAC2 overexpression mice compared to mice treated with vehicle after one month of spontaneous recovery.

For the memory reconsolidation paradigm, CI-994 treatment significantly reduced the freezing levels of HDAC2 overexpression mice compared to mice treated with vehicle after one month of spontaneous recovery (FIG. 35). These findings highlight the potential of treating PTSD in humans with CI-994. The data also suggests that proper training paradigm in conjunction with CI-994 treatment can lead to permanent erasing of fear memory.

Example 9

Synthesis, Characterization and Formulation of CI-994 and Dinaline

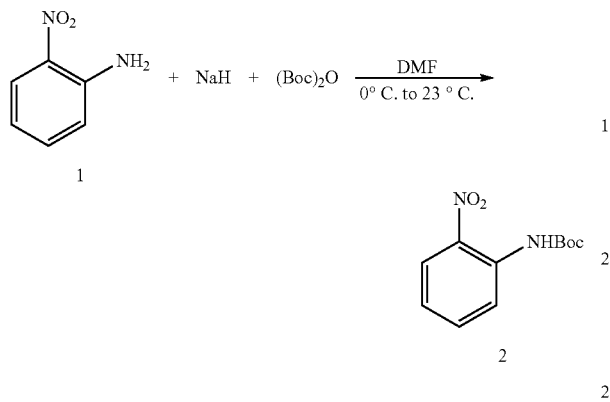

2-nitroaniline 1 (25 g, 182.4 mmol, 1.0 eq.) was dissolved in dry-DMF (400 mL) and cooled to 0° C. 60% NaH (7.7 g, 200.7 mmol, 1.1 equiv.) was added slowly to the reaction mixture under argon atm. After 30 min, (Boc)$_2$O (47 mL, 218.8 mmol, 1.2 eq) dissolved in dry DMF (100 mL) was added slowly to the reaction mixture at that temperature. The reaction mixture was slowly brought to 23° C. and further stirred for 5 h. After the completion of the reaction, the reaction mixture was poured into ice-water and the precipitated solid was filtered, washed with water (3×100 ml) and dried. The material was passed through short pad of silica gel column to provide tert-Butyl-2-nitrophenylcarbamate 2 as a pale yellow solid.

Yield=24 g (55%).
TLC/Rf=0.6 (20% EtOAC in hexane)
$^1$H NMR (DMSO-d$_6$, 500 MHz) δ 9.58 (s, 1H), 7.95 (d, 1H, J=8.5 Hz), 7.67 (d, 2H, J=4 Hz), 7.30-7.26 (m, 1H), 1.45 (s, 9H).

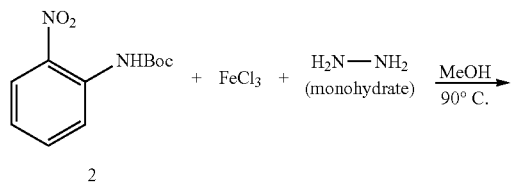

tert-Butyl-2-nitrophenylcarbamate 2 (24 g, 100 mmol, 1 eq), FeCl$_3$ (1 g, 5.57 mmol, 0.06 eq), hydrazine monohydrate (150 mL) and MeOH (440 mL) were combined and heated to 90° C. After vigorously stirring for 2-3 h, the reaction mixture was hot filtered through celite and washed with EtOAc. The filtrate was concentrated under vacuum to remove EtOAc-MeOH. This crude residue was diluted with cold water and the resultant solid was filtered and washed with hexane to afford tert-butyl 2-aminophenyl carbamate 3 as an off-white solid.

Yield 3: (19 g, 91% yield).
TLC: O.K, Rf=0.4 (30% EA in Hexane).
$^1$H NMR (DMSO-d$_6$, 500 MHz) δ8.25 (br s, 1H), 7.17 (d, 1H, J=7.5 Hz), 6.82 (t, 1H, J=7.5 Hz), 6.67 (d, 1H, J=8.0 Hz), 6.51 (t, 1H, J=7.5 Hz), 4.80 (s, 2H), 1.45 (s, 9H). MS: 109 [M-Boc+H]$^+$.

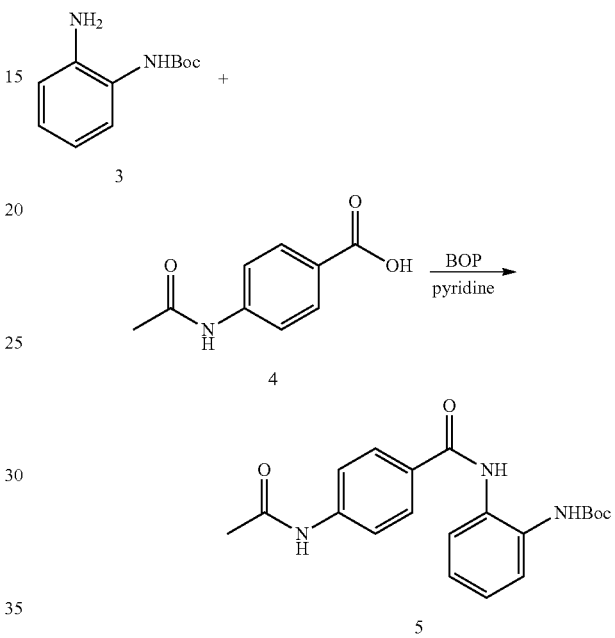

tert-butyl 2-aminophenyl carbamate 3 (19 g, 91.7 mmol, 1 equiv.), 4-acetamido benzoic acid 4 (18 g, 100 mmol, 1.1 equiv.), and BOP (48.2 g, 109 mmol, 1.2 equiv.) were dissolved in pyridine (100 mL). After stirring at 23° C. for 48 h, the reaction mixture was added to water, stirred and the resultant precipitate solid was filtered, washed with water, ether and dried under vacuum to provide benzamide 5.

Yield=30 g (90%).
TLC/Rf=0.5 (100% EtOAC)
$^1$H NMR (DMSO-d$_6$, 500 MHz) δ10.23 (s, 1H), 9.73 (s, 1H), 8.66 (s, 1H), 7.90 (d, 2H, J=8.0 Hz), 7.72 (d, 2H, J=9.0 Hz), 7.53 (t, 2H, J=8.5 Hz), 7.19-7.14 (m, 2H), 2.09 (s, 3H), 1.45 (s, 9H); MS: 270[M-Boc+H]$^+$; HPLC: 98.80% at 210 nm.

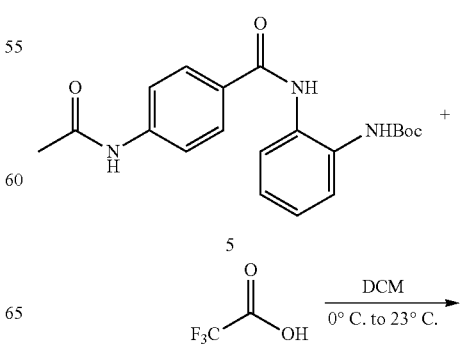

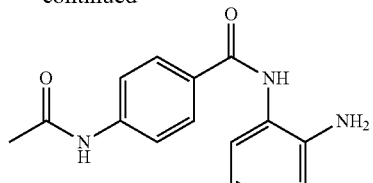

6

To a 0° C. solution of Boc protected benzamide 5 (18 g, 48.7 mmol) in dry DCM (250 mL) was added TFA (100 mL) portionwise. The mixture was allowed to slowly warm to 23° C. After stirring for 2 h, TLC showed that the reaction was complete. The TFA was removed in vacuo and the reaction mixture was diluted with water and the pH was adjusted to ~8 with sat. NaHCO$_3$. The resulting precipitate was filtered, washed with water, ether and dried under vacuum to afford 4-acetamido-N-(2-aminophenyl)benzamide 6 as an off-white solid.

Yield: (11.5 g, 84%).
TLC: good, Rf=0.3 (10% MeOH in DCM)
$^1$H NMR (DMSO-d$_6$, 500 MHz) δ 10.18 (s, 1H), 9.54 (s, 1H), 7.93 (d, 2H, J=9.0 Hz), 7.69 (d, 2H, J=8.0 Hz), 7.15 (d, 1H, J=7.5 Hz), 6.96 (t, 1H, J=8.0 Hz), 6.78 (d, 1H, J=8.0 Hz), 6.59 (t, 1H, J=7.5 Hz), 4.87 (br s, 2H), 2.08 (s, 3H);
MS: 270 [M+1]$^+$; HPLC: 97.71% at 210 nm.

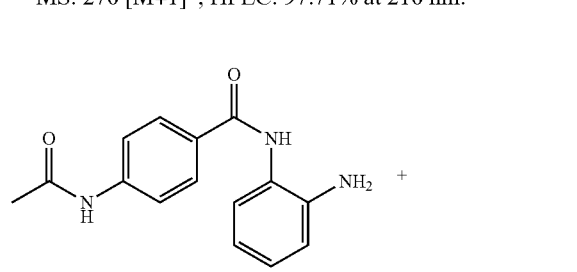

To a 0° C. solution of 4-acetamido-N-(2-aminophenyl) benzamide 6 (520 mg, 1 eq.) in acetone (6 mL) was added 1M HCl in Dioxane (6 mL). The ice bath was removed and the reaction mixture was allowed to slowly warm to 23° C. After stirring for 2 h, the solvents were removed in vacuo and the crude residue was washed with ether and dried under vacuum to provide the mono hydrochloride salt as an off white solid 7.

Figure 36:
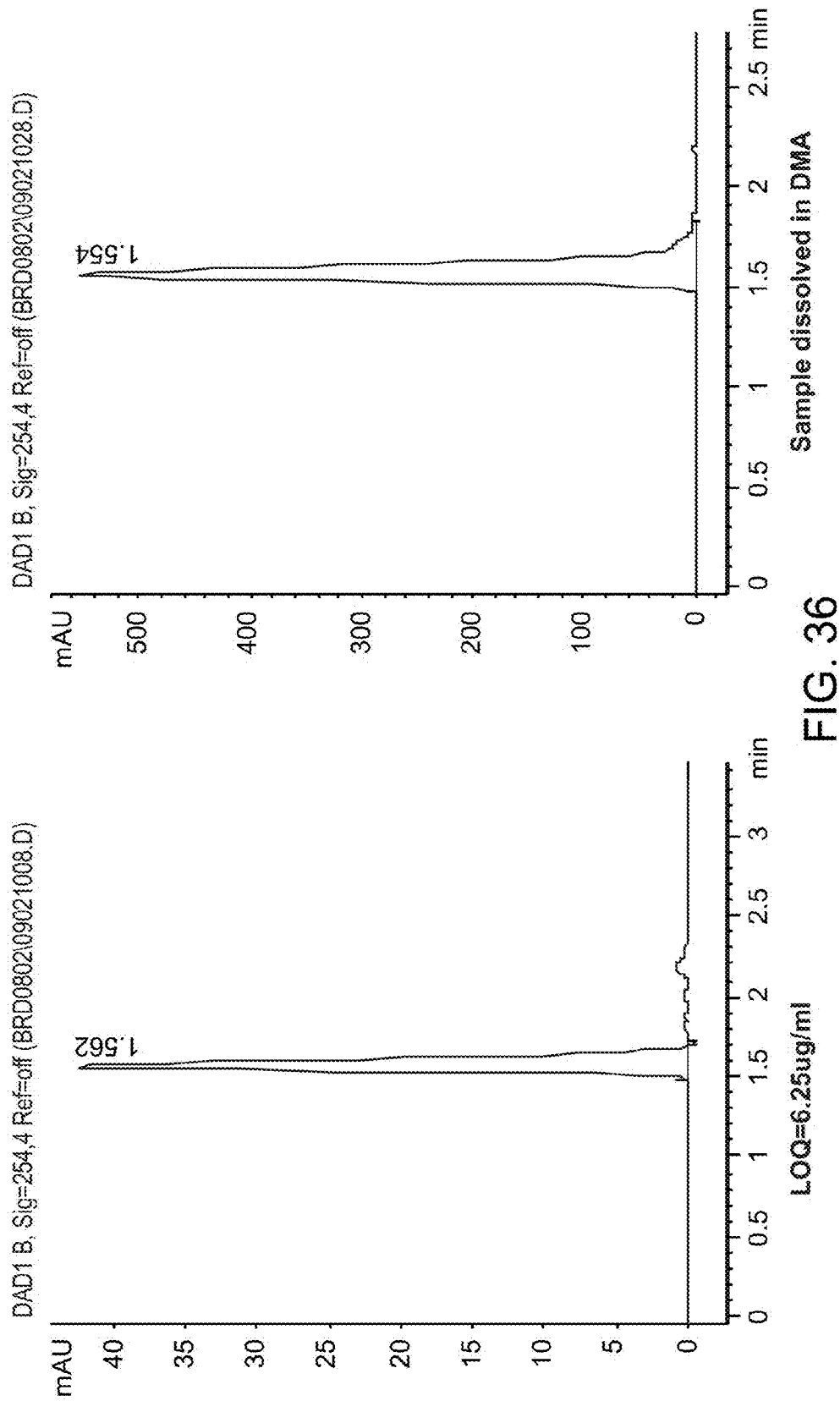
FIG. 36 shows the HPLC method development of CI-994. A. The chromatogram represents the signal at the limit of quantitation (LOQ) of 6.25 ug/mL. B. The chromatogram shows signal at 10× signal intensity. Both chromatograms represent a chemical purity of >95%.
Figure 37:
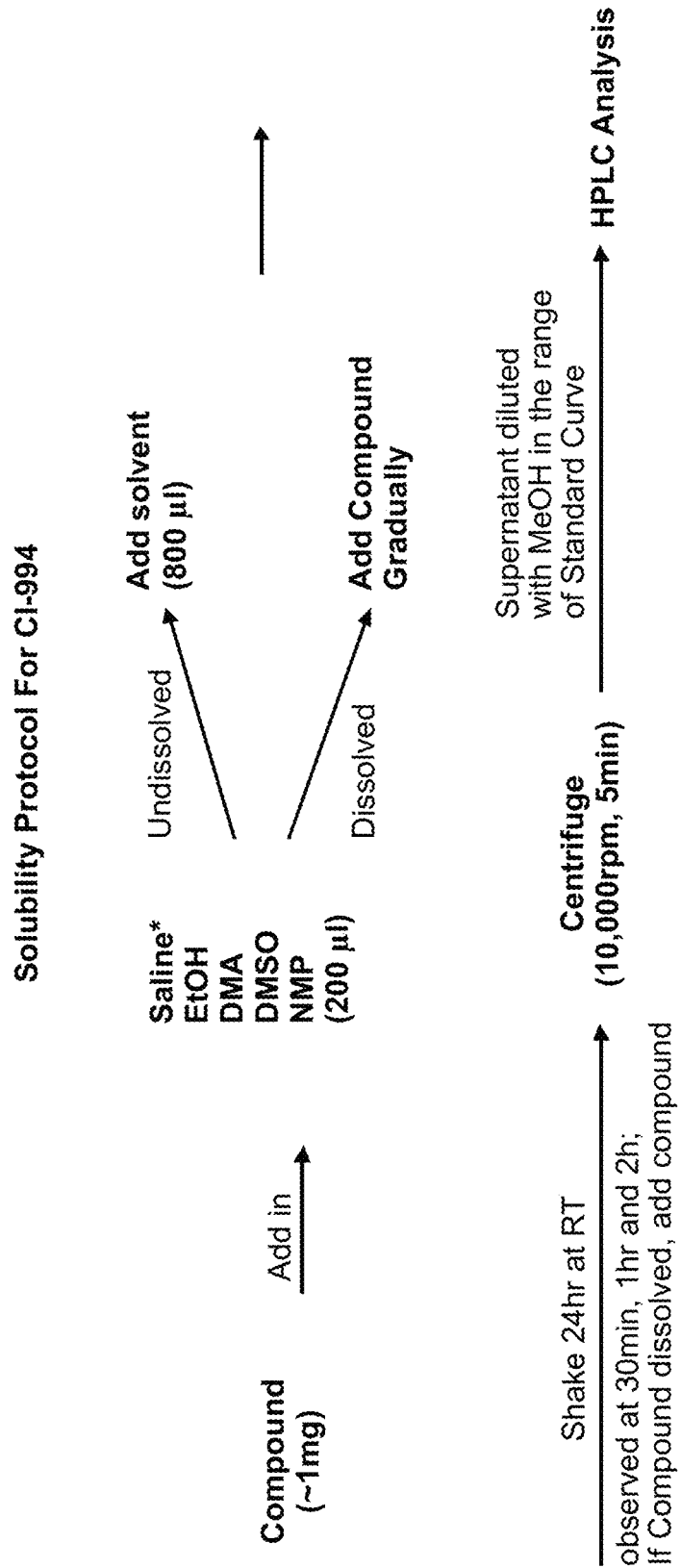
FIG. 37 shows the solubility protocol for CI-994.

Yield: (520 mg, 87%),
TLC: Rf=0.3 (10% MeOH in DCM)
Formulation and Characterization of the Free Base of CI-994:
HPLC Method Development
Column: Luna C18, 5 μm (150*4.6 mm);
Mobile phase (Isocratic): 0.01% TFA: Methanol=5:95
Injection Volume: 10 μl
Wave length: 254 nm
Parameters
LOQ=6.25 μg/ml
Standard Curve: 6.25-200 μg/ml, y=32.279x+28.856, r$^2$=1
Standard curve was established using HPLC conditions outlined above to quantitate the levels of CI-994 in solution (FIG. 36).

The maximal solubility of the CI-994 free base was determined in several solvents using the protocol outlined above. The free base of CI-994 had a maximal solubility of 0.08 mg/mL in saline (0.9% NaCl) for at least 2 h. The solution and chemical stability of the CI-994 free base was monitored via HPLC at the 2 hour time point. DMSO—dimethyl sulfoxide; DMA—dimethylacetamide; NMP—N-methylpyrrolidone; EtOH—ethanol; Saline—0.9% NaCl solution.

| | Conc. in Vehicles (mg/ml) | | | | |
|---|---|---|---|---|---|
| Compound | DMSO | DMA | NMP | EtOH | Saline |
| CI-994 | 266.15 | 246.04 | 243.28 | 2.12 | 0.08 |

Formulations

A series of formulations were examined to improve the solubility of the CI-994 free base in saline using various excipients (FIG. 38). All formulations targeted a stable (chemical and solution) 5 mg/ml solution formulation for 2 hours or more using 4 organic solvents and a broad array of pharmaceutically acceptable excipients. This represents a 62× improvement over the 2 hour solubility of the CI-994 free base in saline alone.

Protocol:
1) Weigh free base and dissolve in organic solvent (DMSO, DMA, NMP, EtOH)
2) Add excipient, mix (vortex, sonicate and/or heat as needed) and visually monitor solubility and homogeneity
3) Add saline, mix (vortex, sonicate and/or heat as needed) and visually monitor solubility and homogeneity
4) Combinations which provided a visually stable for at least 2 hours were further analyzed via HPLC to quantitate solution concentration.

| Concentration Confirmation via HPLC for formulations of CI-994 | | | |
|---|---|---|---|
| | Concentration in samples (mg/mL) | | |
| Formulations (excipient ratios) | 0 hr | 2 hr | 4 hr |
| 10% DMSO + 45% PEG400 + 45% saline* | 5.88 | 5.42 | 5.76 |
| 10% NMP + 45% PEG400+ 45% saline | 5.53 | 5.89 | 5.29 |
| 10% EtOH + 45% PEG400 + 45% saline* | 5.45 | 4.92 | 4.39 |
| 10% DMA + 30% Cremophor + 60% saline | 5.41 | 5.36 | 4.56 |
| 10% DMA + 45% PEG400 + 45% saline | 4.66 | 4.56 | 4.56 |
| 10% DMSO + 30% Cremophor + 60% saline | 5.43 | 5.04 | 5.02 |
| 10% NMP + 30% PEG400 + 60% saline | 5.16 | 5.00 | 4.72 |
| 10% DMA + 30% PEG400 + 60% saline | 4.39 | 4.38 | 4.15 |
| 5% DMA + 45% PEG400 + 50% saline | 4.91 | 4.67 | 4.18 |
| 5% NMP + 45% PEG400 + 50% saline | 4.44 | 4.48 | 4.06 |
| 5% DMSO + 30% Cremophor + 65% saline | 4.72 | 4.38 | 4.04 |
| 5% EtOH + 45% PEG400 + 50% saline | 4.74 | 4.54 | 4.07 |

*formulated at target concentration of 6 mg/mL

Using our standard formulation and analysis protocol we confirmed the concentration of the successful combinations using HPLC analysis. All 12 formulations provided a stable solution (+/−15% target) for a minimum of 2 h. The formulation of 10% DMSO+30% Cremophor+60% saline was used for the studies reported herein.

Formulation and Characterization of the CI-994 HCl Salt:

Linearity of CI-994 HCl Salt (BROAD-SAI-140) by HPLC

Standard Stock Solution Preparation:

1. 1.166 mg of CI-994 HCl salt (BROAD-SAI-140) was dissolved in 1 ml of 1:1 combination of 0.025% Aqueous Trifluroacetic acid and Acetonitrile.

Observation: Compound dissolves completely and clear colorless solution was observed (FIG. 39, Image 1). Standard stock solution was prepared for the development of a robust HPLC method for the determination of CI-994 HCl salt in solution based on area count.

Linearity

Linearity Solution Preparation:

| Level | Target ppm | Stock solution taken | Final dilution volume with diluent* | Actual ppm | Response |
|---|---|---|---|---|---|
| 1 | 200 | 0.4 ml of 500 ppm | 1 ml | 233.20 | 2443990 |
| 2 | 100 | 0.5 ml of 200 ppm | 1 ml | 116.60 | 1215128 |
| 3 | 50 | 0.5 ml of 100 ppm | 1 ml | 58.30 | 596573 |
| 4 | 20 | 0.4 ml of 50 ppm | 1 ml | 23.32 | 238336 |
| 5 | 10 | 0.5 ml of 20 ppm | 1 ml | 11.66 | 121497 |
| 6 | 1 | 0.1 ml of 10 ppm | 1 ml | 1.17 | 11826 |

*Diluent is Acetonitrile: 0.025% Aqueous TFA in 1:1 combination

Solubility Study of CI-994 HCl Salt (BROAD-SAI-140), in Saline (0.9% NaCl) at a Target Concentration of 5 mg/ml Procedure:

1. Weighed 2.501 mg of CI-994 HCl salt in eppendorf tube of capacity 1.5 ml.

2. Added 500 μl of 0.9% saline solution by using micropipette.

3. Shaken the tube manually.

Observation: Solution becomes hazy.

4. Sonicated the above solution of step 3 for 5 minutes.

Observation: Solution becomes white colored cloudy solution when 0.9% saline solution was added. Precipitate was found to be uniformly distributed (FIG. 39, Image 2).

5. Centrifuged the above solution for 15 minutes

Observation: compound settled at the bottom of the tube and supernatant solution was found to be clear (FIG. 39, Image 3).

6. Supernatant clear solution of step 5 was used for analysis.

Solubility Results of BROAD-SAI-140

| Sr. No. | Target concentration | Sample time | Amount of drug dissolved in mg/ml of saline |
|---|---|---|---|
| 1 | 5 mg/ml | Initial | 2.852 |
| 2 | | 2 hours | 2.841 |

By utilizing the HCl salt form of CI-994 we were able to demonstrate a 35× improvement in the solubility of CI-994 in an aqueous solution. HPLC analysis confirmed the chemical and solution stability of the HCl salt form of CI-994 for a minimum of 2 hours. This formulation is suitable for use in the delivery of CI-994 without the use of other excipients.

Example 10

HDAC Inhibitor, CI-994, Promotes Fear Memory Extinction

Materials and Methods:

Two groups of mice were trained in contextual fear conditioning for two times before a three-day-extinction trials. In each extinction day, mice were exposed to the training box without any shock for 3 minutes and returned back to their home-cage. One hour after exposure, mice were injected with either CI-994 (25 mg/kg) or vehicle, and returned to home-cage, one hour before the second 3-minutes-exposure. The freezing behavior of each mouse in the training cage were monitored. To test the fear memory recovery, a reminder shock was given one hour after the last extinction trial. The freezing time were quantified 24 hours after the reminder shock.

Results:

The freezing levels of the mice during the first 3-min-exposure in each day were measured and plotted. Extinction of the fear memory was much faster in the CI-994 treated group than the vehicle treated group. On the third day, CI-994 group showed significantly less freezing time than the control group. N=8 for each group. *, p<0.05 (FIG. 41, panel B). The freezing levels of the mice in the two contextual exposure training, before and after injection, during extinction day 1 were quantified and plotted. CI-994 group showed faster decay of freezing time (FIG. 41, panel C). The freezing levels of the mice in the two contextual exposure training, before and after injection, during extinction day 2 were quantified and plotted. CI-994 group showed faster decay of freezing time (FIG. 41, panel D). 24 hours after the reminder shock, freezing level of each group were measured under the training contextual. No significant difference were observed between CI-994 group and control group, both of which showed high level of freezing (FIG. 41, panel E).

Example 11

Expression of HDAC1 and HDAC2 in the Cortex of p25 Mice

Expression of HDAC1 and HDAC2 was measured in the cortex of p25 mice. Expression of HDAC2 was found to be significantly higher in p25-CK mice than in control mice (FIG. 42A). In contrast, HDAC 1 expression was not altered (FIG. 42B).

Expression of HDAC2 was significantly higher in CK-p25 mice than in control mice. In contrast, acetylation of histone4 lysine 12 (AcH4K12) intensity was decreased in CK-p25 mice. Chronic CI-994 treatment (1 mg/kg, i.p.), for 10 days (beginning from 6 weeks after induction of p25) increased acetyaltion on H4K12. p25-GFP was induced for 6 weeks in CK-p25 mice. CK-p25 mice also showed increased expression of hdac2 and reduced AcH4K12 in cortical neurons. Chronic CI-994 treatment (1 mg/kg, i.p.), for 10 days (beginning from 6 weeks after induction of p25) increased acetyaltion on H4K12. p25-GFP is induced for 6 weeks in CK-p25 mice.

Example 12

CI-994 Treatment Increased Synaptophysin (SVP) Expression in CK-p25 Mice p25-GFP was induced for 6 weeks in CK-p25 mice. Afterwards, mice received chronic CI-994 treatment (1 mg/kg, i.p.)

for 10 days. Hippocampi were isolated and subjected to protein quantification by western blot analysis. 6-week expression of p25 resulted in a marked reduction of SVP. Chronic CI-994 treatment rescued SVP expression in the CK-p25 mice. Moreover, GFAP, a marker for reactive astrocytes, was elevated in CK-p25 mice and reduced in the group treated with CI-994 (FIG. 43). These results showed that CI-994 treatment induced active synaptogenesis in the CK-p25 mice after neurodegeneration, effects which are consistent with improved cognitive function and memory.

CI-994 treatment also upregulates MAP2 positive dendrites in CK-p25 mice. p25-GFP was induced for 6 weeks. Mice subsequently received chronic CI-994 treatment (1 mg/kg, i.p.) for 10 days. Mice were fixed and stained with MAP-2 antibody, which is a marker for dendrites. In 6-week induced CK-p25 brain, MAP2 staining intensity was markedly reduced. Chronic CI-994 treatment increased MAP2 staining intensity in the CK-P25 mice. These results demonstrate that CI-994 induced active dendritic growth after neurodegeneration.

Example 13

Increased Expression of HDAC2 and Reduced AcH4K12 in Cortical Neurons of 5×FAD Mice (The Transgenic Mouse Carries 5 Familiar Alzheimer's Diseases Mutant Genes)

Figure 44B:
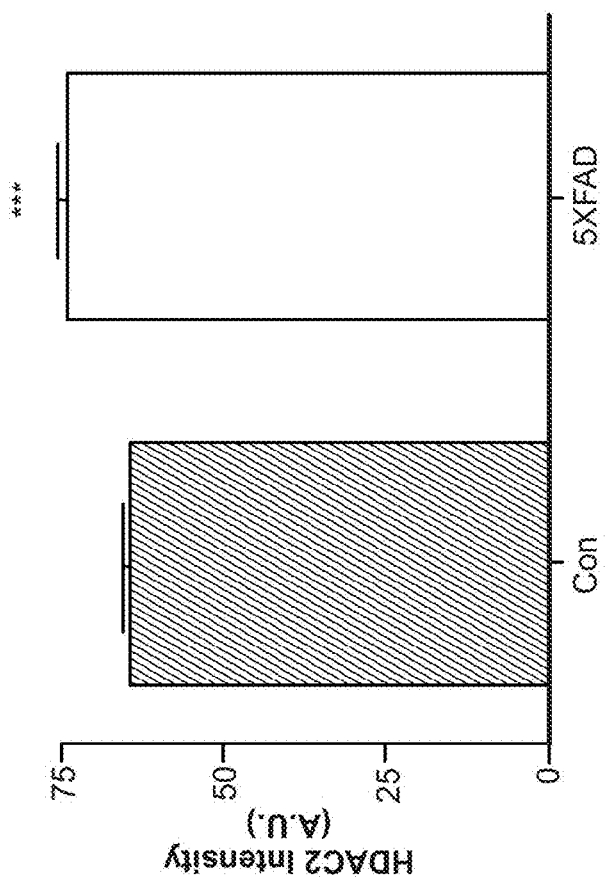
FIGS. 44A and 44B shows increased expression of HDAC2 and reduced AcH4K12 in cortical neurons of 5×FAD mice (5 familiar Alzheimer's Diseases mutant genes). A. Quantification of AcH4K12 immunoreactivity. B. Quantification of HDAC2 immunoreactivity.
Figure 44A:
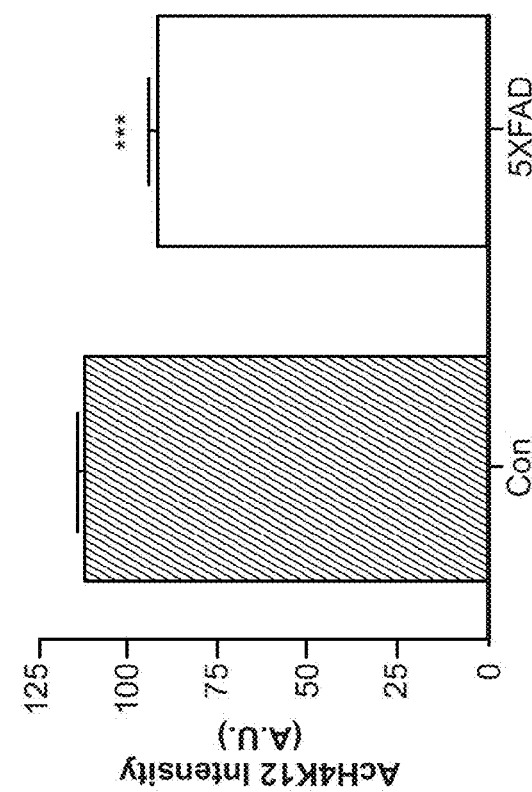
Figure 44E:
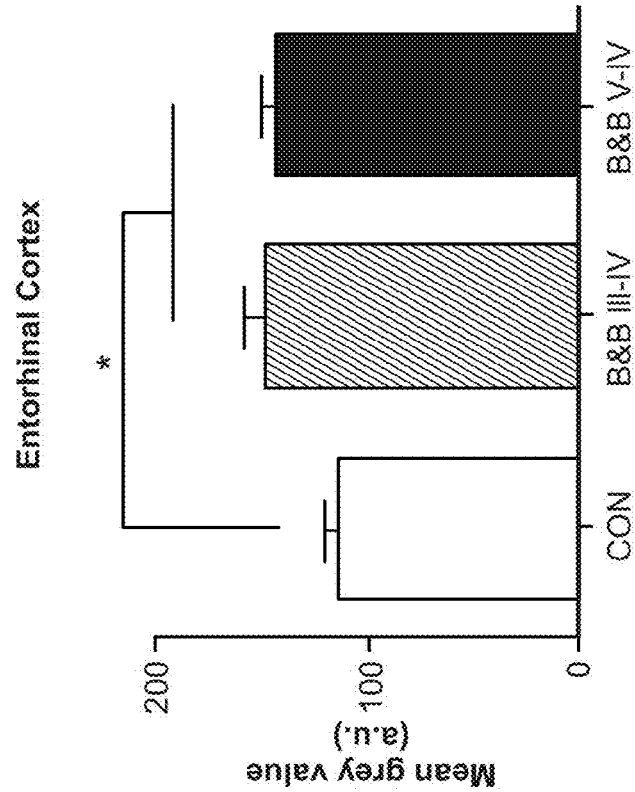
Figure 44D:
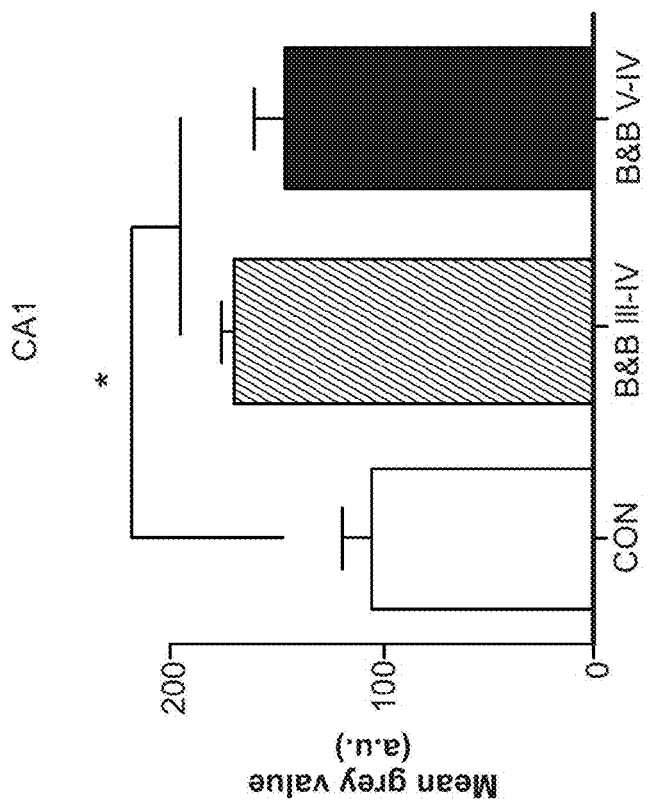

5×FAD mice and their control littermates were 10 month old. Expression of HDAC2 was found to be significantly higher in the 5×FAD mice than in control mice (FIG. 44B). In contrast, AcH4K12 intensity was significantly decreased in the 5×FAD mice (FIG. 44A).

Expression of HDAC2 in hippocampal CA1 neurons in the 5×FAD mice was also increased compared to their control littermates. In contrast, HDAC1 intensity was similar in 5×FAD mice and in control littermates (10 months old).

The human Alzheimer's brain is characterized by increased levels of the histone deacetylase HDAC2. Representative immunohistochemistry images of HDAC2 in paraffin-embedded sections of hippocampal area CA 1 and entorhinal cortex of control brains, cases with mild Alzheimer's Disease (Braak and Braak (B&B) stage III-IV) and cases with severe Alzheimer's Disease (B&B stage V-VI) are shown in FIG. 44C. Scale bar=0.7 mm for upper panels, 0.35 mm for lower panels. Case details are shown in FIG. 44F.

Example 14

CI-994 and Memory Formation

Figure 45A:
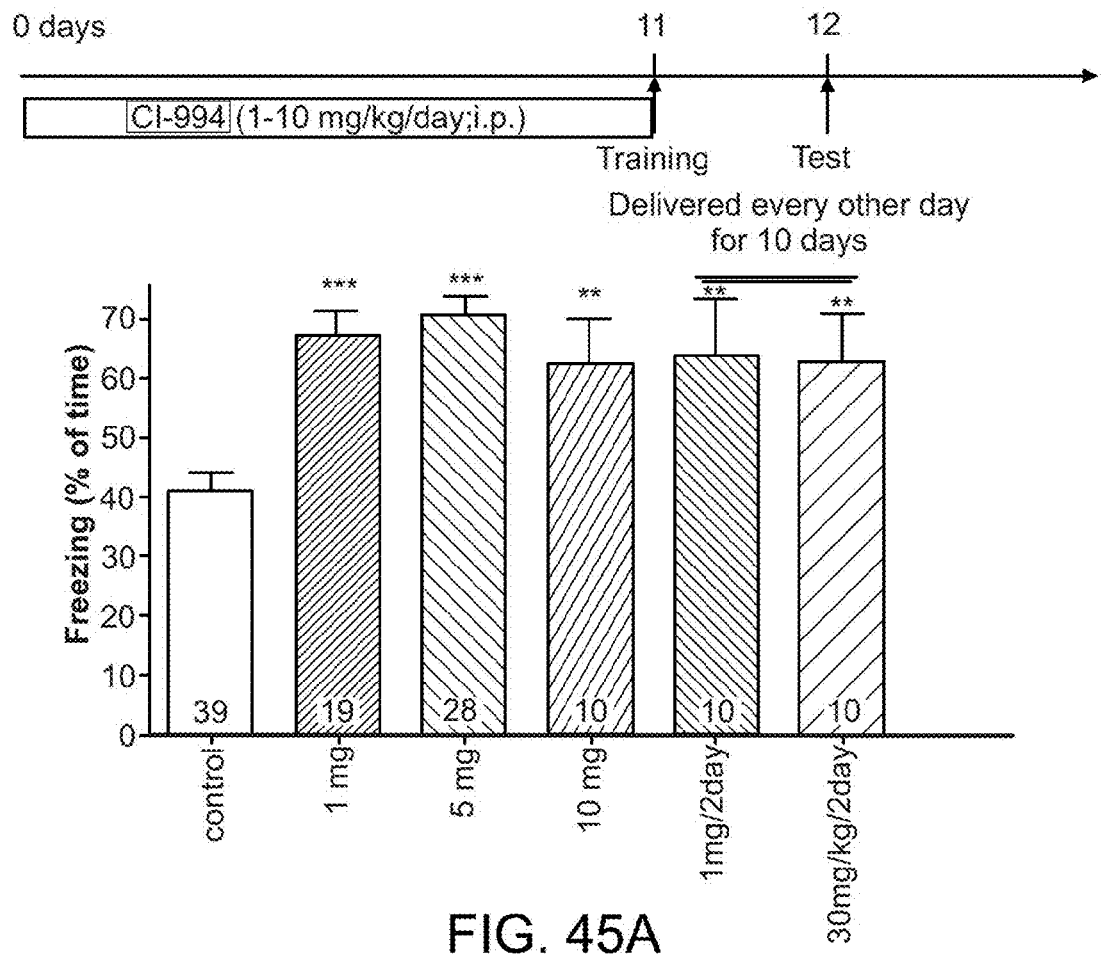
FIG. 45A shows that CI-994 with everyday and every other day dosing schedules at a variety of doses enhances memory formation in wildtye (WT) mice.

CI-994 enhances memory formation in wildtype (WT) mice. Wild type C57/BL6 mice were treated with CI-994 for 10 days. Different doses were administered as indicated in FIG. 45A. The total number of mice in each group is indicated in the bottom of each column of FIG. 45A. Mice were subsequently trained with contextual fear conditioning paradigm and tested 24 hours after training. The last two columns of FIG. 45A show two groups of mice injected with CI-994 every other day for 10 days (a total of 5 doses). Doses of CI-994 as low as 1 mg/kg were able to enhance memory formation in the mice. In contrast, Aricept (Cholinesterase inhibitor) has no effect on memory formation in WT mice. Wild type C57/BL6 mice were treated with CI-994 (1 mg/kg, i.p.) or Aricept (1 mg/kg), for 10 days. n=20 for each group. After 10 day's dosing, mice were trained with contextual fear conditioning paradigm and tested 24 hours after training.

Figure 45B:
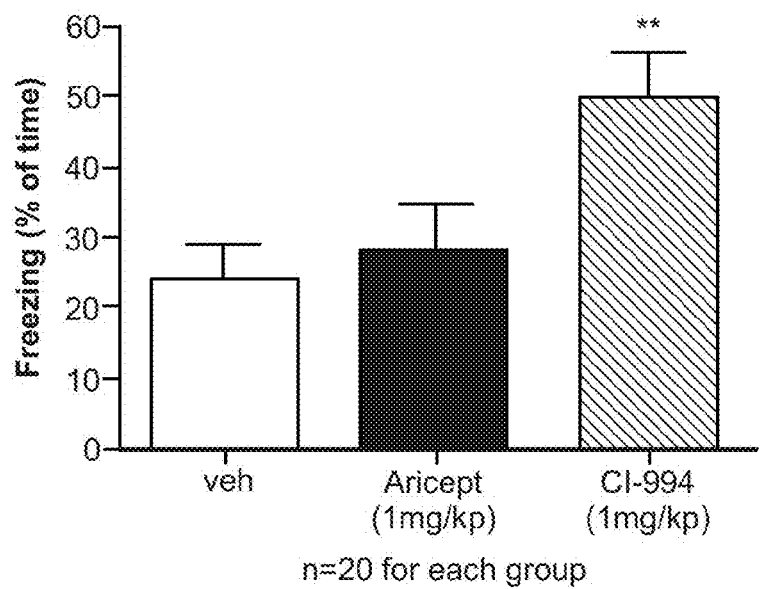
FIG. 45B shows that CI-994, but not Aricept (Cholinesterase inhibitor) increases memory formation in WT mice.

CI-994 treatment significantly increased memory formation in WT mice, while Aricept treatment did not show any effects in memory formation (FIG. 45B).

Example 15

CI-994 and Memory Impairment

Figure 46A:
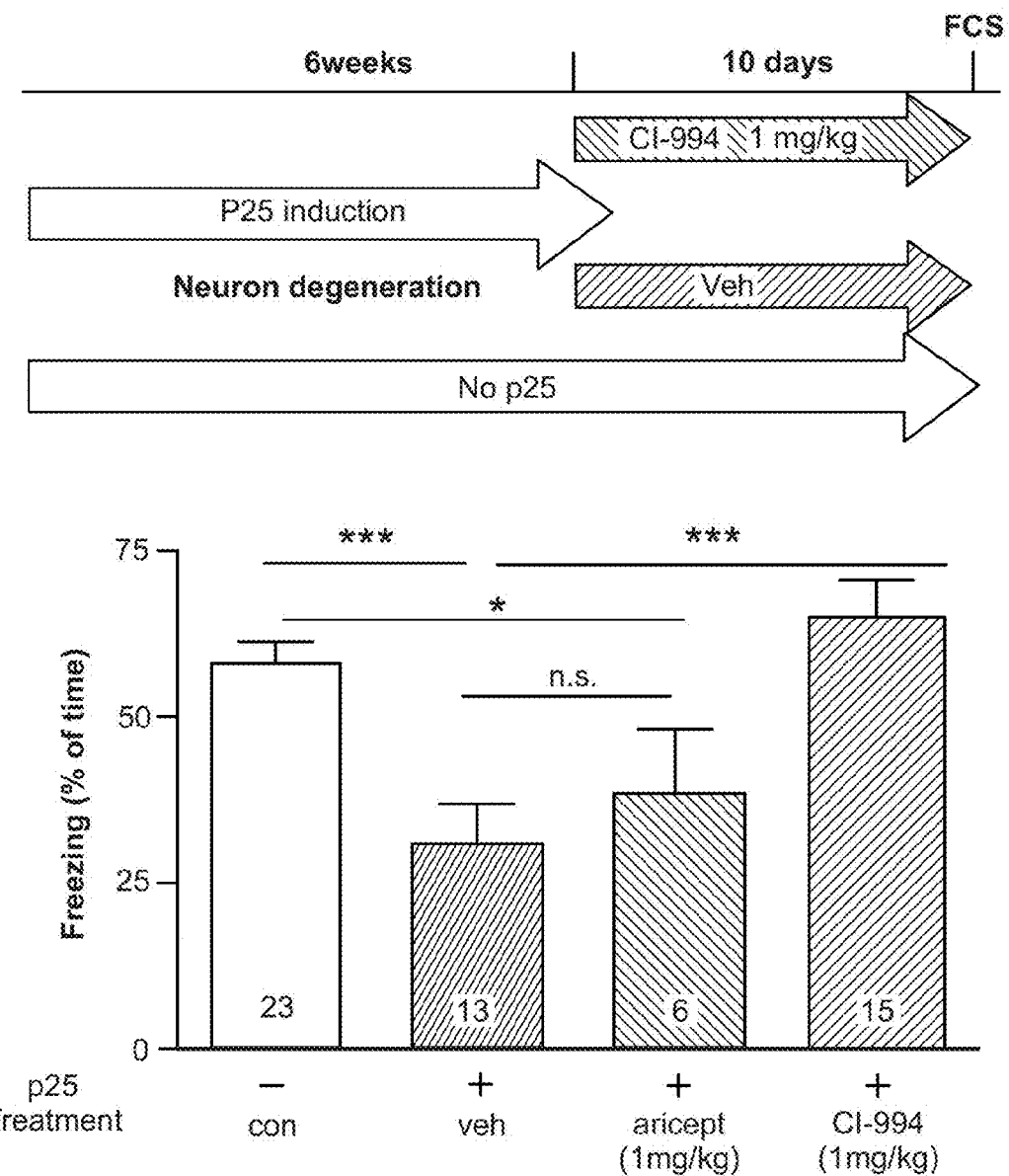
FIG. 46A demonstrates that chronic CI-994, but not Aricept treatment ameliorated memory impairment in CK-p25 mice.

Chronic CI-994, but not Aricept treatment ameliorated memory impairment in CK-p25 mice. p25-GFP was induced for 6 weeks in CK-p25 mice. Mice subsequently received chronic CI-994 (1 mg/kg, i.p.), Aricept (1 mg/kg) or vehicle for 10 days. All groups of mice were trained in contextual fear conditioning paradigm and tested 24 hours later. Chronic CI-994, but not Aricept treatment rescued memory impairment in CK-p25 mice (FIG. 46A). Freezing represents the percentage of freezing time during 3 minutes exposure to the training context with a deduction of the basal freezing levels before shocking.

Figure 46B:
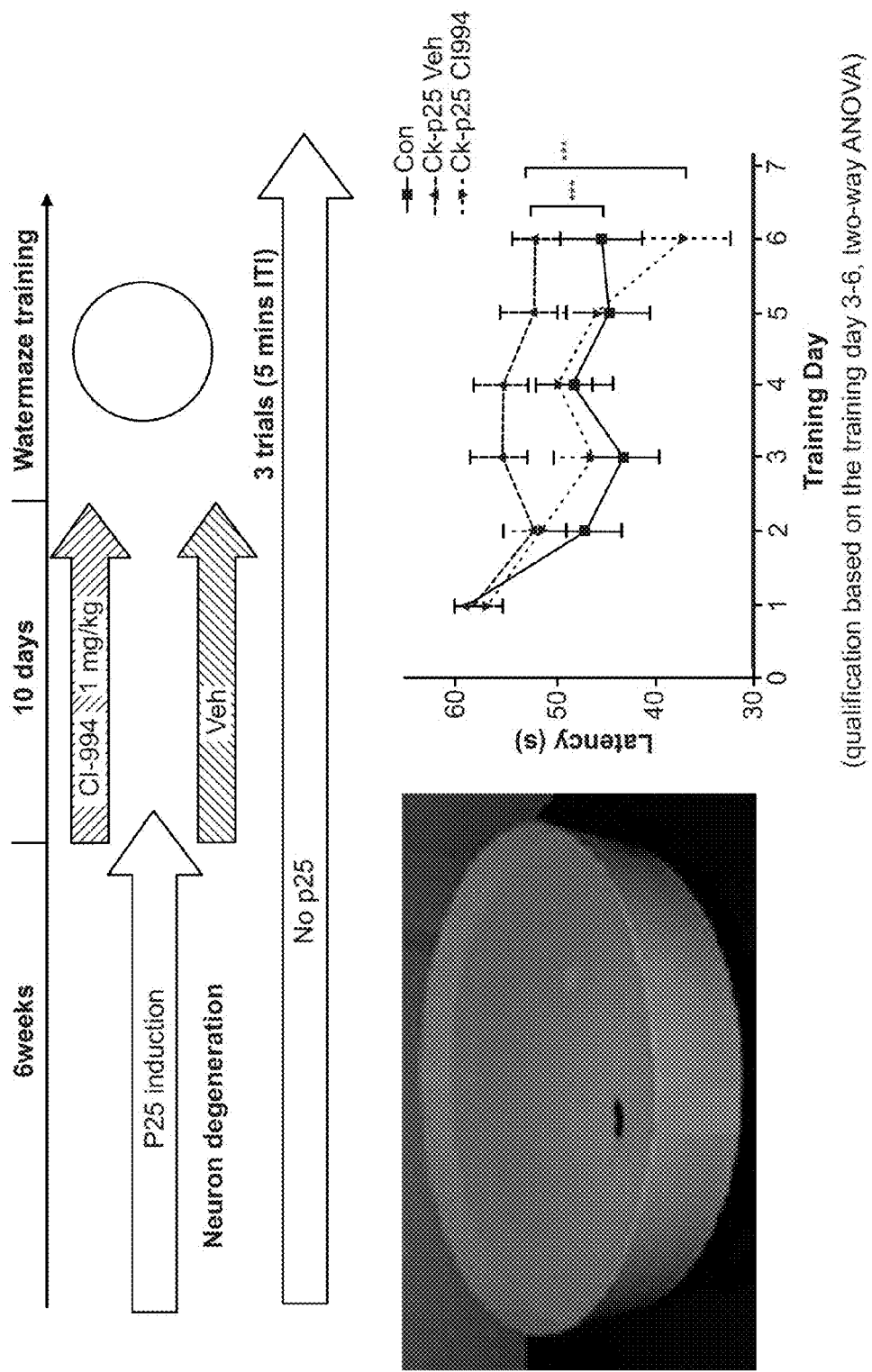
FIG. 46B shows that chronic CI-994 treatment ameliorated spatial memory deficits in CK-p25 mice.
Figure 46C:
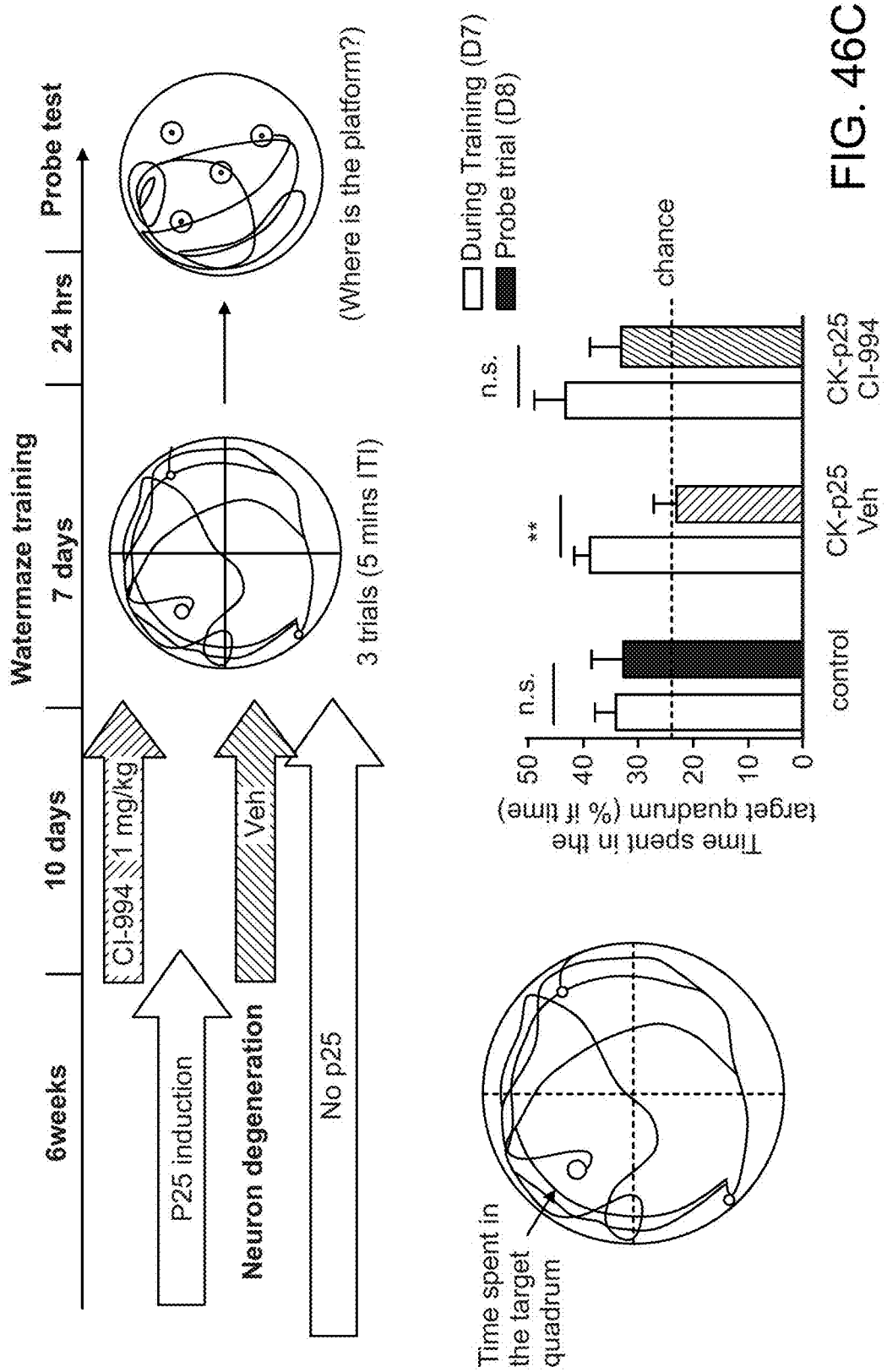
FIG. 46C shows that CI-994 treatment ameliorated memory retrieval deficits in CK-p25 mice.

Chronic CI-994 treatment also ameliorated spatial memory deficits in CK-p25 mice. p25-GFP was induced for 6 weeks in CK-p25 mice. Mice subsequently received chronic CI-994 (1 mg/kg, i.p.) or vehicle for 10 days (FIG. 46B). All 3 groups of mice were trained with the standard Morris watermaze paradigm for 6 days. Mice were placed in the swimming pool for 60 seconds to search for the hidden platform in each trial. A total of 3 trials were performed in each day with 5 min inter-trial-intervals. A picture of the watermaze setup is shown in FIG. 46B. The average time each group of mice spent to find the platform is plotted (escape latency). CK-p25 mice treated with CI-994 showed similar learning curve as control mice, while CK-p25 mice treated with vehicle were considerably delayed in locating the hidden platform. These effects were seen even 7 days after the last dose, which was quite surprising.

CI-994 treatment ameliorated memory retrieval deficits in CK-p25 mice. p25-GFP was induced for 6 weeks in CK-p25 mice. Mice subsequently received chronic CI-994 (1 mg/kg, i.p.), or vehicle for 10 days. The two groups of mice were trained in the Morris watermaze paradigm for 7 days as described above. On day 8, platform was removed and mice were tested for memory retrieval. The average time each group of mice spent in the target quadrant is plotted. On day 8, CK-p25 mice treated with CI-994 showed comparable time spent in the target quadrant as training day 7, suggesting competent memory retrieval. In contrast, on day 8, CK-p25 mice treated with vehicle spent significantly less time in the target quadrant than during the training day (day 7). Thus, CK-p25 mice were impaired in spatial memory retrieval but CI-994 treatment rescued the memory retrieval deficits.

Example 16

Figure 47A:
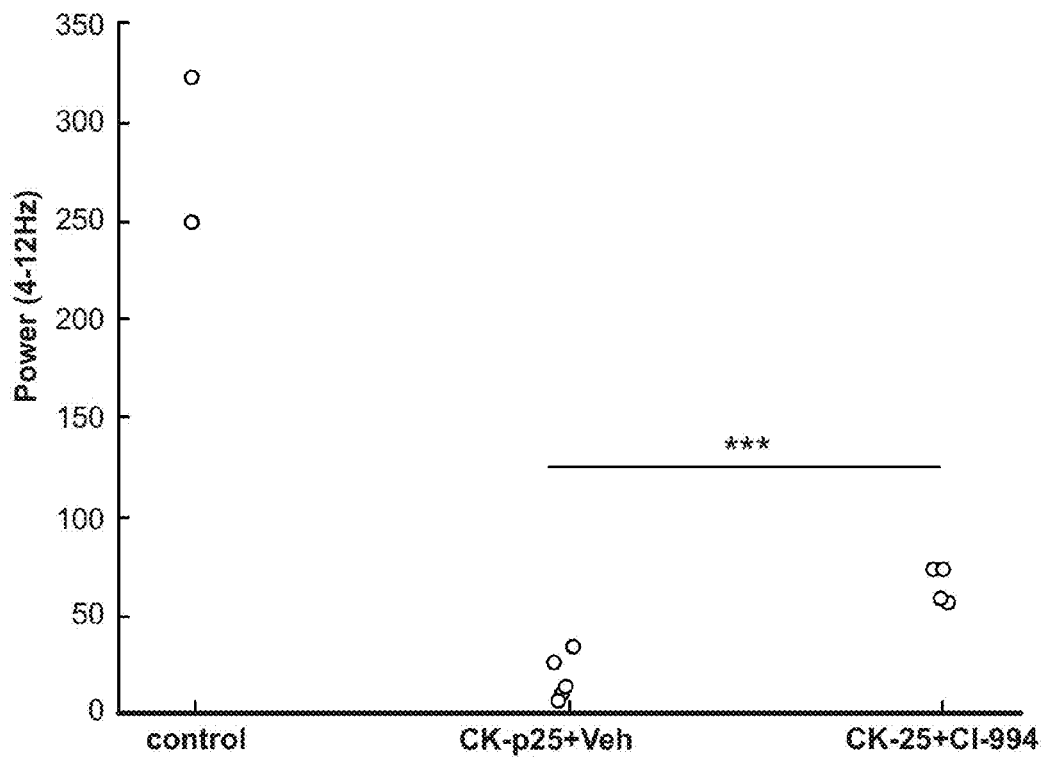
FIG. 47 demonstrates the long-lasting effects of CI-994 in brain oscillation. A. LFP power in the theta band. B. LFP power in the gamma band.
Figure 47B:
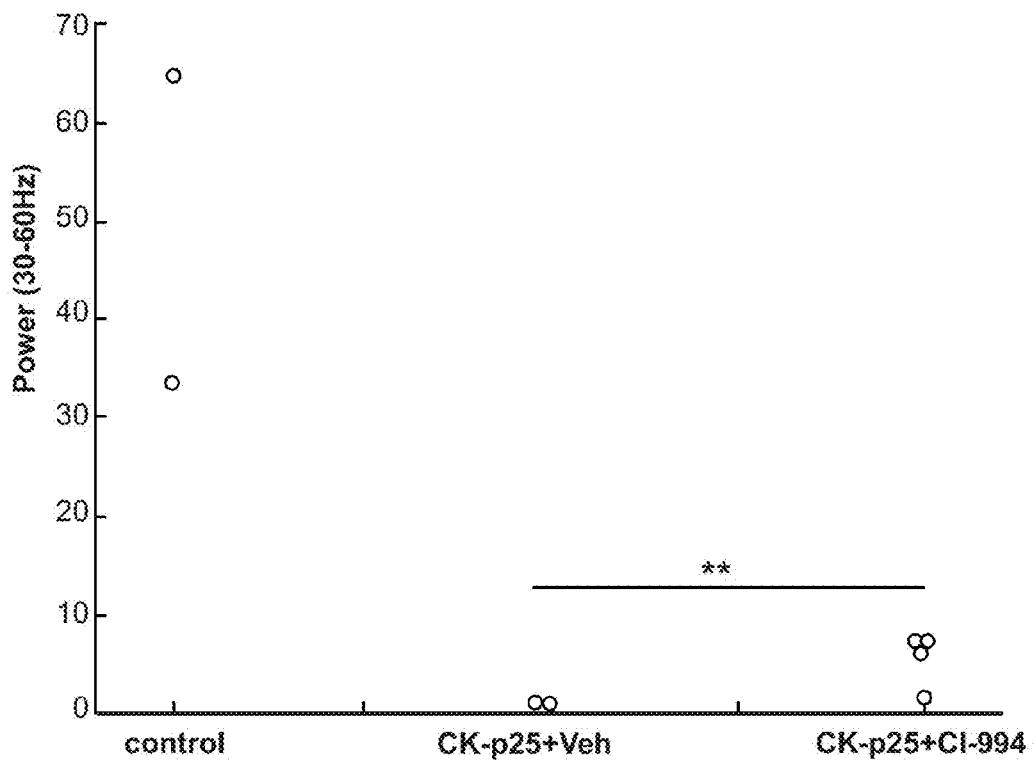

Long-Lasting Effects of CI-994 in Brain Oscillation p25-GFP was induced for 6 weeks in CK-p25 mice. Mice subsequently received chronic CI-994 treatment (1 mg/kg, i.p.), or vehicle for 10 days. 10 days after CI-994 treatment, mice were anaesthetized under 2% isoflurine and synchronized firing was measured using a glass electrode in the hippocampus CA1 area. Local field potential (LFP) was recorded for 5 minutes for each animal. n=5 for CK-p25 mice with vehicle treatment, n=4 for CK-p25 mice with CI-994 treatment. CK-p25 mice showed significant reduction in the oscillation power (over-10 fold reduction), compared to control animals. CI-994 treatment significantly increased the oscillation power in area CA1 of the CK-p25 mice (FIG. 47A-LFP power in the theta band; FIG. 47B-LFP power in the gamma band).

Example 17

CI-994 and Fear Extinction

Figure 48A:
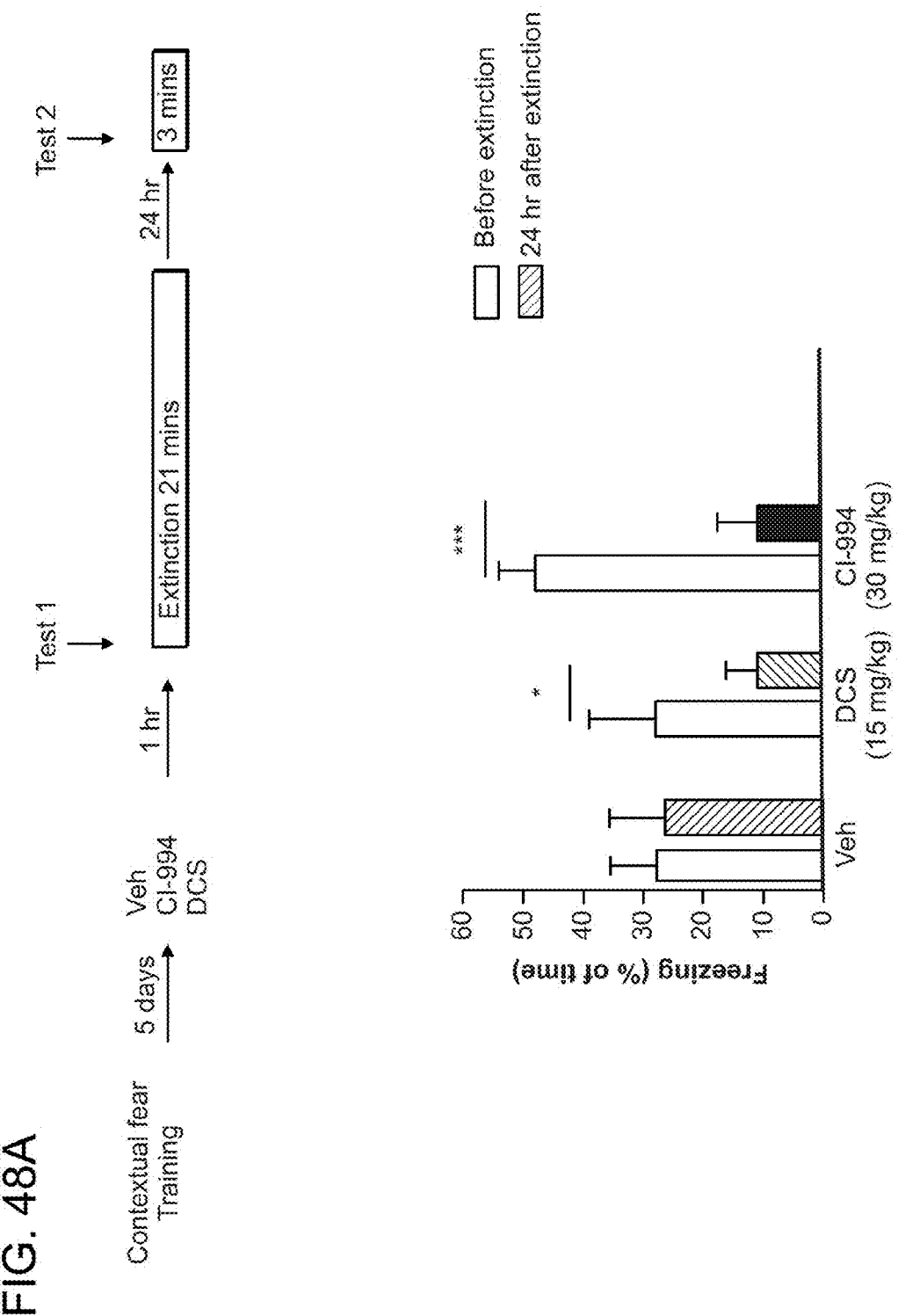
FIG. 48A shows that CI-994 and D-cycloserine (DCS) facilitated fear extinction under normal extinction paradigm, while FIG. 48B demonstrates that CI-994 but not D-cycloserine treatment facilitated fear extinction under the reconsolidation paradigm.

CI-994 and D-cycloserine (DCS) facilitated fear extinction under normal extinction paradigm. Wild type C57/BL6 mice were trained with contextual fear conditioning paradigms. 5 days after training, mice were injected with DCS (15 mg/kg) or CI-994 (30 mg/kg) and subsequently subjected to the extinction trial for 21 minutes in the training context without shock. The freezing time in the first 3 minutes of the extinction trial and the time in the testing trial 24 hours after the extinction training was measured. Both DCS and CI-994 treated groups showed significant reduction in freezing 24 hours after the extinction training (FIG. 48A).

Figure 48B:
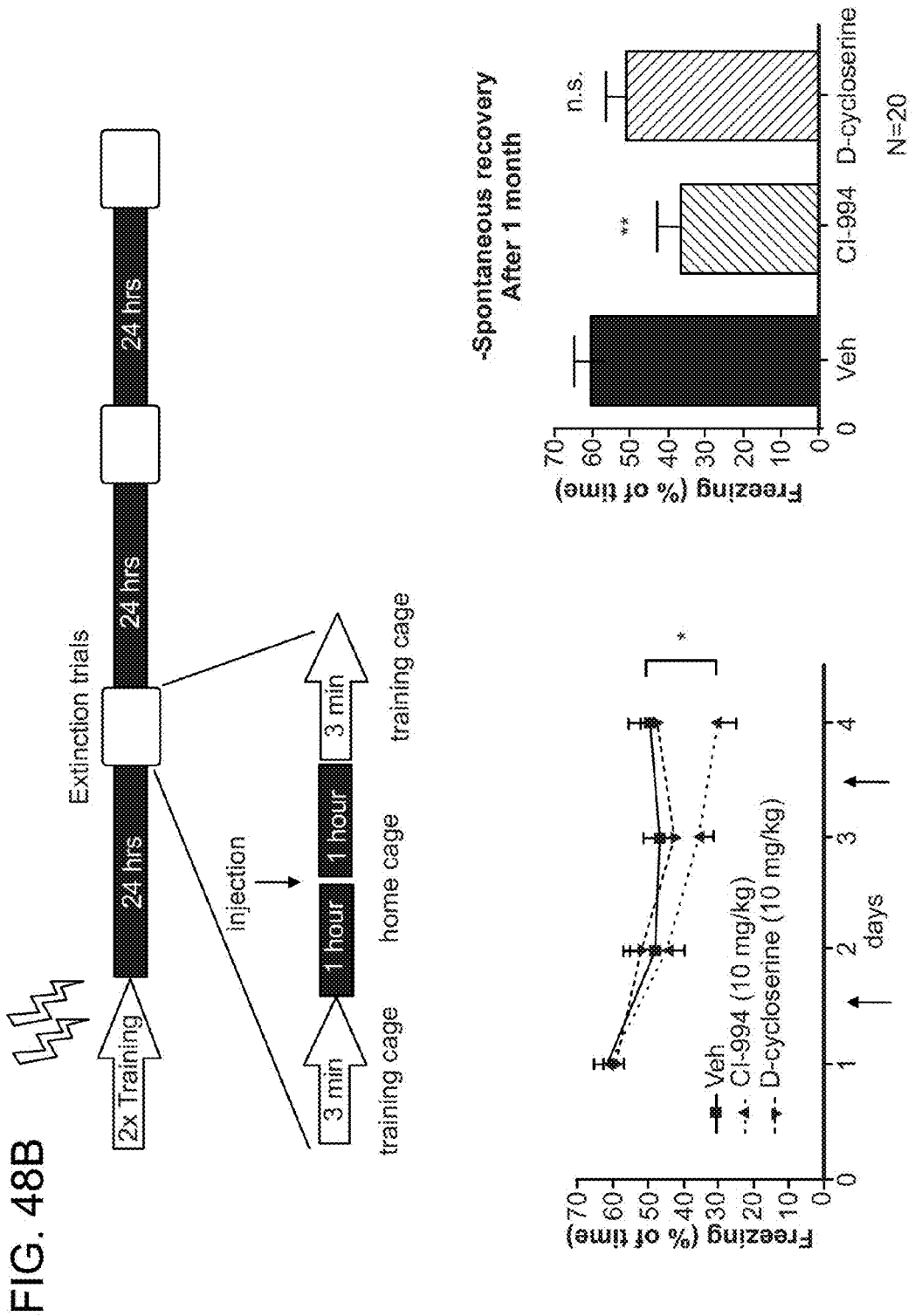
FIG. 48C shows that CI-994 facilitates the extinction of fear memory under specific context.

CI-994 but not D-cycloserine treatment facilitated fear extinction under the reconsolidation paradigm. Mice were trained in contextual fear conditioning paradigm with two shocks. The mice subsequently received the reconsolidation training during the following 4 days. In each day, mice were exposed to the context for 3 minutes to reactivate the fear memory previously acquired followed by an injection of CI-994, DCS or vehicle, as indicated. One hour after injection, mice were placed back to the same context for 3 minutes. The freezing time of the first trial in each day was measured and plotted. CI-994, but not DCS, significantly facilitated fear extinction under this paradigm (two-way ANOVA of training day 2-4, n=20 for each group; FIG. 48B)

Spontaneous recovery of the fear memory were tested one month after the initial fear memory training. The CI-994 treated group showed significantly lower freezing level than the vehicle group, while the DCS treated group showed no significant difference comparing to the vehicle group. (students t-Test).

Figure 48C:
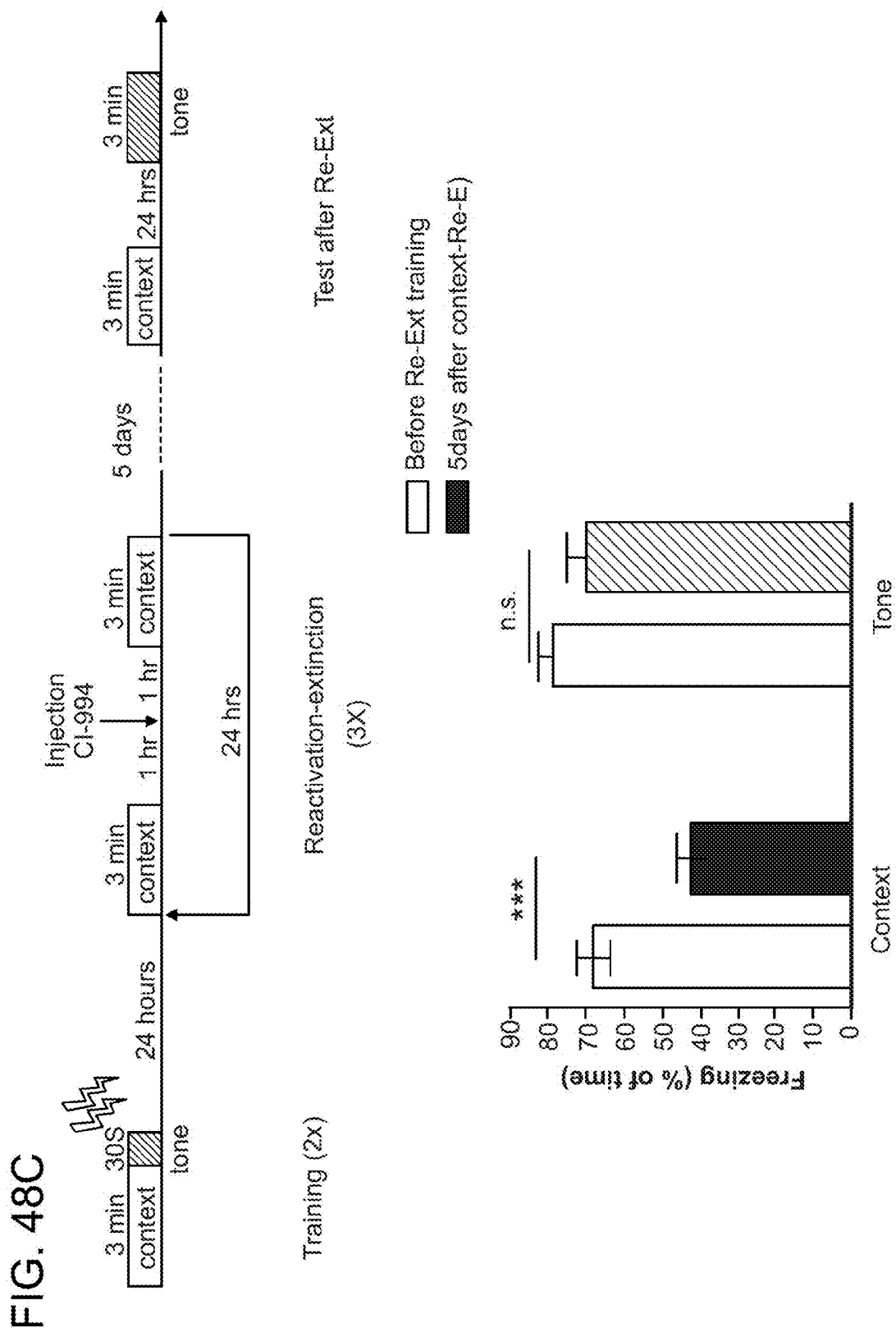

CI-994 also facilitates the extinction of fear memory under specific context. Mice were placed in a novel training box for 3 minutes and received tone for 30 seconds, followed by electrical shocks. A second training was given 24 hours later. Twenty-four hours after the second fear conditioning training, mice were exposed to the training chamber (context only) to retrieve the context dependant memory. CI-994 (30 mg/kg) was injected one hour after retrieval. One hour after injection, mice were placed back in the chamber for 3 mm for the extinction training. The reactivation-extinction trials were performed once in each day for 3 days and freezing level was measured 5 days after the last training. (n=10 for each group). CI-994 treatment enhanced extinction of fear memory under specific context (FIG. 48C).

CI-994 can also replace the first exposure of the memory reconsolidation paradigm to extinguish the fear memory. As shown in FIG. 52, the spontaneous recovery of fear memory was not evident even by 30 days after fear extinction training, when CI-994 was administered prior to a single fear associated context. WT C57/BL6 mice received CI-994 (SC027) (i.p. 30 mg/kg) or Vehicle (Veh) treatment, one hour before the fear extinction trial. The mice were exposed to the fear-associated context for 21 minutes without pairing with shock. Freezing behavior was measured in the first 3 minutes and last 3 minutes during the extinction training, 24 hrs after extinction and 30 days after extinction. (n=20 for each group). Thus, only one dose of CI-994 paired with a longer fear extinction exposure resulted in effective reduction in freezing, behavior, even one month later.

Example 18

CI-994 Efficiently and Persistently Extinguishes Traumatic Long-Term Memories

Figure 49A:
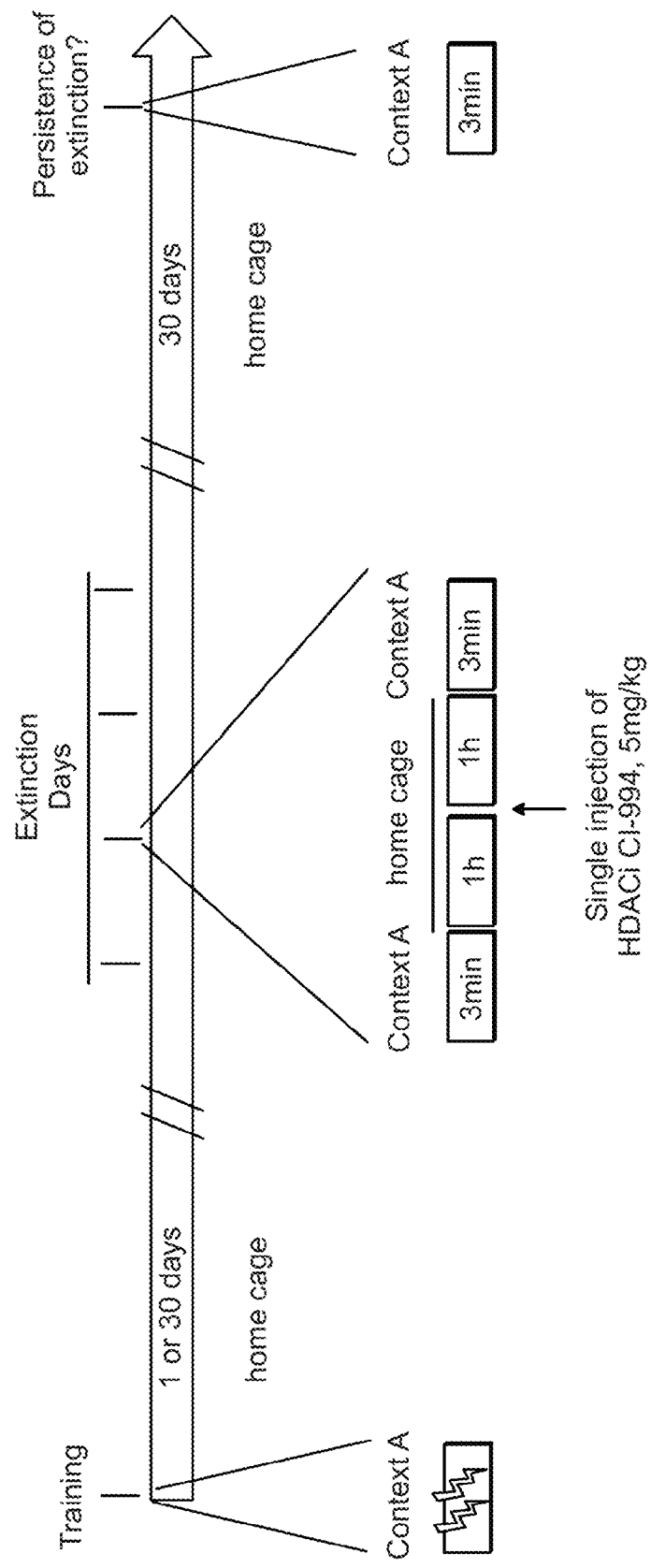
Figure 49D:
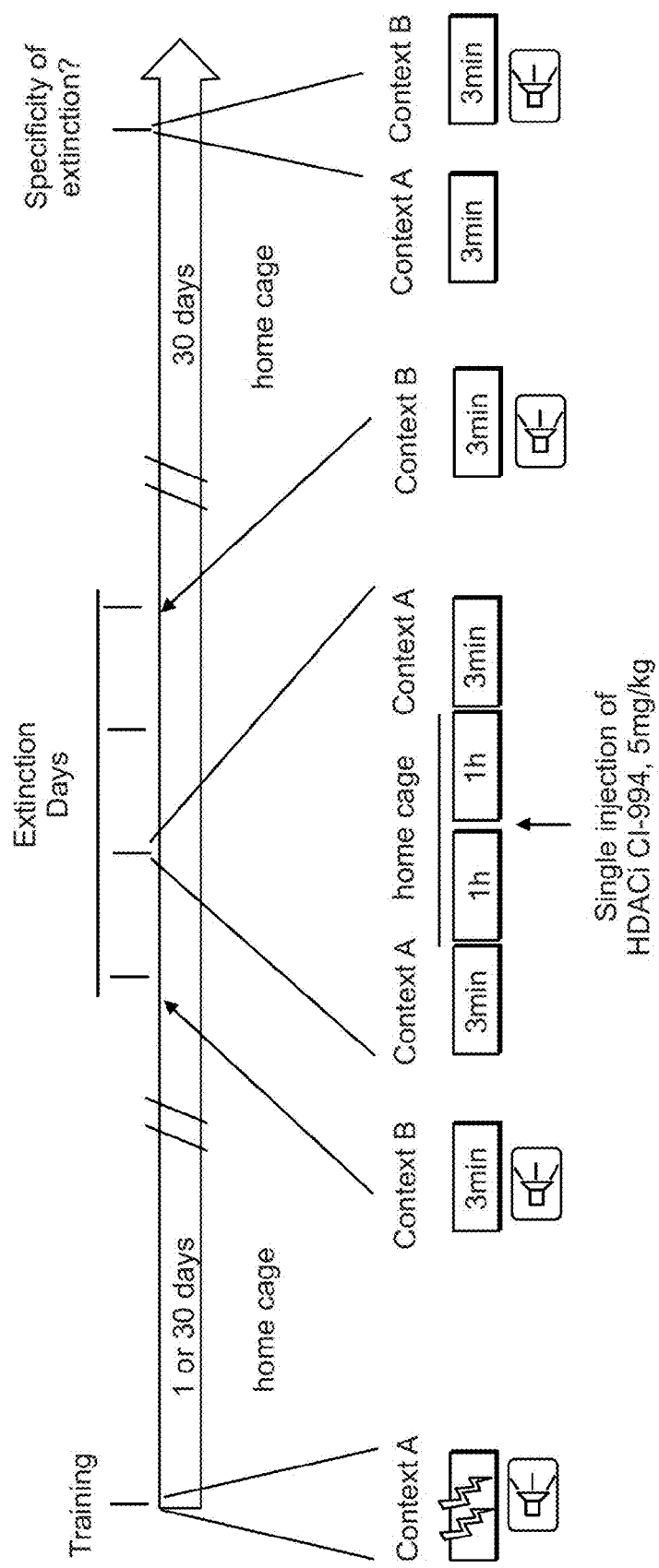
Figure 49F:
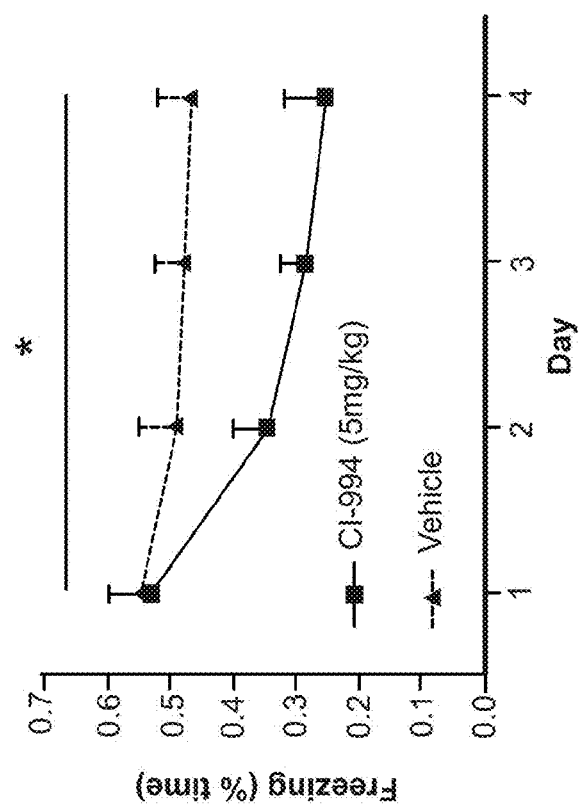
Figure 49E:
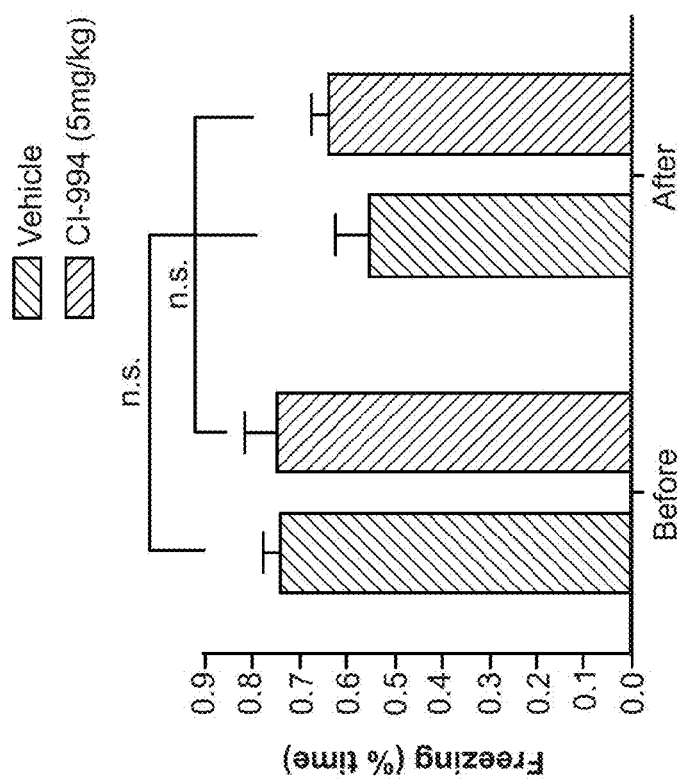
Figure 49H:
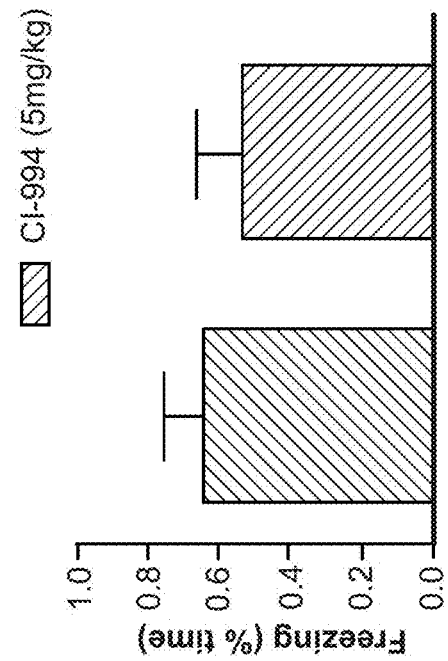
Figure 49G:
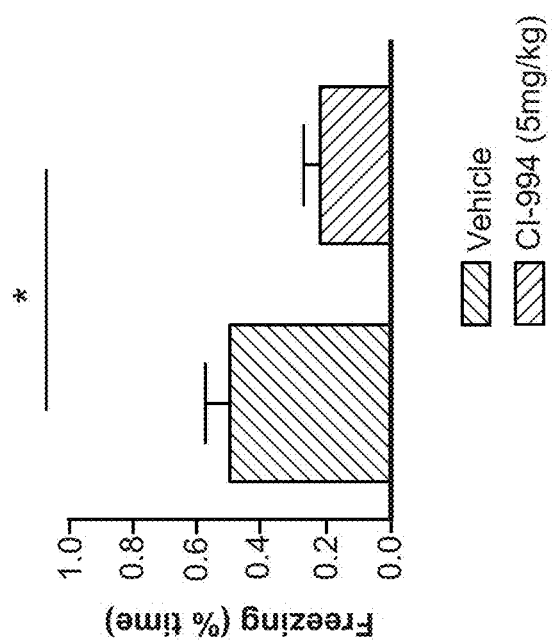

A schematic representation of the experimental design used to probe the efficacy of the HDAC inhibitor CI-994 (5 mg/kg) to extinguish traumatic long-term memories is shown in FIG. 49A. 30 days after training, mice were exposed to two 3-min extinction sessions per day in the same context as they were trained. CI-994 significantly reduced the animals' freezing level, indicating extinction of conditioned fear (p<0.001 for the effect of day; n=10 for vehicle-treated animals, n=11 for CI-994-treated animals; FIG. 49B). When tested again 30 days after the last extinction trial, CI-994-treated animals still show reduced freezing levels compared to vehicle-treated ones, indicating long-term persistence of the extinction (t13=4.402, p<0.001; FIG. 49C). A schematic representation of the experimental design used to probe the specificity of the memory extinction with CI-994 (5 mg/kg) is shown in FIG. 49D. 30 days after fear conditioning to both the context (context A) and the cue (3×0.8 mA shock for 2 sec paired with a tone) mice were first exposed to the cue alone in a different context (context B) than the one in which training occurred (context A), and subsequently to two 3-min extinction sessions per day in the same context as they were trained (context A). After the end of this extinction session, mice were again exposed to context B, and their memory tested. CI-994 did not affect memories formed in a context different from the extinction context (n.s. for the effects of treatment and time; n=10 mice per group; FIG. 49E), but exclusively reduced the animals' freezing level in the context in which the extinction had occurred (p<0.05 for the effect of day; n=10 mice per group; FIG. 49F). When tested again 30 days after the last extinction trials, CI-994-treated animals still show reduced freezing levels compared to vehicle-treated ones in the extinguished context (t8=2.955, p<0.05; FIG. 49G), but not in the different context (n.s. for the effect of treatment, n=5 per group; FIG. 49H), indicating context-specific long-term persistence of extinguished memories.

Example 19

Figure 50:
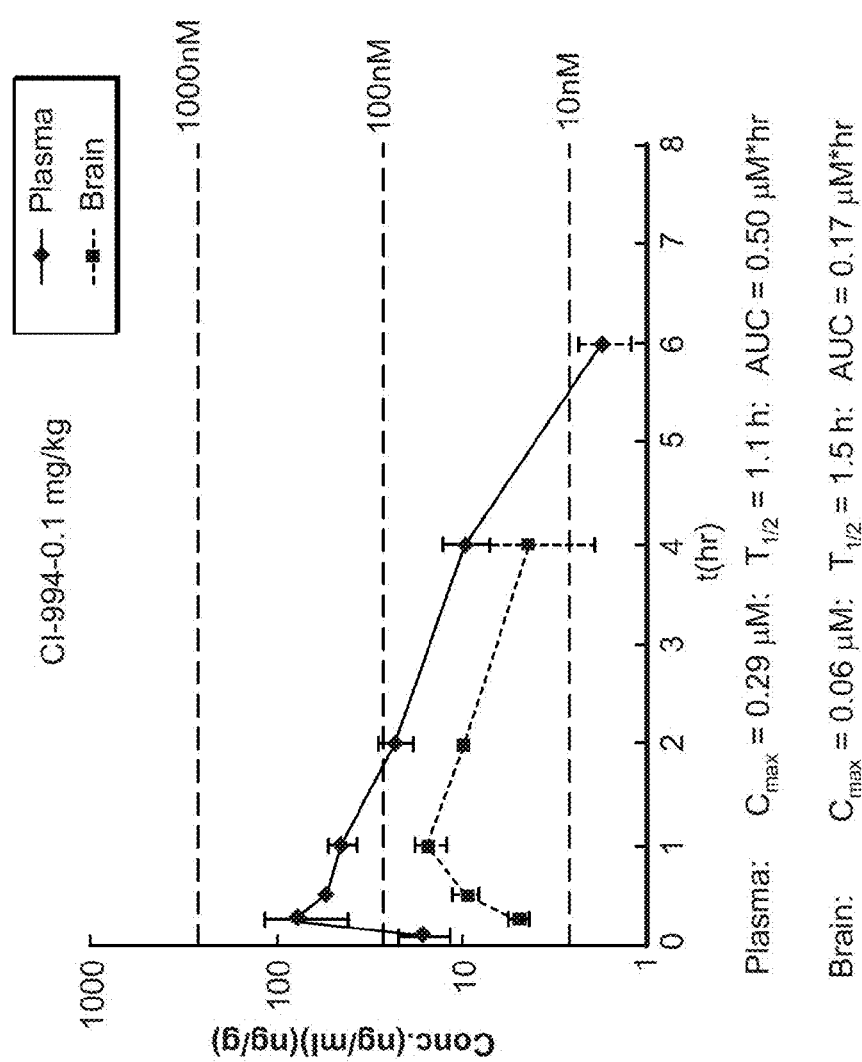
FIG. 50 is a summary of the pharmacokinetic data after a single dose of 0.1 mg/kg CI-994 administered systemically via intraperitoneal injection. The data demonstrates that CI-994 readily crosses the blood-brain barrier and is present after low dose administration.

Concentration-Time Curve of CI-994 in Plasma and Brain Following Single 0.1 mg/kg i.p. Dose in Mice A summary of the pharmacokinetic data after a single dose of 0.1 mg/kg CI-994 administered systemically via intraperitoneal injection is shown in FIG. 50. The concentration time curve for CI-994 in the plasma and brain of C-57 mice from 5 min to 8 h is indicated in the figure. The data demonstrates the concentration of CI-994 achieved in brain and plasma. CI-994 readily crosses the blood-brain barrier and is present after low dose administration.

Example 20

Figure 51:
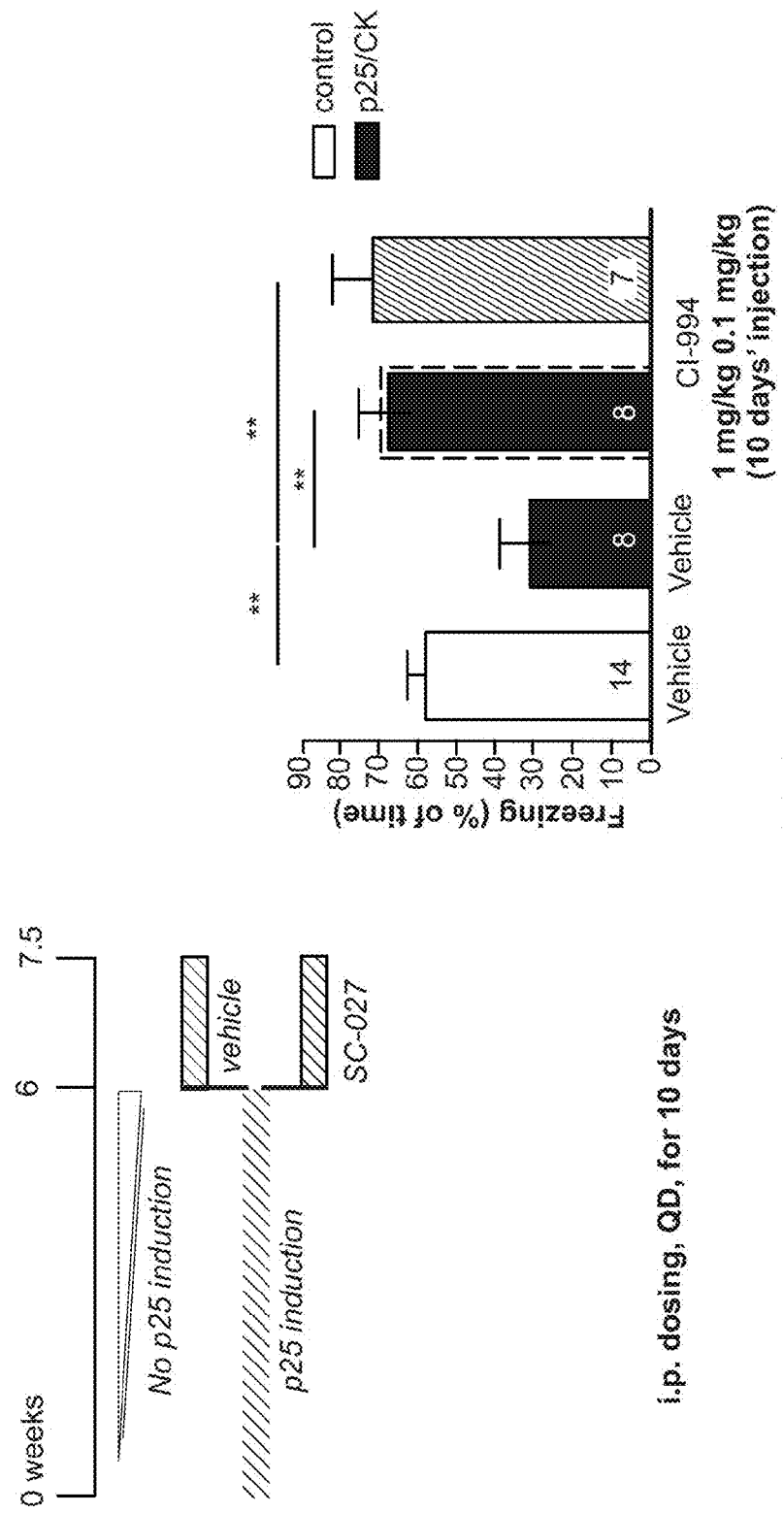
FIG. 51 shows that chronic CI-994, treatment ameliorated memory impairment in CK-p25 mice at 0.1 mg/kg.

CI-994 Ameliorates the Cognitive Deficits in CK-p25 Mice at 1.0 and 0.1 mg/kg p25-GFP was induced for 6 weeks in CK-p25 mice. Mice subsequently received chronic CI-994 (0.1 mg/kg or 1 mg/kg, i.p.), or vehicle for 10 days. All groups of mice were trained in contextual fear conditioning paradigm and tested 24 hours later. Chronic CI-994 treatment rescued memory impairment in CK-p25 mice (FIG. 51).

Example 21

CI-994 Treatment Restores H4K12 Acetylation and Dendritic Density in Cortical Neurons of CK-p25 Mice CK-p25 mice show reduced AcH4K12 in cortical neurons. Chronic CI-994 treatment (0.1 mg/kg, i.p.), for 10 days (beginning from 6 weeks after induction of p25) increased acetyaltion on H4K12. p25-GFP is induced for 6 weeks in CK-p25 mice.

CI-994 treatment upregulates MAP2 positive dendrites in CK-p25 mice. p25-GFP was induced for 6 weeks. Mice subsequently received chronic CI-994 treatment (0.1 mg/kg, i.p.) for 10 days. Mice were fixed and stained with MAP-2 antibody, which is a marker for dendrites. In 6-week induced CK-p25 brain, MAP2 staining intensity was markedly reduced. Chronic CI-994 treatment increased MAP2 staining intensity in the CK-P25 mice. These results showed that CI-994 induced active dendritic growth after neurodegeneration.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages of the invention are not necessarily encompassed by each embodiment of the invention.

What is claimed is:

1. A method for promoting fear extinction in a subject comprising:
systemically administering to the subject 4-(acetylamino)-N-(2-aminophenyl)benzamide (CI-994) or dinaline or a pharmaceutically acceptable salt or prodrug thereof in an effective amount to promote fear extinction.

2. The method of claim 1, wherein the CI-994 or dinaline is administered once every other day.

3. The method of claim 1, wherein 4-(acetylamino)-N-(2-aminophenyl)benzamide (CI-994) or dinaline or a pharmaceutically acceptable salt, ester, prodrug or metabolite thereof is administered before exposure to a fear associated context.

4. The method of claim 3, wherein the CI-994 or dinaline is administered 1-3 hours prior to the exposure to the fear associated context.

5. The method of claim 3, wherein the subject is provided with only a single administration of CI-994 or dinaline.

6. The method of claim 3, wherein the exposure to the fear associated context is in a reconsolidation paradigm.

7. The method of claim 3, wherein the CI-994 is administered in a dose of 0.001-50.0 mg/kg.

8. The method of claim 3, wherein the CI-994 is administered in a dose of 0.1-1.0 mg/kg.

9. The method of claim 3, wherein the CI-994 is administered in a dose of 30 mg/kg.

10. The method of claim 1, wherein the CI-994 or dinaline is administered by oral, transdermal, intravenous, cutaneous, subcutaneous, nasal, intramuscular, intraperitoneal, intracranial, or intracerebroventricular routes.

* * * * *